(12) United States Patent
Hucul et al.

(10) Patent No.: US 7,195,907 B2
(45) Date of Patent: Mar. 27, 2007

(54) NON-RIBOSOMAL PEPTIDE SYNTHETASES AND ASSOCIATED BIOSYNTHETIC GENES

(75) Inventors: John A. Hucul, New City, NY (US); Nathan Magarvey, Jamaica Plain, MA (US); Michael Greenstein, Peoria, IL (US)

(73) Assignee: Wyeth, Madison, NJ (US)

( * ) Notice: Subject to any disclaimer, the term of this patent is extended or adjusted under 35 U.S.C. 154(b) by 324 days.

(21) Appl. No.: 10/746,795

(22) Filed: Dec. 23, 2003

(65) Prior Publication Data
US 2004/0147007 A1 Jul. 29, 2004

Related U.S. Application Data

(63) Continuation-in-part of application No. 10/402,842, filed on Mar. 28, 2003.

(60) Provisional application No. 60/368,713, filed on Mar. 29, 2002.

(51) Int. Cl.
*C12N 1/20* (2006.01)
*C12N 15/00* (2006.01)
*C07H 21/04* (2006.01)

(52) U.S. Cl. .............. 435/252.33; 435/252.3; 435/252.35; 435/320.1; 435/183; 536/23.2; 536/23.1; 536/23.7

(58) Field of Classification Search ............... None
See application file for complete search history.

(56) References Cited

FOREIGN PATENT DOCUMENTS

| EP | 1262562 A1 | 12/2002 |
|---|---|---|
| WO | WO 00/40704 A1 | 1/2000 |
| WO | WO 00/20601 A1 | 4/2000 |
| WO | WO 02/24736 A1 | 2/2002 |
| WO | WO 02/77179 A1 | 10/2002 |
| WO | WO 02/101051 A1 | 12/2002 |

OTHER PUBLICATIONS

Marahiel et al., Chem Rev. 1997; 97: 265, 1-73.
Stachelhaus et al., Chemistry and Biology 1999; 6:493-505.

*Primary Examiner*—Nashaat T. Nashed
(74) *Attorney, Agent, or Firm*—Darby & Darby

(57) ABSTRACT

The present invention describes the identification of novel non-ribosomal peptide synthetases and associated biosynthetic genes from *Streptomyces hygroscopicus*. The present invention further provides methods for generating novel compounds, such as antibiotics, from these synthetases and associated genes.

17 Claims, 9 Drawing Sheets

AC98 BIOSYNTHETIC GENE CLUSTER
*Streptomyces hygroscopicus* NS17
48.2Kb

R¹ and R³ = H
R² = (isovaleryl group)

AC98-4

R² and R³ = H
R¹ = (isovaleryl group)

AC98-5 mmpA Module 1 Adenylation domain:
Two-Dimensional Representation of Binding Pocket L-Serine Activation

**mmpA Module 2 Adenylation domain:
Two-Dimensional Representation of Binding Pocket**

Glycine Activation mmpA Module 3 Adenylation domain:
Two-Dimensional Representation of Binding Pock Phenylalanine Activation mmpB Module 1 Adenylation domain: Two-Dimensional Representation of Binding Pocket

Tyrosine Activation

**mmpB Module 2 Adenylation domain:
Two-Dimensional Representation of Binding Pocket**

Cyclo-arginine Activation

SEQUENCE LISTING

<160> NUMBER OF SEQ ID NOS: 57

<210> SEQ ID NO 1
<211> LENGTH: 48200
<212> TYPE: DNA
<213> ORGANISM: Streptomyces hygroscopicus

<400> SEQUENCE: 1

```
agatcgcgtg tacgccgtcg ccgggatcat gcgtgcgccg tcgccaaggt gccggatttg      60
cggtaagtag tgggcgatgt ccgccacgcc gcgcccgcga cccgttctac ggccgttccg     120
ccccggagac ggccgctcgc tgctggcggc ctggtgccgc agcgccccgg acgatccgat     180
caccgccgcc cgcttccgga cgctgatcct gctcgacccc aatttcgacc cagagggtt     240 acgggtggcc gatctcgacg ggcaggtggt gggcgccgtc tacgccgtgc gccgccgtac     300
cccgctggcc ggcaccgacc tggagccgga cgtcggctgg atcctgttct tcttcgtcga     360
tccgccgcac cgccgtacgg gcctcggccg ccggctgctc accgatgccc tcgactggct     420
gcgcggacac ggccgcaccc gggtcgactt cgccccgtac gcccccact acgtgctccc     480 cggcctggac cgggccgcgt acccggaggc cgcccggctg ctggcgagcc tcggcttccg     540
tccccgctac gaggccgcgg cgatggaccg cggcctggtc ggctaccgca tgccggacga     600
ggtacggcgg cacgaggcgg ccctgacggc gcgcggccac cgattcggca ccccgtccga     660
cgacgatctg gtggacctgc tcgggctggc cgaggagttc accccgact gggcgcgggc     720 gatccggcag tgcctgaccg gcggcgcccc tctggaccgc atcgtcagcg cccgcgcacc     780
cgacgggcgg atggcgggct gggccatgca cggcgcgtac gacggtacgg ccgagcggtt     840 cggcccttc ggcgtacgga aggagctgcg cggcgccggt ctgggcaagg tgctgctgca     900
tctgacgctg gagcggatgc gggcgctcgg cgtgcacggg gcgtggttcc tgtggacggg     960
cgagcagagc ccggcggggc atctctaccg cgcgagcgga ttcaccacga cccggaggtt    1020
cacggtgctg cggtgggagg cgggatgagg cgccgtacat tcacggccgg ggccgcggcg    1080
ggggccgccc tgttggccgg ggccggatgc gacgcgcccg gtggcgccgg gcacggagac    1140
ggagagcacg gagacggaga cggcggtgac ggccggggca gcggcggccg tcgcggcgcc    1200
cccgtcaccc tgaccgtcct cacgcactac gcgagcgaac cgctcgcctc ggcgctgcaa    1260
accgtcgtcg acgcctggaa cgcgacgcac cggcgcatca cggtgcgcac ggccgcggtc    1320
aagttccccg atctgctgac gacttacatg gtgcggcagg ccgcgggcca gggcgccgac    1380
```

-continued

| | |
|---|---|
| atcatccatc cgtactgcct gtggaccggc cagctggtgc gggccggagt actgcgcccg | 1440 |
| gtgccgccca cggccacgcg gcagatccgc cgggacttca ccccggcggc cgtggcggcg | 1500 |
| tcgtccgtgc acggcacgct ctacggctac cccacggagg tgcagaccta cgcgctctac | 1560 |
| tacaacaagc ggctgctgcg gcaggccggt atcgacggac cgccgggtac ctggcaggag | 1620 |
| ctggaggacg cggcgtaccg caccgcccgc cgcgaccgcc acggcaacat gctggtgcag | 1680 |
| ggcttcgggc tgtcacgggc cgacgatgcg agcgtcgtgg ggcagacgct ggccctgctg | 1740 |
| gccgcgcgcg gcggcacatt cctcacctcc gacggacggc ggaccgccat cggctcggcg | 1800 |
| gccgggcggg atgtgctcga cctggagcgc cggctcatcg accgcggcgc cgccgactcc | 1860 |
| ggtatctcgc tcctgagggc ctttccgtcc ggccaggtgg cgatggcgat caacgccggc | 1920 |
| tggtggacgg cgagtctgcg cggcgcgatg ggggcggact accgcgaggt cggggtggcg | 1980 |
| ccggtgccgg ggcccgcacc ggacgaccgc ggcacgctcg ccacgggctt cctgctcggc | 2040 |
| gtgaacgcga agagcagata tccggggggag gcctgggagt tcctgcactg gctcaacggt | 2100 |
| gtgcgggcgc cggccgcccg gccggggcgc agcgcgggag gaggcgtccc ggtgtccagg | 2160 |
| atgagcgcgc tccaggtgtc ggtcggttcg atgaccgggc gggcggacga tatgcgggcg | 2220 |
| ctgctgggag gcgacggcga gagggacgcc gacggccgtg gtggcggcga ccggaacctc | 2280 |
| ggcccccttcc tggacgcgct cgcgctacgcc gtcccggaac cgaacggtcc gcgcgcgcag | 2340 |
| caggccaaat cgctgctgcg caagaacatc gaggacgtct ggacgggccg ggcctcggtc | 2400 |
| gatgccgcgc tgcgcaccgc cggccggcag atcgaccagg aactgtcccg gccctactga | 2460 |
| gccactcccc catgtcgtcg agaggtggtg ccgaatggct tcagccggcg gtggtcccgt | 2520 |
| cagggcggcc cggcggcggc agaccgccgt cgcctatctg ttcctgaccc cggccctgct | 2580 |
| gttcttcgcg gtcttcctcg ccctgccgct gctgttcgcc gtgctgctcg cgcagtcgcg | 2640 |
| ctgggccggc ttcgacctcg ccgatatcga gccggtcggg atggccaact tcaccgacct | 2700 |
| cttcgcccgc ggctcgacct tcctgacgcc cgtcctcacc aatacgctgc tgtacgccgt | 2760 |
| cggcaccgtc gcgatcgccc tcatcggcgc gctcaccctc gcgacctgca tcgacaacct | 2820 |
| tcgtttccag gggctttggc ggaccctcta tttcctcccg atcgtgacga ccgtggtcgc | 2880 |
| cgtcggcaac gtatggaagt acatgtacgc accgggcggg ctgatcaacg gagtgctcaa | 2940 |
| cggtctgggt ctgcattccg tggcctttct ccaggacccc ggcacggcgc tgccgtccgt | 3000 |
| cgtcgtggtg caggcatggg cctccatggg aaccgcgatc ctgattctca ccgcgggcct | 3060 |
| gaagtcgatc cccgaggcct attacgaggc cgccgagctg gacggtgccg cgccggcac | 3120 |
| cgttttccgg cgcatcaccc tgccgctgct ccggccgtcc ctgctcttcg tctgcatcac | 3180 |
| ccaattcatc accggattac agtcgttcgc cctgatcaat gtcatgacgg acgacggcgg | 3240 |
| accgggcgat gcgacgaatg tcgcggcccct ggagatgtat cagcaggcgt tcaggtacgg | 3300 |
| cgactgggga atcgccagtg ccgccgcctt tgtgctgttc ctggtcattg tcgcgatcac | 3360 |
| ggtgggggcag ctctggctgt tccgccggaa aggcggggaa tcgtgagccg gtccgctcgt | 3420 |
| cggcgccggg gccgtcgccg cccctgggc tcgtacgccg tggtcgtcgc ggggccgcc | 3480 |
| ctcaccctcg tcccgttcct cgacatgctg ctgacctcgt tcaaggggcc cggcgaatac | 3540 |
| gggaaactcc cctaccgatt cctcccccag gcgttcgacc tttccaacta ccgtgccgcg | 3600 |
| atggagcagc tggatctgcc cctgcttttc cgcaacagcg tcatcgccac cgccgtcatc | 3660 |
| accggatcca tcctggtgac ctccgcgctc gccggatacg cgctggccaa gctgcgcttc | 3720 |
| cccggccggg aggtgatctt ccgcctggtc ctgtccacga tgatgttccc gccgttcctc | 3780 |

-continued

```
ttcttcatcc cgcactttct gatcctggtg cactggcccg cgccggcgg caacgacctg    3840
ctgggccgcg gcggggcggg cctcaccgtg agccttgcgg cgctggtcat gccgttcctc    3900
gtatccggtt tcgggatctt tctgatgcgg caattcatgg tctccatccc ggacgaactg    3960
ctggaggcgg cccgtatcga cggcgccggc gaattcgccc tctggtggcg catcgtgctg    4020
ccccagacga aaccggtggc ggtcaccctc gcgctgctca ccttcgtcaa cgcctggaac    4080
gaatacatct gggcgctgct gatctccacc gccaatccgc ggctgatgac gctgccggtg    4140
ggcatccaga tgctgcagag ctatctcgac cccgaccgta tggtcccggt catgatggcc    4200
ggcctggtgc tgagcatcct gccggtcctg ctgctcttcc tgctgctcca gaagcactac    4260
ctgcgcgggg tgatgctcag cggcctcaag tgacgtgcgt cctgggccga tgtggtcccg    4320
cggtgcaccc gccgaggttg acttctccgt aaaacatgat gagttccggt ttctcctggg    4380
ctgttgtggc aactgtggtg agagtttctg accccctcagg aggaaccatg gcttccgact    4440
cgtcgtcccc gacgccgatg ccggccgtgt cgttgatcgt gccgacgttc aacgaggcag    4500
cgaacattga tgagttgctc gacgcgtgt gtgcggcgat cccggcgggt ctggaggtcg    4560
aggtgctgtt cgtcgacgac tcgacggatg acacaccgga agtcatcgag aaggcggccg    4620
cgcgctgtcc gatgccggtg tcggtgctgc accgggaggt tcccgaaggg gggctcggcg    4680
gagcggtggt ggccgggatc gcccgtacga gtgcgccgtg gatcatggtg atggacgccg    4740
atctgcagca tccgccggag ctgctgccgc agttgatcga ggctggtgag cgcgcggcgg    4800
ccgagttggt ggtggccagc agatacgcgg agggcgggag ccgtggcggg ctggccggcg    4860
ggtaccgggt ggccgtgtcg ggggcgtcga ccgcgctgac caagtcgctg ttcccccggc    4920
tgctgcgcgg ggtctccgac ccgatgagcg ggtgcttcgc catccggcgg gaggcggtcg    4980
accgcgccgt acaggagggc gagacccggc aggaaggggg gctgcggccg ctcggctaca    5040
agattctgct ggagctcgcg gtgcgctgcc ggccgcgcgg ggtggtggag gtgccgtacg    5100
agttcgggga gcggttcgcc ggcgagtcga agtcgacggt gcgcgagggg ctgcggttcc    5160
tgcggcatct ggcggagctg cggaccagcg acaagcgggc ccggatggtg gccttcgggc    5220
tgatcgggt gtcgggcttc gtaccgaatc tgctggcgct gtgggcgctg accggtgcca    5280
cgaccctgca ttacgcggtg gcggaggtgc tggccaatca gctcgggtg ctgtggaact    5340
tcgccctgct ggacttcctg gtctaccgga gcgggaaacc ggggcgcggg gccggccggc    5400
tgctggggtt cgcggcgctc agcaacgcgg atctgctggc gcggatcccg ttgatgatgc    5460
tgttcgtgga gcaggccggg atggggccgg tgccggcgac cgtgatcagt ctcgtggtgg    5520
tgttcgcgct gcggttcctg ctggtcgaca cgttgatcta ccggcgcaag ggcggctg     5580
ccaagcgcgc ggcggacgcg gcggtcaccg gcgggcaggg cgagcgcgct gcttagctga    5640
caaggcaaac tcgtggcggc ccgccccggc cggacagcag actccgagcg atgatctcgc    5700
cggattccac ctggacggac agaggcggag aaacgtgctg acagctcccg ttggtgtgga    5760
aacggatccg cgttcggcgg tacgccggc ccggcggccg gcggccgtcg tcgcgggcgc    5820
cgtgaccgtc gtgctgctcg ccctgtccga caggtacggc tacaacgtcg acgagctgta    5880
tttccggctg ctcggcgaac acggctgggc ctggggctac accgaccagc cgccgctggt    5940
gccggcgctg gtgcacgcca ccgcccaggt cctcggcgac tcggtgtggg cgatccgggt    6000
gccggcggcg ctgtgcgcag gggccgtggt gctgctcggg gcgctgatca ccgccgaact    6060
cggcggcacc cgccgggcac agactctttc cgccctgggt ctgggcagct cgttcctggt    6120
```

```
gctcagcgtc ggccacatca tggtgaccac caccctggac atgctcgcct gggccgcggt    6180
gctgctcttc gtcctgcggg cgctgctgcg ctcggagggc aagtggtggc tgtgggcggg    6240
ggtggtgctg ggcctggcgc tgtacgccaa gtacatcgtg gcgctgctgc cggtggcgct    6300
gctggccggg ctcgcgctgg tcggtccgcg gaaggtgttc cgtgaccggt ggctgtacgc    6360
ggggatcgcg ttggcgctgg ccatcggctc gccgaacctg atctaccagg ccacccatga    6420
cttcccgcag ctgcagatgg ccgatgcgct gggtgccacc gacggcccga tgaaccgggt    6480
catcttcgtg ccgagcctgg tgatcctgct cggtccggtg ctgaccgtgg tgtgggtcgc    6540
ggggctggtg aagctgctgc gtgacccggc atggcggccg gtgcgggcgc tggcaccggc    6600
gttcgtggtc ggggtggcgc tgaccctcta cggcggtggc cggcccgact acgtcggcgg    6660
gttcctgatc gggctgttcg cggccggggc ggtggccgcc gaccggtgga tggggcggcg    6720
tacgtcccgg cgggtgctgc tgtgcgccgg actggccgcc agtgcggtgc tccaggtgct    6780
gatgcgcctg ccggtgctgc cgcagagctc cccgttcgtg ccgctgaaca acatctccct    6840
ggagagcgtc ggctggccgc ggctcgccga gcaggtgcgc acggcgtacg aggcgctgcc    6900
gcggcagcag cgggagcggg ccgtggtgct cgccgacaac ctcggggaga tcggcgcgct    6960
ggaccgctac gggcacgggc tgcccgcggt gttcagcggc cacaacgaac tgcacaagtg    7020
gggcccgccg ccggagcgcg ccgatgtggt ggtcgcggtg ggcgtgcccc ggtcccggct    7080
ggccgcgggg ttcacctcgt gcaccgtcgt gggacgggtc gacaacggcg tcggcgtcga    7140
gaacgccgag cagggcagac cgatcacggt gtgccacggc cgcaaggctt cctgggcccg    7200
actgtggccc tcctaccact acttgagcgg ctgatgtgcc cctgcacccc gggccgtgtg    7260
cgaatcgaca actcagcggg aagtgaggcg tgatgacgac atccctcgac agggattcca    7320
gggcggccgc ggccgggccg ggggtgttcc gcccggcgcc gatggcgtgg cggccggtcg    7380
ccgtggtggt ggccgcgctg gccgtgctgt tgttcgcctt cgccggcgaa tacgctacc    7440
acgccgacga gttgtacttc cggctgctcg gggtgcacgg cttcgcctgg ggctatgtgg    7500
accagccgcc gctgctgcca ctggccgtac ggacctcgat ggagatcttc ggcgacagca    7560
tgtgggcgat ccgggtgccc gccgtgctgt gcgcggcggc cgtgaccgcg ctcggcgcga    7620
tgatcgccgc cgagctgggc ggttcccggc gggcccagac gctgaccgcg ttcgggtgg     7680
ccacctcgac gatggtgctc agcttcggcc actggatcct caccaccagc ttcgacaccg    7740
tggcgtgggc cgcggtgctg ctgttcgtga tgcgggtgct gctgcgcggc gagagcaagt    7800
ggtggctgtg ggccggggtg gtggtcggtg tcgcgctgta cgccaagtac atcgtgctgc    7860
tgctgccggt ggcgctgctg gtggggctgg cgctggtcgg tccgcggaag gtcttccgcg    7920
acgggaagct gtacgcgggc acggcgctgg cgctggtcat cggctcgccg aacctgatct    7980
accaggccac ccatgacttc ccgcagctgc agatggcgga ggggctggcg ggcaccgacg    8040
gcgaggcgaa ccgcgccatg ttcgccacga acctgatcct gctgttcggc ccgcgctgt     8100
tcgtgctgtg catgatcggg ctggtcaagc tgttccgggt gccggagtgg aagcccgtac    8160
ggacactggc cgtcggctat ctcgcggcca ccgcggcgtc gtacctcatc gagggcggcc    8220
ggccggacta caccggcgga ctgctgatcg cgctgctggc cgcgggtgt gtgacggccg     8280
accgtgggc gggcgcccgc aagctgcggc tctcggtgct cgcggtctcg ctgacgctca    8340
gcaccgcggt gcagatgctg ctgtcgctgc cggtgatccc caagagctcg ctgcgcgact    8400
tccagatcgc cagcatggcg ctggagacgt tgggctggcc ccgtctggtc cagcagaccg    8460
aggcggccta ccgcgcactg ccggccgcgg accgcgaccg cgcgatcgtg ctcaccgaga    8520
```

```
acttcggcga ggcggggcgcc ctggaccact acgggcacgg gctgccgaag gtgtacagcg   8580
gccacaacga gctgtaccac tggggcccgc cgccgcagcg cgccgaggtg gtggtcgcgg   8640
tgggcatcga ccggaaccgg ctgtccgccg acttcaccag ctgcaaggtc gtcgaccaca   8700
tcgacaaccg cctgggcatc gacaatccgg aacagggcgt gccgatcacg gtgtgccacg   8760
gccccaagaa gccctggtcc gcgctgtggc cgacctaccg gcactacaac gcctatctgt   8820
agcgcgcctc tcgtccccca ccccgcggcc cggtccgaag caccttcgga ccgggccgtc   8880
cgccgacctg cttcgctgca cggtaaaagt cgtggatcag ccgcggagtt cacccgagac   8940
tggaaatcgc tggactgtgt acgcccatcc aatcgacttc cggacgaccc ctttcggggt   9000
ggaggcgtga tatgagtacc gaggtttccg aggcgcaggc gcgacgcgcc gtggcagaca   9060
tcttcaactc gacgctggct tcttcggcca tcggcgccgc gtgggagctc ggagctcttg   9120
acgagctgcg ggagaacggc aagttggatg tctccgattt cgccgtacgc catgatctgc   9180
acgagccggc ggtggtcggc atgttcaccg cgctggcgag tgtgggaatc gtgcggcgcg   9240
agggcgccac cgtcgtcgtc ggcccgtact tcgacgaggc caatcaccac cgttcactgt   9300
tccactggct caatcagggc agcggcgagc tcttccgccg catgccgcag gtgctgccga   9360
acgagaaccg cacaggaaag ttctaccagc gggacgcggg ggcgatcagc tacgcgtgcc   9420
gcgagatcag cgagcgctat ttcgacccgg cgttctgggc cgcggtcgac ggtctgggtt   9480
acacccccac caccgtcgcc gacctggggt ccggcagcgg tgagcggctg atccagatcg   9540
cccggcggtt ccccggcgtc cgcggcctcg gcgtggacat cgccgacggc gcgatcgcca   9600
tggcggagaa ggaggtggcc gccaagggat tcggcgacca gatctccttc gtgcggggcg   9660
acgcgcgcac catcgaccag gtctcggcgc gcggggaatt cgccgaggtc gatctgctca   9720
cctgcttcat gatggggcac gacttctggc ccgcgagaa ctgtgtgcag acgctgcgaa   9780
agctgcgcgc ggcattcccg aatgtgcgcc ggttcctgct cggcgacgcc acccgcaccg   9840
tcggtatccc cgaccgcgaa ctccccgtat tcaccctggg attcgagttc gggcacgaca   9900
tgatgggcgt ttacctgccg accctcgatg aatgggacgg ggtattcgaa gagggtggct   9960
ggcgctgtgt gaagaagcac gccatcgact cgctgtcggt ctccgtggtc ttcgaactcg   10020
agtaaccgca cacgcgcata tcgatacgcg tcggcagaggg ggttttccat gggtgagtgg   10080
cgcgatcgcc gcctggacga attgttcgcc gagcaggccg cgagaacacc ggagcgtacc   10140
gcggtggtct tcgagggccg ggcggtgagt tatcgggaac tcgacgcccg cgccgagcgg   10200
ctggccgctg tgctggccgg ccgcggcgcg ggacccgagc ggttcatcgc gctgctgctg   10260
ccccgctccg ccgaactgat cgtggccatc ctcgccgtac tgaagtccgg cgccggatac   10320
atcccgatcg acccggagta cccggccgac cgcatcgcct acatcctcgg cgacgcgcgc   10380
ccggtggcga cgatcaccac cgccgaggtg cgggacggtc tgccggaccc ggacaccggc   10440
tccgggaccg actggctgat cctggacgag tccgggtacg agcaggagcc ggccggggcg   10500
cgcccgcagc ccgccccggc cgcccgcgcg tccgcggaga accccgccta cgtcatctac   10560
acctccggct cgaccggccg gcccaagggc gtggtgatcc cgcacagcaa tgtgggacgg   10620
ctgctgtcgt ccaccgccca ctggtacggc ttcgacgagc aggacgtctg gccgctgttc   10680
cactccttcg ccttcgatgt ctcggtctgg gagatctggg gcgcgctgct gcacggcggc   10740
aagctggtcg tcgtcccgca tgccgtcacc cgcgccccgg ccgacttcct gcggctgctg   10800
gtcgaggaac gggtcaccgt cctgaaccag acgccttcgg cgttctacca gctgatggcc   10860
```

```
gccgaccggg agaaccccgc gctcggcgcc caactcgccc tgcgttatgt ggtgttcgcg   10920
ggtgaggcgc tggacctggg caagctcgcc gactggtacg agcggcacga tgaccgggcg   10980
ccgacgctgg tcaacatgta cggcatcacc gagaccaccg tgcactcctc gttcctcgca   11040
ctggacaagg agggcgcggc cggcgccacg ggcagcgccg tcggcgtcgc cctccccgac   11100
ctgaccttcc atgtcctcga cgaggacctg cggcccgtcc cggtcggcgc ggagggcgag   11160
ctgtatgtgg ccgggcccgg gctggcacgg aactacgcgg gccggccggg gctgaccgcg   11220
gagcgcttcg tggcctgccc gttcggcccg cccggggccc gtatgtaccg ctcgggcgac   11280
ctggtgcggc cgctgccgga cggcggcctc gaataccctgc ggcgcagcga cgaccaggtc   11340
aagatccgcg gtttccggat cgaactgggt gagatctcgc acgcactggc ccaggacccc   11400
tcggtcgacc aggccacggt ggtggtccgc gacgaggcgt cgggcgagcg caggctggtg   11460
gcgtacgtcg ttccggccgg ctccgcccgt cccaccccgt cccggctgcg tgccgcgctg   11520
gccacccgcc tgcccggcta catggtcccc accgccttcc acgtcatgcc ggccttcccg   11580
ctgaccgcca acggcaagct ggaccgcagg gcgctgcccg cgcccacccg ccaggacagc   11640
gtcgacgccg actacgccgc ccccgagggc gccaccgagg aggcgctggc cgccatctgg   11700
cgcgaggtgc tcggcgtcga acagatcggt gccgacgacg acttcttcga gctcggcggt   11760
gactcgctgt ccgtggtgcg ggcgctgtcg cggatgcgga ccggcctggg gctgcgcctg   11820
acggccgcgg agttcttcgc caccccccacc gtccgggcac tggccgcgcg ccgcgagcgg   11880
ggcacgatcg gcgcgccgga gcagataccg ccgcgccgc gtaccggcgc gctgccgctg   11940
tccttcaccc agcagcggtt ctggctcttc cacgaactcg accccggcga ggtcgagtac   12000
aacgtccact ccgcgctgcg gctgcgcggc accctcgacc tccccgcgct gcgcaccgcg   12060
ctcggcgggc tgatcgcccg ccatgagccg ctgcggacga ccgtggtctc cgacgacggc   12120
cgccccaccg cggtcatcgc cccgcccgag ggcttcccgg tcccgctcac cgtcgaggat   12180
ctctccgcgc tgaccggcga cgaccaggag gccgcccagc ggcgactgct ggccgaggag   12240
gtcgcccggc ccttcgacct ggccgccggc ccggtgctgc gggtgctggt gatccgccgc   12300
ggcgagcgcg atcacgccct ggtgatcggg gtgcatcacc tcgccaccga cggctggtcg   12360
atggggctgc tcaccgacga gctgagcgcg cgctacgacg ccgcgcgccg cggggtgccc   12420
gccgcgctgg agccgctgcc ggtccactac agcgactacg ccgcctggca gcgcgccacc   12480
gtggacgacg gccggctggt gccccagatc gactactggc gcgaccggct ggcggatgtg   12540
gcaccgctgc aactgcccac cgaccggccc cggcccgcgc tgaagacctc ggccggtgcg   12600
gcgcaccgct tcaccctcga ccgccggctg gtcgccgccc tcaaggagct gagcgccgcc   12660
catggcgcca cgctcttcat gaccctgacc gccgcgttgc aggtgctgct cgcccgctac   12720
tccggacagc aggacatcgc gctgggcacc gccgtctccg gccgggacca cccgcaggtg   12780
gagcggctgg tcggcgcgtt catcaacacc gtggtgctcc gctccgacgt gcgcggcgag   12840
ctgcccttcc acgaattcct cggggaggta cgggagacgg tgctgggcgc cttcgcgcac   12900
caggaccttc cgttcgaccg gctcgtggac gcgctgggcg ccgagcgcga cccgagccgt   12960
accccgctgg tccaggcgat gctgctgctg cagaacgccc cggccggtgc ggaggagttc   13020
gccgggctgc gcaccgagac cgtcgcgctg ccgcgcccgg ccgcgatctt cgacctgacg   13080
gtggactgca cggagcgggc cggggcgctg gaggtgatgg tcgagtacaa caccgatctg   13140
ttcgacgcga cgaccatcga gcggctctcg ggccatctgc gggtgctgct ggacgccgta   13200
tgcgcggcac cgcggcgcca ggtgcgcgat ctgccgctgc tgccggcggc cgaacgcgac   13260
```

-continued

```
acgctgctga ccggctggaa cgacaccgcc gccgcactgc cgacgacgct cggggtgcac      13320
cgccagttcg ccgagcgggc ccgcaccacc ccggacgcgc tcgccgtcac acactgcgga      13380
cagaccctca cctacgccca actcgacgcg cgcgccaacc agttggcgca ctacctgggc      13440
gctctcggcg tcggccgggg caccccgtg gtgctgaacc tggcgcgcaa gccgcagctg       13500
atcgtggcga tgctcgcggt gctcaaggcc ggcggcgcgt acgtaccgac cgcgctggac      13560
accccggcgg cacggctcgg gcatctcctg gaggagaccg gcaccccgt gctgctgacc        13620
accgcgcggc aggccggagc gctgcccccg accgaggcga gcgtcatcga cctcgacgcg      13680
gccgggccgg acatcgcccg gcatccggag cacgaccccc aggtggcgac ccggcccgag      13740
gacctcgcgt acatcgtcta cacctccggg tccaccggcc gccccaaggg cgtcgcggtg      13800
ccgcacagcg cgctgaccga ctactgcgcc tggcacaacg acgcgctgga cgtcggcccc      13860
gaggaccgcg ggtcgtccgt ggtcggcctg gccttcgacg tcgcggtcgg cgaggtgtgg      13920
ccgtatctgt gcgcgggcgc ccgcgtggac cagcccgacc aggagacgct ggacgatccg      13980
acggcgctgg tggagtggtt cgccgagaac ggcaccacgg tcgcctatct gccgaccccg      14040
cgcatcgaat ccctgctgga cgtagcggcg atcaccacca cccggctgcg caccgtcctg      14100
gtcatcggcg actcgctgcg ccgcaggccg cagcccggac tgccgttcac cctgctcaac      14160
gcctacgggc ccgcggaggc gacggtggcc gccacccagg cggtggtcga gcccctggga      14220
cccgacgcgc ccgccgggct gccgtccatc ggcgcccccgc tgtacaacac cgccgcctat    14280
gtcctcgacg accggctgtg cccggtcccc gtcggggtgc ccggcgagct gtacctcgcc     14340
ggcgcgggtc tggcgcaggg ctatcagggc cgccccgacc tgaccgcgga gcgcttcgtc     14400
ggctgccccct tcgggccgcc cggaacccgg atgtaccgca cgggtgacat cgtgcgatgg     14460
ctaccggacg gcaccctgga cttcctcggc cggatcgaca accaggtcaa actgcgcggc      14520
taccgcatcg aactcggcga gatcgagagc gtgctggccc gccgcgagga gctctcgcag      14580
gtgttcgtca cggtccgcga gccgtccccc ggccgccggt ccctggtcgc ctacctcgtc     14640
gccgaccggg gcaccgcgcc cgaccggag gagctcgccg gatacatcgc ctccgtactc       14700
ccggagtaca tggttccgtc ctccttcgta ctgctcgacg cgctgccgct gaccgcgaac      14760
ggcaagatcg accggcgggc gctgcccgag ccggagccgg ccggcggcga gggcgccgcg     14820
tatgtcgcgc ccggcaacga ggtcgaggag accctggccg ccatctgggc cgaggtgctc      14880
ggcgtcgaac gggtcggcgt gcaggacaac ttcttcgccc tcggcggcga ctcgatcagc      14940
ggtctgcaga ccgccgtacg ggcccgccgg gccgggctgc gactggcctc caaggacctc     15000
ttccagcgcc agaccatcgc ggcgctgagc ccgtggtga cggtggagcg gaccacggcg       15060
gacgccgacc ccgcaccgtc cgaccggccg accgcgccgt tcgcgctcag cggtctggac      15120
cgggtcggtg tggagcggct gaccgcggac ggcggcccgg ccgaggacgc ctaccgcctg      15180
accccgatgc agagcgggct gctcttccac accctgatgc acgccgaacg cggcatgtac     15240
atcgagcagt ccacttcgc cctgcacagc atccgcgagc cggagctgct ggccaccgcc      15300
tggcagcggg tcgtcgaccg caccctgtg ctccgtacgt cactggcctg ggacggcctc       15360
gccgaaccgc tccaggtcgt gcgcaccggc gtccggatac cggtggcaca gctcgactgg     15420
acggcactgg acgaggccgg acagcggcag gccctgagcg ggtatctgac cgaggaccgc     15480
acgcgcgggc tcgatctgca caccgcgcca ctcgcccgga tcgccgtcgc ccgcctgggc     15540
ggcgaccagg tccggctggt gtggacgttc caccatctgc tgctgacgg ctggagcgtc      15600
```

```
gtacaggtgc tgtccgaggt gctcggcgag tacgccgcgc tcgccgacgg catcccgtac   15660
accccgcaac tgcggcacac ctacgccgag ttcgtcggcc agctggcggg gcaggaccac   15720
accgccgccg agaagtactg gcgtgccgcg ctcaccggcc gtgagtcgcc caccccgctg   15780
ccgtacgacc ggccgcgccc cgacgccat  caggccgccc ccgacgccga gctgaagctg   15840
cggctgccgg ccgcggtgac cggccgactg ggcaccgcgg cgaagcgggc cggggtgacg   15900
atgaacaccg tggtgcaggg cttgtgggcg ctgctgctgg cccgccacag cggtgagcgg   15960
gacgtactgt tcggcgccac ggtcgccggc cggcccgacg atctggcggg gcgcggaatcg  16020 gtgatcggcc tgttcatcaa caccctttcc gtgcgcgtcg acgtcgatcc ggacgccggt   16080
ctgctgagct ggctgcgccg ggtgcaggac gagcaggccg aggcgcgcgc ccatgagcag   16140
gtctcgctcg cccaggtgca gggctgggcg ccggagcggg cgcacggcgg actgttcgac   16200
agcgtgctgg ccttcgagaa cttcccggcc gacctcggtc cgccgggaa  ctacgggctg   16260 cggctcgacg ccatcgaggc cagcaacacc tccaactacc cgctcaacgc catcgttcag   16320
ctcaacgaag agctgaccgt gctgctgcgc tacgacaccg cgctgttcga cgcggacacc   16380
gtggcgcggt tggccggcca tctgcacacg ctgctggagg agaccgccga gaaccccgac   16440
cgccgggtcg gcgagctgcc cctgctcacc gccgccgagc ggcacaccat cgtgcacacc   16500
tggaccgaca ccgcctcgga ctactcggtc gaccgccggc tggacgcggt catcgccgaa   16560
caggccgcgg cccggccgac cgcgatcgcc gtcgtcgacg gtgaacggca gctgagttac   16620
ggcgagttgg accgccgcgc caaccagctg gcacaccatc tgcgcgccgc gggcgtgggc   16680
cgggacgccc tcgtcgggat cgccgtcgag cgcagcgcgg aggtcgtcgt ggccatcctc   16740
ggcacgctca aggcgggcgc cgcgtatgtg ccgctcgacc ccgaattccc cgcgcagcgg   16800
ctcgccacca tgctgtccga gtcccggccc gcggtcctgc tcacccagga acacctgctg   16860
gcggggctgc cgccgacgga cgcccgggtg gtgtgcgtgg accgggacct ggcggccatc   16920
gaggcgcacc ccaccgccgc gccggtctcc ggcggcgacg ccggcgacct ggcctatgtc   16980
acctacacct cgggctccac cggccgcccc aagggcgtca tggtcgagca ccgctcgctg   17040
ttcaacatca tcaccgaggc cggacggctc tacgacctgg gccccgacag ccggatgctg   17100
cagttctaca caatgagctt cgacggcggc gtctgggagg tcttcctgac gctgaccgcc   17160
ggcgccaccc tcgtcatcgc ggaccccgag gcccgccaga gccggcccca cctcgccgag   17220
cagctgcgcg cggagtcgat caccgcgctg acgctgccgc ccgcggtggc ctcggtgctg   17280
gacgcggcct cgctgcccgg catacgcagc ctggggctcg ccggggatgt gctcgcgccc   17340
gaactcgccc gggagtgggc gcggggggcg cggctgttca acatctacgg gcccagcgag   17400
gcgaccctgt ccgtcgccct gcaccgcgtc gaccccgggg ccgccgggcg ccaggtgccg   17460
ctcggaccgc cggtgcccaa caccgttttc catgtgctcg acgagcggct ggccgtggtc   17520
ccggtcgggg tgaccggcga gctctacatc ggcggtgcgg gcctggcccg cggctacctg   17580
ggccgccccg acctgaccgc gcagcgcttc gtcgccgacc cgttcggacc gccgggatcc   17640
cgtctctacc gcaccggtga cctgatccgc tggaccccgc aggggcggct ggagttcgcc   17700
gggcgggtgg acaaccaggt caagatccgc ggctaccgtg tcgagcccgc cgaggtggag   17760
agcgcactgc tgcggcagcc cggcgtcgcg gaggcggtgg tgatcgcccg ggacgacgac   17820
accggccaca gcggctggtc gcctatgtc  gtaccggacg ggagcggaac cgccccggaa   17880
cgcgccgccc tgctgcgcgc cctgggcggc caactcccg  gctacatggt gccgtcggcc   17940
ctcgtcaccc tgcccgagct accgctcgga ccgaccggca aggtcgatgt gcgggcgctg   18000
```

```
ccggcaccgg atccggccgc cggcggcacc gccgaccgca tcccgccccg cacccccacg    18060
gaagaggcac tggccctcat ctgggtggag ctgctcgggc tcgaacacgt cggcgtcgag    18120
gacaacttct tcgacctcgg cggcgactcc atcaccagcc tgcggttgat gtcgcggatg    18180
ggcggcgcgt tcggtgtgga cgtctcaccc cgcgacttct tcgacgcccc caccatcgcc    18240
gcccttgccg agcgcctaga ggaaaagatc ctggcgcagt tggaagaagc cgtcggaggc    18300
ggcgccctat gaccagctct gcagcggacc agcccgacaa cccgaacacc accacccegg    18360 cgtcgcgtgc cgagcgcacc gccgcgctgc cggcccatgt gcaggagctg ctgcgcgccc    18420
ggctggccgg ccgggccgcc gcgacgggcg gcgcggacac catcccgcgc atcgggcacg    18480 acggcccegt cgcgctctcg cccgcccagg aacgcctctg gtacctgcat gagctcgaac    18540
cggagagcaa cgagtacaac accctgcgcg tcctgcggct gcgcggcgac ctcgaccccg    18600
gcgcgctgtc cgcggcgctg agcgagatct tcgcccggca cggcgcgctc cgcaccacct    18660
tcggctcccg cgagggcac gccgagcaga ccgtgcatcc gcccgtaccg acaccgctgc    18720
cgctcgtcga cctgtcggcg gcggacgacg gcgagcggga cgacgcgctg cggaccctgc    18780
tgcagtacga ggcccggcgc cccttcgacc tgcgccgcgg cccggtgctg cgggcgcagc    18840
tgatccggct ggcggccgac gaccatgtcc tcgcgctggc cctgcatcac atcgtcaccg    18900
acggctggtc gatgggcgtg ctcaccggcg agctcaccgc ccactacgcc gcgacgctgc    18960
gcggtgcgcc cgccgtactg cccgaacttc cggtgagcta cctcgatgtc gccgtctggc    19020
agcgtgacca gctgagctcc gcgcggctgc gcgaggggct cgaccactgg cgccgggagc    19080
tggccgggct ggtcccgctc gatctgccga cgacctggca gcggccgccg gtccgcacca    19140
gcgccggagc gctgcactcc ttcgagatcc ccccggcggt cgccgcacgc cttcgggagc    19200
tgggccggga acagggcgcc acgctgttca tggcgctggt cgccgcggtc cagctgctgc    19260
tgtcgcgctg gtcggggcag cgggacatcg cggtgggcac cgccgcggcc gggcgcggcc    19320
ggaccgagac cgagaatctg atcggcttct tcgtcaacaa tctggtcctg cgctcccgga    19380
tcgatgagac gcgtcgttc accgagctgc tgcgggcggt acgcgcgacg gtcctggacg    19440
ccttcgccca cgaggatgtg ccgttccagc gggtcgtcga ggcgctgcat ccggagcgcg    19500
acctcagccg gccgccgctg ccgaggtcg cggtgaatct gcacaacacc ccgcggaccg    19560
acacggagct gcccgggctg cggatcgagg agatgccgcc gccggtgttc gcctccagca    19620
tggacctctc gttcgacttc accgagcgcg acgaccggct cgaagggcac ctcacctaca    19680
acaccgatct gttcgccgcg gacgccgccg cgcggatggc cgcgcagctg gtcaccctgc    19740
tcgaggacct caccegccgg cccgcggtcc cggtggccgg gctggccgtg ctgccggccg    19800
ccgagcaccg tcgggtgacc gaggagtggc cgcactccgg gcccggccgg gagccgcgta    19860
ccgcaccgga gttgttcgcc gcgcaggtcg cgcggacccc tgatgcggat gcgctggtct    19920
ccgacgagga gacgctcagc tatgccgagc tggacggccg tatcaaccag tgggcgcggc    19980
tgctactggc ccggggtgcc gggccggaga cgctggtggc ggtggcgctg ccccgctccg    20040
cgcagatggt cacggcgatc ctggcgatcc agaagaccgg tgccgcctat ctgccgctgg    20100
acccgaagag ccccgcggaa cgcaaccggc tgatgatcga ggacgcccgc ccgctgctgg    20160
tgctgacctc ggccgggttc ggcgacgcg cggaactcgg cgcgcccgca ctgttcctgg    20220
acgacccgga cacccgcgcc gccgcaggcg agctgtccgc cggcccgctg gcggccgccg    20280
agctgcccgc cccgctgctg cccggccacc cggcctacgt catctacacc tccggttcca    20340
```

-continued

```
ccggccgccc caagggcgtg gtggtcaccc acaccggtgt gcacggcctc gtggcggcgc    20400
agtcggcgca cttccgtacc gggcacggcg cgcgggtgct gtcgttcgcc tcgctcggct    20460
tcgacgcggc cttctccgag ctgggcatgg cgctgctgtc cggcggtgcg ctggtcgtcg    20520
tcgaccagga gcggatcctg cccggacagc cgctggccga cgtgctggcc gagcaccggg    20580
tcacccatgt gacgctgccg cccagcgcgc tgtccgcgct gaccccgggg acgctgccga    20640
aggacctcac cctggtcgtg gccggcgagg cctgccccgc cgcggtggcc cgcacctggt    20700
ccgcccatca ccgcatgatc aacgcctacg gccccaccga gtccacggtc tgcgccagca    20760
tgagcgccgc gctgaccccg acaccgtcag cggcgactc ggtccccatc ggccgcccgc    20820
tctccggcgt ccgggtcagc gtcctggacg accggctgcg cccggtgccg gccggcgtcc    20880
ccggcgaggt gtatctctcc ggcgccgcgc tgcccgcgg ctacctcggg cggctcgcgc    20940
tgaccgcgga gcggttcgtc gccgacccgt acggtccgcc gggaagccgg atgtaccgca    21000
ccggcgaccg cgcccgctgg ctggccggcg gcgacctgga ctacctgggc cgcaccgacg    21060
accaggtcaa actgcgcggc ttccggatcg agctcggcga ggtcgaggcc gtactgtcgc    21120
gccacgacgg ggtcggcgcg gtggccgcca cggtgcacaa ggacgagcgg ggcacccgcc    21180
gcctggtggc gtacgtcgtc ccggcgcggg aggacgcggc cgacccggcg cggctgcgcg    21240
agttcgcccg cgaggtgctg cccgagcaca tggtgccctc ggtcttcgtg ccgctggacc    21300
ggctgccgct gaacgccaac ggcaaggtcg accggcgggc gctgcccgca cccgacatcc    21360
ggcgcgacga gggcagcgcc cgtatcgcgc gcgcaccccc ggcggaggag acgctggcgc    21420
gcatctggtc ggaggtgctg ggcgtcacgg acatcggcgt cgaggacaac ttcttcgacc    21480
tcggcggcga ctccatcctc agccttcagg tggtggcgcg ggcccgggcc gccggactgc    21540
ggctgaccgc caagcagacc ttcctgcggc agaccatcgc cgatctcgcc gccgacgccg    21600
tcgccgagac cgaccccgcc gcgcacggtg cggccaacga cggcccggtc accggcgagc    21660
tgccgctcac ccccatccag cactggttct tcaactccct cggcgacagc ctggagcagt    21720
tcaaccagtc gctgtatctg gagctggccg agggccccga cctcccggcg ctgcgcgccg    21780
cactggccgc gctgaccgaa cagcacgacg cactgcggct ccgcgccgta tccgaggacg    21840
ggcagtggcg gctgcaccac gcgcccgccg agaccggtca actcctcgaa cacctcgatc    21900
tgtccggcgt ctcgcccgac gagcaggacg ccgcgatggc ggccgccgtc gacgcggcgc    21960
agcgggactt ccggctgtcc gaggggccgt tgctgcgggc ccggctgttc accctcggcg    22020
acgcccggcc gccccggctg tacctcgtcg cgcaccacct cgtcatcgac ggcatgtcct    22080
ggcgcatcct gctggcggac ctggagaccg ctaccgcct ggcggcggac ggccggccga    22140
tcgacctggg gccccggacc acctcgttcc gcgactggtc gcgccggctg tcgcgccatg    22200
tcgcggacgg cggcctggac gccgaactgc cgtactggaa gggcgtacag gacgcggcgc    22260
gcgagaccgc cccgctcccc gtcgacaccg gcgggctccc cgaccccag ggcgcccagg    22320
aggagcccgg cgagaacacc gccgggtcgg cccgcaccgt ctccgtacag ctgtccgccg    22380
cgggcaccga ggcgctgctg cggcaggtgc ccgaggccta ccgcacccag atcaacgacg    22440
tcctgctcag cgcgctgggc cgggtgctga ccgactgggc gggcggcgag cgggtgctga    22500
tcgccctgga gggccacggc cgcgaggagc tcttcgacga ggtggacctc acccgcaccg    22560
tcggctggtt caccaccctc ttccgggtcg ccctgcggat gccggccgac cgggactggg    22620
gaacggtcct caagagcgtc aaggaacagc tgcgggcggt gccccacaac ggactcggcc    22680
atggcgcgct gcgtcatctg gcagggccca actcccctct ggaggacggt ccggagcccg    22740
```

```
aggtcagctt caactacctc ggccagctgg acgtgtccgc cgaccgcacc ggcctcgccc      22800
gcgccatgct caccagcgag ggcgccgagc gggccgccgg ccagcaccgt gcgcagctgc      22860
tggagatcaa cggcgtggtc accggcggcc ggctggagtt ccactggacg tactcggtga      22920
accggcaccg cgcagagacc gtcgaacggc tcgccgcggg cttcatgacc gcgctggaag      22980
cgatcgtggc gcactgcgcc gccccgggtt ccggcggcgc caccccgtcc gacttccgc       23040 tggccgccct cgaccaggcc accgtcgaca agatcgccgg cgacggccgc acggtcgagg      23100
acatctaccc gctcaccgcg atgcagagcg gcatgctctt ccacgcgctg agcgagtccg      23160
gacgcgaccc gtacaccggg cacttcggcg tccgcgtgga cggcatcacc gacccggggg      23220
cactggccgc ggcctggcag caggtcgtcg accggacccc cgccctgcgc accgccatcg      23280
tctggcagga cgtcgcggaa ccccttcagg tggtgcacgc ggccgcccgt gtgccggtca      23340
cccatcacga cctgcggtcc ctgaccgagc aggaacggca ggccgccctg accggctgt       23400 gggagcggcg cgaggagacc gtcatcgatc tcgccgtcgc gcccgcgctg cggctgaccc      23460
tcgtccggct caccgacagc gccgtccaga tgttctggac ctcgcaccac atcctgatgg      23520
acggctggag cttcgccggg ctgctgtcgg aggtgtgcgc ccagtacacc gcgctgaccg      23580
gcggcccccg cgtggcggcc ccggcccgcc gcccgtaccg cgactatgtc ggctggctgg      23640
ccgaacagga ccagccggcc gccgaggcgc actggcgctc ggtggtcgac gggttcacgg      23700
tgccgacgcc gctgccctac gaccggcagc cggtgaaggc acacggcacc cggtcctcgc      23760
gtgaggtgcg gctgcagctg tccgccgagc gctccgggcg gctgtccgag gccgcccggt      23820
cggcgcggct gaccgtcaac acgctggtgc agggcgcctg ggcgatcctg ctggcgcgct      23880
acggcggggt gcgcgacgtc tgcttcggca ccaccgtctc cggccgtccc gccaccctgc      23940
ccggcgccga gtcgatggcc gggctgttca tcaacaccgt gccggtacgg gcgaccatcg      24000
acggtgccgg tgccggcgac ggcgccgcca ccggcaccgt cgagtggctg cggcggctgc      24060
agagcgagca gctcgactcc cggcagcacg agcatgtctc gctggcgcag atccagcgct      24120
ggagcggcgt accggccggc accaacctct tcgacagcat cgtcgtcttc gagaactacc      24180
cctacgacag cgatgcggcc gccaagtacg ggctgaccct cggcacgttc cagggcgacg      24240
aggtcaccaa ctacgccctc accctgaccg cgtacgtggc cgacgagctg catctcaacc      24300
tcggctacga cccggatctg ttcgacgagg cgaccgtcga gcggatggcc gggcatctgg      24360
cgacgctgct cgacgccgtc gccgccgccc gcacaccccc ggtggacgac ctcccgctgc      24420
tcgatgcggc cgaacaccac cggcttctca ccgagtggaa cgacaccgcc gccggcttcc      24480
cgccgccgcg gccggtccat gagctcttcg ccgagcgggc cgcccgtacc ccggacgcgg      24540
tggcggtcag cgacgccacc cggcagctga ccttcgccga gctggagacc cgcgccaacc      24600
aactggcgca ccacctggcc ggtctgggcg tggcgcccgg cacgctggtc ggggtgtgcg      24660
ccgaccgcgg ggtggacgcc gtggtggcgc tgctgggcgt gctgcgggcc ggcggtgcct      24720
tcgtaccgct ggaccccgcc tatccggcgg agcggctcca ggtcatgctg gaggacgccg      24780
cggtgccggt cgtggtgacc gaggagcggc tgctggaccg gaccgccggg cacgacgcga      24840
cgacggtgtg cctggaccgc gatctgccgc tgctggagga gctgccggcc cgcccgccgt      24900
acaccgccgt ggcaccggac gacctggcgt atgtcgtcta tacgtcgggc accaccgggc      24960
gccccaaggg cgtgatggtc gagcaccggc acgtccacca catggtgcac gcctgggacc      25020
ggcgctacgg gctcgccgcg ctgcaaccgc gcgcgctgtc cgtctccagc atctccgtcg      25080
```

```
acctgttctt cagcgacttc ctgctctccg ccctcttcgg cggcacgatg gtgatctgtc   25140
cgcaggacgc cgtcgccgac caggtggcgc tgaccgatct gctgctcaag agccgggccc   25200
agctgatggt gacggtgccg acgctggccc gcgcggtggt cgccgagctc gcctggcgcg   25260
gtgtgacacc ggaggcgctg cgggtgctga tggtgggctc cgagggctgg ccggccgatg   25320
ccgcggccga gatcctggcc ggtctcgcgc cgggcacggt gctggtcaac gcgtacggat   25380
cgaccgagac cacggtcgac tccacggtct tccagctcgg ccgcgacccg ctgggcgacg   25440
ccgccttcgt accggtcggc aggccgctcg ccaacacccg gatctatgtg ctggacgagc   25500
ggatgcgccc ggttcccacc ggcgtcgtcg gcgagtgcta catcggcggc gacgagtgt   25560 cgcgcggcta tctgggccgc ccggagctga ccgccgagcg tttcctcgac gacccgttcg   25620
cgccggagcc gggcgcccgg atgtaccgga ccggtgacct cgcgcgctgg cgggccgacg   25680
gcaacctcga atgcctcggc cgggtcgacg accaggtcaa gatccgcggc ttccgggtgg   25740
aactcggcga ggtggaggcc gcgttggccc gccacccggc gatcgactcg gcggccgccg   25800
cgatccgcaa ggacgacggt gggccggccc gtctggtggg ctatgtcgtg cccgccgccg   25860
gccacacccc cgacctggcc gagctacggg ccttcgccgc cgaacggctg ccgtcgcccg   25920
ccgtccccac cgcgtacatg gtgctggacg cgctgccgat gacgccgagc ggcaccgtcg   25980
cccggcgtgc gctgccggcc ccggccgggg cgcaggacgc cgcccggccc tacaccgcgc   26040
cgggcagcgc caccgagctg ctgctctgcg gtatctggca ggaggtcctg ggcgtcgaac   26100
gggtcggcgt gcacgacaac ttcttcgacc tgggcggcga ctcgatcctc agcatccggg   26160
tcatctcccg gatccgggcc acgctggggcg tcgccccgtc gccccgccag ctcttcgaca   26220
ccccgacggt ggccggtctc gccgccaccc tcggccggga cgaccctcg gcggccgccg   26280 acgtcccccct ggagccggcc gaccgcggcg caccgctgcc gctgtcgtcc gcccagcaac   26340
gccagtggtt cctgcacaac ttcgacccgg acagcagcga gtaccacatc gtcaccgggc   26400
tccggctcga cggtgatctg gacgtcgcgg cgctgcgagg ggccctgaac gggctcgtcg   26460
cccggcacga ggcgctgcgt accacctacg cggccaccgg cgagggcgcc gagcagatcg   26520
tgcaccccgc gggcgaggtg gtctgcgagc gtacggatct gtccgaggtg cccgaggacc   26580
agcgcgagga caccctgcgc gggcacatcg accgcgccgc cgcccggccg ttcggcctca   26640
ccgagggccc ggtcctgcgc gccgaactgt tccggctcgg cgcccgtgac catctgctgc   26700
tgctcgtcat ccaccacatc gccaccgacg gtgtctcgat gcaggtgctc accgaggagc   26760
tcggcgtcca ctacgccgcg gcgctcgacg gcacaccgcc cgccctgccg gcgctgccgg   26820
tctcctacgc cgactacgcg gcctggcagc gccggatgct gtccggcccg cgctggacg   26880 gccatctcgc ctactggcag gagcggctgg ccggtgtccg gccgctggag ctgcccaccg   26940
accggccccg gccggcggtc cgcagctccg cgggccggat gctgctgatc gagatcgagc   27000
cgcgggtggc cgcgggcctc aaggaactgg cccgccgcca tgacgccacc ctgttcatgg   27060
cgctcaccgc ggcggtccag ctgctgctgg cccgctacac cggacagccg gacatcgtcg   27120
tgggcacccc ggccgccggc cggggccggc aagaactcga ggggctcgtc gggctgttcg   27180
tcaacacggt ggcgctgcgg tccaccgtcg acgagagcgg gaccttcgac gccttcctcg   27240
gtgcggtgcg cgacaccgtc ctcgaagcgt tgtgcacga ggacgtgccg ttcgaccggc   27300
tggtcgaggt gctgcgaccg cgccgcgacc ccagccgtaa cgcactggtg gaggtgttcg   27360
tcggactgga gacggaccgg tcggcgccgc cggcgctgcc cggactgacg gtgaccgagg   27420
tcccgttcgt cagcggcgag gtcagccatg acctcagctt cgacttcgtc gacgggcccg   27480
```

-continued

```
acggcctgaa ggcggccatc ggctacagca ccgcgctgtt cgacgacggc accgtcgagc   27540
ggatggccgg ccagttccag gcgctgctcg ccgcggtcct ggaggaccat cgcgcgctcg   27600
ccgacatcgc acccgcggac gaggccgagg tgcggcggct cgccgaactg cggcaggccg   27660
cgccctcgga gcccgacgcg tcggaaaccg acggcgcgcc ggccgcctac cgcgcgcccg   27720
ggaccgctgc cgagcgggcc ctggcggaga tctgggccgc cgtgctgggg gtgccgcggg   27780
tcgggaccga cgacaacttc ttccagctgg gcggcgactc cctgctcagc atccaggcgg   27840
tgcagcggat gcggcaggcc ggcctggcgg tgaccaccaa ggatctgttc gtccaccaga   27900
gcatcgcccc gctggcggcc ctcgccgagg aacgggcggc ggaccggccg gaggcccccc   27960
aggcgcagca cgacgatgcc gggacggcgg gcgagatacc gctcaccccg atccagcgcg   28020
actacttcgc ggccgggccg ctcgccccgc accacttcac ccagtcggtg ttcctcgaac   28080
tgcacgccga tctcgacgag ccggcgctgc ggcacgcact ggccgcgctg atcggccacc   28140
acgacgccct gcggacccgc ttcgtacgcg aagacggcga ctggcggcag tacgccaccc   28200
cgccggagcc ggtggacatc ctgcgccggc acgacctgtc cgggctgccg gaggctcaac   28260
gggccgccgc catggacgag ttggcggcct cggccgacgc cgggctcgat ctggcggccg   28320
ggccgccggc cgcggcgctg ctgttcgtct tcgggcccgg ggagcggccg gcgctgttcg   28380
tgaccgcgca ccatctcgtc gtcgacggcg tctcctggcg gatcctgctg gaggacctgg   28440
aagccggcta cgtccaggcc cgcgacggga agccggtgtc cctgggcgcc aaaagcacct   28500
cgttcgggca gtgggcgcac cggctcgccc ggcacatcgc cgacggcggc ctcgccgagc   28560
aggccgccta ctggcaggcg ctgcccgacg caccgaggt cccgcacgac ggctcggggc   28620
ccgcggtggt ggagtccgtg cagaccgtca cggtggagct gccggaggac accagcgagg   28680
tgctgctgcg ccggtccgcc ggggtcttcc ggacccgctt ccacgaggtg ctgttcgccg   28740
cgctcgccga caccctggcc cggtggacgg gcgaacgcca ggtcgtgttc gacaccgagg   28800
gccacggccg ggaggacctc ttcgacgacg tcgatctctc ccggaccgtc ggctggttca   28860
ccaccgagta ccccgtcgcc cttgaggtgg ccggcgaccg gacgactgg ccggcgctca   28920 tcaggtcggt acgcggacag ctgcggtcgc tgcccggcaa cggcttcggt tacggcgcgc   28980
tgcggcatct gagcccggcc ggcacccccgg gtgccgcact cgccgaacgg gccccggccc   29040
aggtggtgtt caactaccac ggccaggccg acgaggcgca gcgcgcggcg gagagcgacc   29100
tctaccacgc gttcggcgac ccgatcggcc gggagcagcg gcccgacgag ctgaccgggc   29160
acccggtgga ggtggtgggc gccgtgcact ccggcggct ccgcttcacc tggtacttct   29220
cgcgcaatgt tcatcacagg gccaccatcg acaaggtggc cgaggacttc gccgacgcgc   29280
tgcgcgccat cgcccggcac atcacggagc ggtgagccat ggaccacgaa agcctgcaca   29340
gcaccctgac cgaactggcg gcccgccatc gggtgcccgg cgcgcagctc gccgtcatcc   29400
acgaggggga acggttcctg gtgcacaccg gagtgtgtga caccgcctcc ggagcccccg   29460
tggagcggca caccgccttc cccgtcggct cgctgaccaa gccgttcacc gccgccctcg   29520
cgatgatcct ggtggccgac ggggacgtgg acctggacga gccgctgagg gggcagctgc   29580
cggagttcgg ggcgggcgaa ctcgtcaccc tccggcagtt gctcagccac acctcgggcc   29640
tgccctccga tgtgccggag ggcagcgacg aggccggcgg cggcgaccgt gcccgctggg   29700
tggcccggta ctgccgtacg gcggatctca cgcatgcgcc cgggacgtc ttctcgtact   29760 ccaacatcgg ctatgtcgtc gtgggccggc tcatcgaggc ggtcaccggc atgagctggc   29820
```

-continued

```
aggaggcgat cagcgcgatc ctgctcgaac ccctgggcac ccggcccgcg ttcgtcgtcg    29880 gagccccgc cacccgtccg gtggccaccg ggcacgccgt ccaggcggtc cgcgaccggg     29940
tggtgccgat accggaccag gatcttcccg aggtcgagat gcccaacggg gcgctggcgc    30000
tgagcgccga ggacctggtc ggcttcgccc ggctgtactt cgccggctgc ccggaccctc    30060
agccgctgga ccgggcgacc gccgacgaca tgtgcttcga ccagctggcc tcgatcgcca    30120
tcggcccgta cggcatggcc gacggctggg gcctgggctg ggcgaggttc gacgacggtg    30180
cggcggacgt ctacggccac aacggcaccg gcgacggcac ctcctgtcat ctgcgcttcg    30240
acccggccaa cggctccgcg gtcgcgctga ccgccaacgc caacaccggc gcccagctgt    30300
gggacgccct ggtgccccgg ctgcgggcca tgggtctggc ggtcggcgac cgcccggcgc    30360
ccgagccgcc caccaccccg ccgccggtcc cggacgactg tccgggccgc tacaccaacg    30420
gcgacaccga gttcgtggtg cagcccggcg ccgacggcgg gctgctgctg agcttcggcg    30480
gggcgccgca ctcggagctg ctgtgctccc ccgatctgcg cttcaccatg cgggagctgg    30540
gcagcggtgc ccggtccccg ggccgcttcg tgaccgatcc cgccaccggg cggatcggct    30600
acctccagat caccgggcga ctcgccccccc gacgctgaga cagggacggc ccccgggatg    30660
accacggccc ccacggacgc ggagacggca cgcggcagcg cggccgtccc gctgtcccgc    30720
aaccgcgact acaacatcct gtggtccagc cagctgatgt ccgaactcgc catggagatg    30780
gccgcggtag ccgtgccgct gctgatcctc gcccggcacg gctcaccgct ccagctgggc    30840
ctggcctcct ccgcgatggc ggccgcgcac atgatctcgg tggtgccggc cggggtgatc    30900
gcggaccgct gggaccgccg ccggctgatg ctgggctgcc aggtgctacg ggtgctgggc    30960
atggtgagcc tggccggcgc gctgctgctg gaccggtacg cgttctggca tgtgctgctg    31020
gtcgtggtgc tggagggctt cctcggctcg gtcttcgacc ccgcggaaca tgccgcgctg    31080
ccccaggtgg tgccgcccga ccagctctcc acggcggtgg ccagaaacgc ggcgcgcccc    31140
tacatcgcca ccctcgtggg gccgggcgtc gccggtttcc tcttcagcgc cctgccgctc    31200
gggccgttcg cgaccaatgc ggtgatgttc gcgctgtcgt ccgtggcgct gtgctttctg    31260
cggctgcccc gggggcggtc cgccgtggtc cggaccggcg acgggcccga cagcgccgga    31320
gcggaccacg acaggccgga ccacgacgga cgggacgacg cgaacgacga cactgcgccg    31380
cggcccgggg gcgccgccca ggacttcgct gccggcttcc gctgggtgct ggggcagccg    31440
gtgatccgca ccacgatggc ctggatgatg atcacgaacc tggtcttcag ctcgctgctg    31500
atcgtgctgc tcgcgctctc gggcgaggac aaggtcggcg ccggtgagct gggtctgacg    31560
atggcctgct tcggcgccgg cggactgctc ggcgggctct tcgcggcccg gatgcacgcc    31620
gccgcccggc caccggtgat cctcctcggc ttcacctgga ccgccgccct gggcgccgcc    31680
ctgatggcgg tggtgcccac cggtctgccc cagggagcgc tgctcggcct gatggcgctc    31740
ttcgccccgc tcgccaacac caccgtgctg acctaccagt tgaccgtcac cccggacgag    31800
ctgcggggcc ggatgagcgg cgtcgccggg ttctgctcgg ggggcgccgg tgtcctgggg    31860
cccgcgctcg gcggtgcgct gacggggggcg ccggcggggg gcgtgacccc cgtactcatc    31920
tgcgccggct gcctggtcct ggtcgctgtc gcggccaccg cgagcccccac gctgcggcgg    31980 tttcccgaca tcgcggaccg gcagcccctga cctgctgcga cacggcccgt gaccggccaa    32040
cttaactcca cagtcaagga catggaacgc ccggacgaat ccgacgatgc tcgtgtatca    32100 actgagatt tccgcgcgtc ctcggtgcgg gggctggtgc ctgtccggcg gtgtgccgcg    32160
cggtcggcga aggtcccgt atgcagaccc cccacacacc gagccaggca cagtcccagc    32220
```

```
cacggcaaaa gccgcagccg ccgtcgcagt cgcagtcgca gtcgcagccg aatctgaggt   32280
ccctgaccgg attacggttc ctgggcttat tacccgtctt cctcacccat gccgcgttcg   32340
agggcgtctt cagcgacgcg gacgtgagct ggggcttcct cgacgcgatg gggaacaccg   32400
gctatgccgc ggtctcgttc ttcttcgtgc tgagcggctt tgtgatcacc tggtcctacc   32460
gctcccgcga caccacccgc acgttctggc gccgacgcgc cttccgggtc ttccccaacc   32520
atctcgtggc ctatgtgttc gcgctggctc tgatgctcgc ggcgggcgcc gccttcgacg   32580
cccccgccct gatctcccag atgttcctgg tgcacgcatg ggtgcccgac ccgctgttca   32640
tcgacaccgg caacacggtg acctggtccc tcggggtcga tgtggtgttc tacgggctct   32700
tcccggtgct gctcgtgctg gtgaacaaga tcaagccaac ccgtttgtgg tactgggccg   32760
gtgctgccgt gctcatggtg atcgccatcc ccacagtggc gctgaccctg ctcccggaca   32820
ccccggccat gtcggtgggc gatgtctccc gcagccagta ctggttcacc tacttcttcc   32880
cgctctcccg aaccgtggag tgcgtgctgg gcatgctgat ggcgcggatc gtgctgtccg   32940
gcaagtggat aggcctgcgg gtgctgcccc cctcggccct ggtggtcgtg gggtatgtcg   33000
tcgcacagca actccccttc ctctaccggc tcagcgcggt gctgatcgtg ccgatcgtgc   33060
tgctcaccgc ctccgtggcg gtggccgacg ccgagggccg ggggacccccg ctcggcggca   33120 aggtcatggt ccggctcggt gaactctcct tcgccttcta cctcgtgcac caggcgctcc   33180
tggcgtacgg gcacatcctg atcagcccga agaacgccca gggcgaggtg ctgccccgta   33240
cctgggacac gcctggcggc atcgcggtga tcgtcctgtc gttcgtggtg tccctgggac   33300
tcgcgtggct gctgcacaac ggggtggaga gccggtgat cgccgttgg tcccggtcca   33360 ggcgccgcgt cacccagcag ccgccggcaa aggtgccggc aacttagctg cgaagtgaaa   33420
cgtgtggagt gcgcgaaaga tctcggccaa actccggcgc aacggggggag taaggctgac   33480 cgctgccaga agtccgcgcg cgccgtggat gtccggtgcc ggcgaccacg cccggatcat   33540
ccatcagccg acagtggtgc ggccgccgtt gcggcgcacc gagccgcacc gcctgtcgcg   33600
catctggcga gaggtccgca tgcagacaag acaatccaac ccgaacctga gatccctgac   33660
cggtttgcgg ttcgtggcga tgctgccggt cttcctcacc catgcggcgt tcgagggcgt   33720
cttcagcgac gcgaaggtga gctggggctt cctcgacgcg atggggagca ccggctatat   33780
ggccgtctcg ttcttcttcg tgctcagcgg cttttgtgatc acgtggtcgt accggcccac   33840
cgacaccgcg cgcaagttct ggcgccggcg cttcttccgg gtcttcccca accacgtcgt   33900
gacctatgcg ctcgccctcg ggctgatcgc tgcggtgggg ctgagtgtcg gcgtactgcc   33960
ctcggtcacc cagctcttcc tcgtccagtc ctgggtgccc gacccggcgt tcaccgacac   34020
cggcaacagc gtgagctggt cgctcgcggt ggatgtggtg ttctacgcgc tcttcccggt   34080
gctgctcacg ctggtgaaca agatcaagcc gaatcggctc tggtactggg tcggtggctc   34140
cgtcatcggt gtggccgtgg taccggccat cgcgctcgcc gcgctcccga gcacccccga   34200
gatgccgctc ggcggggtgt ccgtcagcca gtactggttc acctacttct tcccgctctt   34260
ccggctgctg gagtgtgtgc tcggcatgct gatggcgcgg atcgtgctgt ccggcaagtg   34320
gatacgcctg cgggtgctgc ccgccgcgt cctcgtggtg atcgcgtact acttcgccca   34380
gcaggtcccg tacctctacc ggctgagtgc ggtgacggtg ctgccggtcg cgctgctgac   34440
ggcggcggcc gcggtggcgg actccgaggg ccggggcacc ctgttcggca gcaaggtcat   34500
ggtctggttc ggcgaactct ccttcgcctt ctacctgctg cacaacctcg tcctgaagta   34560
```

```
cggccatctg ctgctcggcc acaccgagga ggagggcgag ctggtgggcc acacctgggg    34620
cgtgcccgag ggaatcgccc tgatcgccgc cgccttcgcg gtgtcccctgc tgctggcctg   34680 gctgctgcac aacggagtgg agaagcaggc gatgcgccgc tggtcccgac gcaagccggc    34740
tccagtggct gaagtaacca gtgggttcta tgcgaaggac ggggcaattt agctaggaag    34800
taaaggttat ggaacgggct gtcgaaagac ggcaagatct ccactgatca ggcgttcggc    34860
accggattcg atcaatcagg tgccctatct ggagggacgt gtacgtgctg acgctccacc    34920
tgcaggatga cgacgtcgcc gcgatcgacg ctgtggctga cgaactcagc cggcgatacg    34980
actccgtgga gtccacggag ttccaggccg agagccgcct ctacgcggac gagttgccac    35040
gtcgcgtgcg acgagcgctg cacgaatacc gcagcaccga aagtccggc atcctggtcg     35100 tcaccggcct gcccgtggac gactcggcgc tcggggcgac cccggccgac cgccggcaca    35160
agccggtgcc gtccacgtca ctgcgccagg acatcgcctt ctacctcata gccaatctgc    35220
tgggcgaccc catcggctgg gccacccagc aggacggctt catcatgcat gacgtctacc    35280
ccgtccaggg cttcgagcac gaacagatcg gctggggcag cgaggagacg ctcacctggc    35340
acaccgagga cgccttccat ccgctgcgca cggactatct cggactgatg tgtctgcgca    35400
atccggacgg cgtcgagacc accgcctgcg atatcgccga tgtcgagatc gacgacgaga    35460
cccgggagac cctctcgcag gagcgcttcc ggatcctgcc ggacgacgcg caccgcatcc    35520
acggcaaggc cccgggggac gagagcgcac gcgagagtgc gctgcgtgag cgcagccggc    35580
agcgggtggc ctcggccctg gagtcgcccg accggtggc cgtgctcttc ggggaccgcg    35640
acgacccgta tctgcggatc gacccgcact acatgcaggg cgtccagggc gagaccgagc    35700
agcgggcgct ggagaccatc ggcgccgcga tcgacgacgc catgtccggt gtcgtgctca    35760
gccccggtga catcgttttc atcgacaact accgcgtcgt ccacggacgt aagccgttcc    35820
gtgcccgctt cgacggtacg gaccgctggc tgcggcggct caacatcgcc cgggacctgc    35880
gcaagtcgcg cgaggccagg ctcgccgcca ccacccgcgt catctactga ccggctgccg    35940
ccgatcagtt agcgcaggca ccggccgaac caccgggcgc ctgcgcccag atcgcgccgc    36000
tcaacacacg gcaccgacgg ggaccgccgt catggcggtc ggccgctgtg tgcccatgcc    36060
ctcccgcatc tggggaaccc tttacgtctc tgcgaggtac ctgtgtccgg aacgcagcaa    36120
gtaaaagccg ctttggggga ttccgaaggt gacaccggaa acctcaccca actggagttc    36180
ctggctctga acagcgagtt caacatcgct gacggccacg cccggcaggc gctcacgccg    36240
ggccaaagca agatcgtcga cgatctgccg ctgctcttcg ccgagggcga gaagcggccc    36300
gtcgaagagc tcgaacgcga ggcgcaccac gccttcttca cctgcccctcg gccagcacag    36360 ctaccctcg gcccccggcc gggtgctgag ctgctactcc tcctcggtcg cgatggagat    36420
cctctcccgc tcgctgtccg agacgatcga gtcggtggcc ctggtccacc cgaccttcga    36480
caacatcgcc gacctgctgc gcggcaacgg cctgaagctg gtgccgctgg cggaggaccc    36540
gctgcacggc gacgacctcg acgtgagcct gctgaagtcg gtgggctgtg tcttcctcac    36600
cacgcccaac aaccccaccg gcaaggtcgt ctcccgggag cggctgaccc ggctggccga    36660
gcagtgcgcc gagcacggcg tcatcctcgc gctggacacg tccttccgcg gcttcgacac    36720
ccgcgcccac tacgaccact acgaggtgct caacgccagt ggtgtgcgct gggtggtgat    36780
cgaggacacc ggcaagctgt ggccgaccct cgacctcaag gtcggcatgc tcgtccactc    36840
cgagaacctc gcgctgccgg tcgagaagat ctactccgac atcctgctcg gtgtctcccc    36900
gctgatcctc gcgatggtcc gccgcttctc cgaggacgcc gcggccggcg gtctggagga    36960
```

```
tctgcaccgc ttcatcgccg ccaaccgtgc catggtgcgc gcggaactcg ccggtctgcc    37020
gggcgtcacg gtccccgacc ccgacagccg ggccagcgtc gagcgggtcg ccatcgatga    37080
cctgacgggc acgcaggtct gggcgaagct gcgggagcac aacgtctacg cgctcccgtg    37140
ccgcccgttc cactgggcca acccgtccga gggtgaccac accctgcggc tcgcgctggc    37200
ccggtccacg gacccgctcg cccagtccgt gcgcgcgcct gcgccacgtgc tgaaacagcg    37260
ttgatgacgc ctgtcgcaga aggaggactc ccgcacggct ccgtgccctc gctgtcgcac    37320
acgcggcagt ggcggcccgg ggtcgtgcag gaggtcgccc cggccggcgt cctcgacctg    37380
ggccccggct acatcgagcc ggcactcctg cccgtacgcc tgctgcgggg cgcgtacgag    37440
caagcgctgg cggagtacgg cgccgcggcg ctgggctacg gtcacgaccc gggcgcgcag    37500
ccgctgcgcg accggctggc cgcccgcgcc gccgcggcgg acggcctccc ctgcgacccg    37560
gaccaggtgc tgctgacctc cggcacgtcc caggccctct atctgctggc gacctcgctc    37620
gcggccccgg gcgacacagt gctgacggag gagctctgtt acgacctggg acagcggata    37680
ttccgggact gctcactgcg gctccgccag gtcgccatgg acgggtcggg gatgctgccc    37740
gacgcgctgg accgcgccct gaccgagggc gcgcagcgcg gcgcgaaaac cgctttcgtc    37800
tacctcaccc ccacccacca caaccccacg ggccacacga tgccgctggc gcgccgccgc    37860
ctgctgctcg aagtggccgc ccggcacgat gtgctgatcg tggaggacga cgcctacacg    37920
gaactgtccc tgatccctga ccgcactccc ccgccctcgc tggccgccct ggccggctac    37980
cggcgggtgg tgcggctgtg cagcttctcc aagaccctcg gccccggact gcggctgggc    38040
tggctgctcg ccgaccggga actggccggc cggctggcca cgcacggcct gttcgtcagc    38100
gggggttcgc tcaaccacac cacctcgctc gccgtgagca ccctgctcgc gagcggcgcg    38160
tacgaccgtc atctcgacgc gttccggggcg cagttgcgtg ctcgtaggga cgcgctcgtg    38220
ggcgctctac gcgcgatgct ggacgacggg gtggagctgc gcaccccgga gggcggattc    38280
ttcctgtggc tgcgggccgg ggacgggggcc gacgagcgtg agctgctcga cggcgccgcc    38340
cgggcgggcg tcaggatcgc cgccggatcg cgcttcggca caaccccaggg ggccggcttg    38400
cgcctggcct tcagcttcaa cccgcccgcg ttactggagc aggccgccaa gcggctgacc    38460
accgcatggt ccggcagcac gccggacctc gagatcggag tgagatcgtg acgaccagca    38520
ccgggaccaa cggccggcac acggtggccg gtccaggcag cgccggtccc gtcgggtaca    38580
gcctgccgct ctcgccgacg ggcgagtcgg cgatgctcac accaccgccg tggcacttct    38640
ccggcgaggt cgtcatggtc gactaccgcg tcgacccgga cgcggcccga cggttcctgc    38700
cgccgggcct ggagccgggt gccgaccccgg gcgccgcggc ggcggtgttc gcgacctggc    38760
agtggtgttc gcaggacgga gcggagctga ccgacccccgg tcgctgccag ttcggggagt    38820
tcctgatcct gctcagctgc gagttcgagg gccgtcccat ggcgcgctgc ccgtacgcct    38880
gggtggacca ggccgtgccc atgatgcgcg gctgggtgca ggggatgccc aagcagttcg    38940
gcgtgattca ccagagccgg cccgtcacgg tcggcaaggc gggctcccgg ctggcgcccg    39000
gcggtcgttt cgacggcgcg ctgtccgtgc acggacgacg cgtcgtggag gcctcggtca    39060
ccgtggacag gtcgacggac cagccgccgg cgctgcacga tgttccgcctg gcgcacaccc    39120
tggtgttccc ggagtgggtg ccctccggcg gcgggccgcg accacggctg gtcgcctccg    39180
aggtaagcga tgtggaattc tccccgatct ggaccggatc gggtgatctc acgttctttg    39240
acggactggg ggatgatttc ggggcgctcg caccgttgga agtaggtagc ggccacgtgt    39300
```

-continued

```
tctcgtacgg ggagaccttg cacggcggcc ggctgctcag cgactactcg gtatcagaac    39360
gacatcagcc atgaccacgg gggacaaagt gctgaggatc cacttcacag ttgaggacat    39420
agcaaatacg cgcatgctgg cgaccctcgg gccgctggcc gagagcgctt tcgcgctcta    39480
tctgttcggc cgtaacggcg atgtcgcctt tcacgagtgg cgtcgcagtg tccgcgccga    39540
actcggcaag gacgcggccc gcttcacggc cttgtcccag cagttccgga ccctggagga    39600
attacctgcc gccttcgccg acgccttcac gccggggggcg gaccccgacc aggttccgtc    39660
cggcgaggac cggcgcggcg ccaggctgct ggccgacctg tgccgggtgg ccgtgctgcc    39720
gcactggagc ctgatccgca gtcatctcga cggtgcgcgc gagggctggg gcagggtggc    39780
catctcgcac ggtgtcgagc ggctgctggg ctccgtgcac cccaaggtcc gctggcgggc    39840
gccggtcctc gaactgcggc acgggcccaa ccgcgacatc catctggacg gtcgcgggtt    39900
gctgctgtgc ccgtcgttct tcctgtcgga gcagtcctgt tcgttcgtga cggcggtcgg    39960
caaggacgcc atgcccgccc ttgtcttccc cgtgaaggcc tcgtccaggg tggacatctg    40020
gggtacctcg gaacacgacg agcaggcgct gggcgcactg gtcgggcaca ccaggcgcgc    40080
cgccctggaa gcgctcgccg agggctgctc cacgggcgaa ctcgccgacc ggctggggat    40140
ctcgctggcc ggtgccagca agcatgccgc ggtgctgcga cgatccgggc tggtgaccac    40200
ctcccgtaac cgcaacaccg cgctgcacgc gctcacccct ctgggcaccg ccctgctccg    40260
cagcagcgac cgcttcatct cgccgcctac cgccccggta tcgcgcgtgc cggcgcaacg    40320
catgcggccc ttgcagctca acggcatcgg ccccggcacc aaccgggcgg cggtctgacc    40380
gcccccgcgg acggccaccg ccacgactta cggcacccct gacaggagag gacacgacag    40440
tgggcacaaa ccccttcgac gaccccgacg gccggtatct ggtgctggtc aacgaggaag    40500
accagcattc actctggccg gctttcgccg aggtgcccca gggctggacg gtggcgctcg    40560
cggaaaccga ccgtcagtcc gcgctcgact tcatcaccga gcactggacc gacatgcggc    40620
cgcgcagcct ggtgcgggcg atggaagagg cttagaccag ccttgccgta tcaggcgatt    40680
tctccgggac cggcggttct ttctcaaaga tcgctgccgg ccccgggaa gaagcccca    40740
cccgccccg ccgtacggca gaattcctgc ccgtgactat tcgcttgctg atcgccgacg    40800
accaggagat ggtccgccgc ggaatacgcc gcatcgtgga gagccagccc gacatggaag    40860
tggtcggcga ggcggcaaac ggcgtggacg cggtggagat ggggcgcacg ctcaaacccg    40920
atgtggcgct ggtcgacatc cggatgccgc ggatggacgg cctggagtg acccgcctgc    40980
tggccgaccc cgccgcggcc aacccggtcc gggtcgtcgt ggtgacgacc ttcgacctgg    41040
acgagtacgt gtaccccgcg ctgcgcttcg gcgcctcggg gttcctgctc aagcgctcgg    41100
ggccgacgct gctggtcgag gcggtccggg cggcgatggc cggcgacagc ctgatcagcc    41160
cgtcgatcac tgtccggctg ctccagcatg tcaccggccc cacgaccggc cgccgccccc    41220
gccgccgtga ctcggtgctg accgagcggg aggtggagat cgccgggaag gtcgccgagg    41280
gcaagaccaa ttccgatatc gcccgcgagt tgttcatctc cgcgggcacg gtcaagaccc    41340
atgtcgcgag cattcagcga aagctacagg tacgcaatcg cgtcggggtc gcggtgcggg    41400
cctgggagct cggatatgcc accgggcaga ccccggggtg aaaacccgcg gccggcatcg    41460
ggcagcacgc caccccggcag aaaccccgat gccgtcccgc ggaaatctgc cgtccggcag    41520
atgcggtaat ttccgcgctg tgcttgccgc cgcgcaaccc ggggaatgtg cgtagcctcg    41580
ccctcatgga ttacgacgtt cctccccggc aaaagcgccg ccggtggtgc ggggtggccg    41640
cggcaatgat gctcgccccc gccgtcatag cgccaccgag cgcctatctg ctggcggtca    41700
```

```
tggccgcatt gacgctggcc gtatcgatac ttgcctggcc gaccggccgg atctccctgg    41760
cccaggcggc gggcggcgtc gcgctgctct ccctcgccgc ggacgtcggc tacttcgggc    41820
agcccggcct ggtgatcctc tggtacccgt tcgagacggt cgcgctgctc gttctcctgg    41880
agcgggtggt acgtcatgtg cccagccccc gggtgggcat cgtcgccccg ctgaccggcg    41940
cagccgtcat cctgctgccc ctgcgcttca ccctgcacgc ccccaccgcc gggctcaagg    42000
aatcggtctt cgcggccttg ctggccctga tcccggcggc ctgcgcgacg ggtgtgggc    42060 tctatctgcg gtcgctggac aaccgccggg cgtatgccgt ggtgctggcg cgccgtgaac    42120
agcgcctcga agtcgcccgc gatctgcatg acttcgtcgc ccacgaggtg accggcatcg    42180
ttctggaggc ccaggccgcc caagtcagcg aggacgccgg gcccgaggag caccgcgccc    42240
ttctgcagcg catcgagaag gccgggctac gggcgctgga ctccatggac cagacggtga    42300
cgacgctgcg cgaggcggac ggccgcaagt ggggcgagcc gccgcccacc cggctctacg    42360
gcttggccga cctccccgag ctcgtcggcc gcttctcctc catggccgcc gccgaggtgg    42420
cgctgtccct ggaggacgag gtcgccggca ccctctcgcg ggaggccgag gacaccgcgt    42480
accgggtggt acttgaatcg ttgaccaatg tccgtcggca tgcgccgcag gccggccggg    42540
tccaggtgtt cgccggacgg accgccgacc gggccgtgga ggtctcggtc gccgacaacg    42600
cagggccggg ggcgtccgcc ggcacccggc agggcggcgg tacgggcctg gcgggcctcg    42660
gcgaacgcgt cagcgccctg gcggctccc tggaggcggg cccgtacgag aacgggtggc    42720
gggtcaggtg cctgctgccg gcgcccgcca tccgctgagc ggatatctgc cgatcggcag    42780
atgtgccggc cgcccgggcc cgggatcctc ataggagtgc accacccgt gactctggag    42840 gaaccgatgt tctcaggcac catctcgaag cggcccgcca cactcgtcgt cgcggtggcg    42900
gccgtcgccg ccaccctcgg cctctccggc tgctccgtgg acgcctcgaa ggcgaagccc    42960
gaatcgaagt cgttcacgta ctcgggcaag tccctgaagg tgacgacgca cgaggtcgcc    43020
accaaggtgg tcgccgccga ccgcaaggac atcaaggtca cccgctggtt cgactcggcc    43080
gcgggcaccg agcacctgaa gtggaccctc aagggcgaca ccctggacat cgacgccggc    43140
tgcagcggta tcgcgatctg cgacgccaag ttcaaggtcg aggtccccaa gggcatcgcg    43200
gtgaccaagg acggcgagaa gaccgacctg accgggaaga gctgaccgtg ctcgacctcg    43260
tcaacatcac caaggtctac aagggcggca agcacgccgt ggacgacctg acgatgcgtc    43320
tggaacccgg catgctcggc ctgctgggcc caacggcgc cggcaagtcg tccctcatgc    43380
ggatcgcctc cacggtcacc cggcccacca gcggaaaggt cctcttccac ggagaggacg    43440
cggtcgccaa gcccaacgcg ctgcgccggg ccctcggtta cctcccgcag gacttcggcg    43500
tctacccgaa cctgacctcc cgcgagttcc tcaggtatct ggcggcggcc aagggcgtct    43560
cggccaagac cgccaaggcc cgtatcgatg agctcctgga gctcgtcaac ctcaccgaag    43620
cggtcaagcg tcccctgggc aagtactccg gcggcatgct gcgccgggtc ggcatcgccc    43680
aggtgctgct cgccgacccg caggtgatca tcgtggacga gccgaccgcg gggctggacc    43740
ccgaggagcg ggtcaggttc cgcaatctgc tcagcgatct ggcggccgac aaggtcgtga    43800
tgctctccac ccacatcgtc tccgacgtcg agtcggtggc ctccgacatc gcggtgatgg    43860
ccggcggccg gctgcagcgc cgcggcaccc ccgaggacct gctgcgctcg gtggacggcc    43920
aggtgtggga ggtgctggtc gacccctcgt ccgtagcggc ggtgcaggcg cagtacaccg    43980
tcagccgcct ggtccgcacg accgagggcg tccgtatccg gctgctctcg cgcgagctgc    44040
```

```
cgtacgaggg cgccgtccag ctgacgcccg acctggaaga cgcctacctc gccatcatcc   44100
gtggggtcga cggcggccgg gccgcccagg gcttcggcga acggccgctc caggcacggg   44160
tggtgtgagg caatgatgcg catgctcacc ggtcttgcgg tggccgactt ccgcgaccgg   44220
gtacgccggc ccgcgtatgt cgtgatcctg gccgcggccg tcgccctcgg ttacgtggcg   44280
gtgcccgact cggacgccaa atggatgatc atgcagatcg gtgatcaccg cgggatctac   44340
aacagcgcct acgtcggcat ggtgacgccc ctggccagcg gtctgtggat caccctcggc   44400
ggcttctaca tcgtccgcaa ctccatcgaa cgcgaccgca gcacccgcgt cggccagctg   44460
ctcgccgcca ccccgctgcg caccaccgcg tacatgctcg gcaagttcct cagcaacctc   44520
atgctgctgt cctccatgct cgtggtgctc gcgctcaccg ccctggtcat gcaactggcc   44580
cgcggcgagt cgcacgacat cgacctgatc gccctctggc agcccttcct cctcatcgcg   44640
ctgccgctgg tcgcgctgac cgccgccctc gcgctcctct tcgaatcgct gccgctgctg   44700
cgcaccggcc tgggcaacat cctgtggttc tgcatctgga tggtcgtctc gacggccggc   44760
cagggccccg gtctgcccct cgacggcatc ggcgtcaaca cgtcgtccg gtcgatgtat   44820 gacgacatgg tcgcccagca catcgatgtc accggcgcgt tcagcctcgg tctgacctac   44880
ctcgacaagc ccctcgggct cttcacctgg gacggcttca cgcccaccgc cggctatgtc   44940
ctcggccggg tgacgctgct gctgatcgcc gtcgtgatcg ccatgctccc cgcgctgtgg   45000
ttcggccgct tcgaccccgc gcgaacctgg ctgggccagg ggcgcacccc cgagcaggcc   45060
ccggccgacg tgtcgtcca gccggtcttc atcgacgagg tcggcccggg gacgcctccg   45120
ctgtccgttc agggccatgg gggagcttcc ccgtcccggc ccaccgtcgc cacgctgctg   45180 cgcaccgcc cggagccggg cgccgtgacc ctgcgcgtct gggccggcga ggtccgcatc   45240
ctgctgcaag gtgtgcgctg gtggtggtgg accggtgccg cattcctcat gatcgccgcg   45300
ctctcctccc cggggatcca cggcatcatc gcgtgatgc tgccgctgtc ctggatctgg   45360
ccggtgctga tctggtcgcg gctgggcacc cagcgccacg agtaccacgt cgacggcatg   45420
ctcggcgcct accccgcggt gcgccgccgg gtcttcgccg aatgggccgc gggcctgacc   45480
atcaccgccg tggccggcat cggtcccctg atccgcctgg tggccgccgc cgactggttc   45540
ggtctggccg gctgggtcgg cggggccctg ttcatcccgt ccctggccct caccctgggc   45600
acgctcagcc gtacccatcg cctcttccag gcggtctacc tgccgctctg gtacagcgtc   45660
gccaacggac tgccgatctt cgacttcatg ggcgcgctgc gcgacagcag cgaactggcc   45720
gccgtgcagc cgtcggtgac cgtcgtggtt ccgcgcgccc tgatgccat cgtcttcatg   45780 accggcgtac tccgccgctt cggccgcgac tgacccaccg accccgtcgg cgccgcggct   45840
gccgacgggt tcggggccgc gcggcaccgg tgccccgag agaggaacac gccatgaccg   45900
accccatccg aaccccgac acgtcgccg tcgaccacac ccggcacaca cggccgctgc   45960
aggccgagcg ccggatcgcg gaactggaaa acgagttgga cgagctgcgc agcgccaacg   46020
agatcctctt atcggtggcc acctacttcg gccaggccaa cgtcctgccc accggccgg   46080 ggataccccgg cccaccccgcc gccgagcgct gacgcccgac gtaagcgccc cggcacacac   46140
aaagccaacg ggggtgaagc accgactcga tccgaacaga cccgaggaac tcctatgcga   46200
ctgtggcccc ggcacaaagc cggccgaccc gaaaccgacc ggcacgaaac cgacccgcac   46260
acggccgagc agcacacggc cgacgcaccc gaggccggcc ggccgcacc cggccgcacc   46320 acgaaggga gcccgcgctc gctccccgcg acgatcgtca tgacgctgtc cgtgccctg   46380 gccgtgaccc tgaccgcggc gctgaccggg gcgttcgccc ccgcccgccc gtccctcagg   46440
```

-continued

```
agcgagaagg ccgccccgc cgcccccac tcccccagt ggacagccac ctggggagcc      46500
gccatgcagc aggcgacgaa cgaggccacg gaggacaccc cgaactggtc ccggcaggga   46560
ttcaagaacg agaccctgcg ccaggtgatc cggctcagcg tcggcggccc cgagctccgt   46620
atccgcctct ccaacgccta cggcaccaag cccctccaca tcgccggcgc caccgtcgcc   46680
aggtccgacg gcgaggccaa ggcgcgcccc ggcaccgtac gcaccctcac cttccgccat   46740
gcgcccgccc tcaccatccc cgcgggccgc gacaccgtca gcgacgcggt ggccatgccg   46800
accgccaacc tcgaaaaact caccgtcacc ctgcgcttca ccgcccccac cggcccggcc   46860
accatgcacc gcttcaccac ggccacgtcc taccgcgccc ccggcgaccg gctacgcagc   46920
cccgccgccg atgacttcaa ccgccgtgcc tcgcacgcct ggtactacct gacggccgtc   46980
gatgtgaccc aggagccgcc ccgttcggcc gactccctca tggtcttcgg cgactccctc   47040
atggacggcg tcggcaccag ccccgacacc gacaaccgct ctccgacaa  actcgccgaa   47100
cgcctcatcg ccgccggccg ccccagggga atgaccaacg ccggcctggc gggtgaccc    47160
ctgctgcacg attcccctg  cttcggcgag aagggcaccg cccgcttcgc caaggaactg   47220
cgcgatcgcg ccgccctgcg caccgtcttc atccacctcg gcgccaatga cctcgcccag   47280
tcccagcagg acgaccctg  caccaggaac cgcccccgg  tgaccgccca acagctcatc   47340
gacggccacc gcgccctggt ccgcgcggcc cacgcccgcg tatcaaggc  catcggtgtg   47400
acgatcctcc ccctcaggag cgccgtcttc cccttcacca ccccgccgg  tgacaagatc   47460
cgccggcagc tcaaccactg gatccgcacc agccacacct cgacgccgt  cctcgacgcc   47520
gaccgcgtcc tgaccgaccc cgcgaaccccc aaccgccccc ccccggcta catctcccag   47580
gacggcctcc accccagcga cgccggctac ctggccctcg cctccgccgt cgacctgaac   47640
gccctctgac cccactcccc ccaccccag  acagccccga ccaggtgccc ccgtccctg    47700
gtcgggcgc  acgtccgtca cgagggcaac gtccgtctgt acgcgggcga gtgcggcccc   47760
gaggcagaag tgcgggccgt gtgcgaagtc ctggccggcc tcgccgagcg caccccccag   47820
ccgccgcccc cggcgtccgg ccgcaccgcc caggaagccc tgggcgcgtt cgcccgcgca   47880
tgggtcgccc ggctcccgct cgccaccgat gagcaccggg cggccgggat cggcatggtc   47940
ctgatgccgg agatcctcgc cgacgcacga accgcctgc  cgttcgccca actgatgaag   48000
ctcaacgcga tcctgctcgg actcgccccg gagcgtctgc accggcccga gcctccgcc    48060
ccccgcctgg tacgcgtcgc ggaagccacc tcaccaccct gcacgcgcg  agccaactgg   48120
ccgacgccgc acccggcttc accgaaccct tcgacatcgt cagcgcctgc gagcggctga   48180
ccggcctcga tctgggcgac                                               48200
```

<210> SEQ ID NO 2
<211> LENGTH: 2747
<212> TYPE: PRT
<213> ORGANISM: Streptomyces hygroscopicus

<400> SEQUENCE: 2

```
Met Gly Glu Trp Arg Asp Arg Arg Leu Asp Glu Leu Phe Ala Glu Gln
1               5                   10                  15

Ala Ala Arg Thr Pro Glu Arg Thr Ala Val Val Phe Glu Gly Arg Ala
            20                  25                  30

Val Ser Tyr Arg Glu Leu Asp Ala Arg Ala Glu Arg Leu Ala Ala Val
        35                  40                  45

Leu Ala Gly Arg Gly Ala Gly Pro Glu Arg Phe Ile Ala Leu Leu Leu
```

-continued

```
                50                  55                  60
Pro Arg Ser Ala Glu Leu Ile Val Ala Ile Leu Ala Val Leu Lys Ser
 65                  70                  75                  80

Gly Ala Gly Tyr Ile Pro Ile Asp Pro Glu Tyr Pro Ala Asp Arg Ile
                 85                  90                  95

Ala Tyr Ile Leu Gly Asp Ala Arg Pro Val Ala Thr Ile Thr Thr Ala
                100                 105                 110

Glu Val Arg Asp Gly Leu Pro Asp Pro Asp Thr Gly Ser Gly Thr Asp
                115                 120                 125

Trp Leu Ile Leu Asp Glu Ser Gly Tyr Glu Gln Glu Pro Ala Gly Ala
130                 135                 140

Arg Pro Gln Pro Ala Pro Ala Pro Arg Ser Ala Glu Asn Pro Ala
145                 150                 155                 160

Tyr Val Ile Tyr Thr Ser Gly Ser Thr Gly Arg Pro Lys Gly Val Val
                165                 170                 175

Ile Pro His Ser Asn Val Gly Arg Leu Leu Ser Ser Thr Ala His Trp
                180                 185                 190

Tyr Gly Phe Asp Glu Gln Asp Val Trp Pro Leu Phe His Ser Phe Ala
                195                 200                 205

Phe Asp Val Ser Val Trp Glu Ile Trp Gly Ala Leu Leu His Gly Gly
                210                 215                 220

Lys Leu Val Val Val Pro His Ala Val Thr Arg Ala Pro Ala Asp Phe
225                 230                 235                 240

Leu Arg Leu Leu Val Glu Glu Arg Val Thr Val Leu Asn Gln Thr Pro
                245                 250                 255

Ser Ala Phe Tyr Gln Leu Met Ala Ala Asp Arg Glu Asn Pro Ala Leu
                260                 265                 270

Gly Ala Gln Leu Ala Leu Arg Tyr Val Val Phe Ala Gly Glu Ala Leu
                275                 280                 285

Asp Leu Gly Lys Leu Ala Asp Trp Tyr Glu Arg His Asp Asp Arg Ala
                290                 295                 300

Pro Thr Leu Val Asn Met Tyr Gly Ile Thr Glu Thr Thr Val His Ser
305                 310                 315                 320

Ser Phe Leu Ala Leu Asp Lys Glu Gly Ala Ala Gly Ala Thr Gly Ser
                325                 330                 335

Ala Val Gly Val Ala Leu Pro Asp Leu Thr Phe His Val Leu Asp Glu
                340                 345                 350

Asp Leu Arg Pro Val Pro Val Gly Ala Glu Gly Glu Leu Tyr Val Ala
                355                 360                 365

Gly Pro Gly Leu Ala Arg Asn Tyr Ala Gly Arg Pro Gly Leu Thr Ala
                370                 375                 380

Glu Arg Phe Val Ala Cys Pro Phe Gly Pro Pro Gly Ala Arg Met Tyr
385                 390                 395                 400

Arg Ser Gly Asp Leu Val Arg Pro Leu Pro Asp Gly Leu Glu Tyr
                405                 410                 415

Leu Arg Arg Ser Asp Asp Gln Val Lys Ile Arg Gly Phe Arg Ile Glu
                420                 425                 430

Leu Gly Glu Ile Ser His Ala Leu Ala Gln Asp Pro Ser Val Asp Gln
                435                 440                 445

Ala Thr Val Val Val Arg Asp Glu Ala Ser Gly Glu Arg Arg Leu Val
                450                 455                 460

Ala Tyr Val Val Pro Ala Gly Ser Ala Arg Pro Thr Pro Ser Arg Leu
465                 470                 475                 480
```

-continued

```
Arg Ala Ala Leu Ala Thr Arg Leu Pro Gly Tyr Met Val Pro Thr Ala
                485                 490                 495
Phe His Val Met Pro Ala Phe Pro Leu Thr Ala Asn Gly Lys Leu Asp
                500                 505                 510
Arg Arg Ala Leu Pro Ala Pro Thr Arg Gln Asp Ser Val Asp Ala Asp
                515                 520                 525
Tyr Ala Ala Pro Glu Gly Ala Thr Glu Ala Leu Ala Ala Ile Trp
            530                 535                 540
Arg Glu Val Leu Gly Val Glu Gln Ile Gly Ala Asp Asp Phe Phe
545                 550                 555                 560
Glu Leu Gly Gly Asp Ser Leu Ser Val Val Arg Ala Leu Ser Arg Met
                565                 570                 575
Arg Thr Gly Leu Gly Leu Arg Leu Thr Ala Ala Glu Phe Phe Ala Thr
                580                 585                 590
Pro Thr Val Arg Ala Leu Ala Ala Arg Glu Arg Gly Thr Ile Gly
            595                 600                 605
Ala Pro Glu Gln Ile Pro Ala Ala Pro Arg Thr Gly Ala Leu Pro Leu
            610                 615                 620
Ser Phe Thr Gln Gln Arg Phe Trp Leu Phe His Glu Leu Asp Pro Gly
625                 630                 635                 640
Glu Val Glu Tyr Asn Val His Ser Ala Leu Arg Leu Arg Gly Thr Leu
                645                 650                 655
Asp Leu Pro Ala Leu Arg Thr Ala Leu Gly Gly Leu Ile Ala Arg His
                660                 665                 670
Glu Pro Leu Arg Thr Thr Val Val Ser Asp Asp Gly Arg Pro Thr Ala
                675                 680                 685
Val Ile Ala Pro Pro Glu Gly Phe Pro Val Pro Leu Thr Val Glu Asp
            690                 695                 700
Leu Ser Ala Leu Thr Gly Asp Asp Gln Glu Ala Ala Gln Arg Arg Leu
705                 710                 715                 720
Leu Ala Glu Glu Val Ala Arg Pro Phe Asp Leu Ala Ala Gly Pro Val
                725                 730                 735
Leu Arg Val Leu Val Ile Arg Arg Gly Glu Arg Asp His Ala Leu Val
                740                 745                 750
Ile Gly Val His His Leu Ala Thr Asp Gly Trp Ser Met Gly Leu Leu
                755                 760                 765
Thr Asp Glu Leu Ser Ala Arg Tyr Asp Ala Ala Arg Arg Gly Val Pro
770                 775                 780
Ala Ala Leu Glu Pro Leu Pro Val His Tyr Ser Asp Tyr Ala Ala Trp
785                 790                 795                 800
Gln Arg Ala Thr Val Asp Asp Gly Arg Leu Val Pro Gln Ile Asp Tyr
                805                 810                 815
Trp Arg Asp Arg Leu Ala Asp Val Ala Pro Leu Gln Leu Pro Thr Asp
                820                 825                 830
Arg Pro Arg Pro Ala Leu Lys Thr Ser Ala Gly Ala Ala His Arg Phe
                835                 840                 845
Thr Leu Asp Arg Arg Leu Val Ala Ala Leu Lys Glu Leu Ser Ala Ala
            850                 855                 860
His Gly Ala Thr Leu Phe Met Thr Leu Thr Ala Ala Leu Gln Val Leu
865                 870                 875                 880
Leu Ala Arg Tyr Ser Gly Gln Gln Asp Ile Ala Leu Gly Thr Ala Val
                885                 890                 895
```

```
Ser Gly Arg Asp His Pro Gln Val Glu Arg Leu Val Gly Ala Phe Ile
            900                 905                 910

Asn Thr Val Val Leu Arg Ser Asp Val Arg Gly Glu Leu Pro Phe His
        915                 920                 925

Glu Phe Leu Gly Glu Val Arg Glu Thr Val Leu Gly Ala Phe Ala His
    930                 935                 940

Gln Asp Leu Pro Phe Asp Arg Leu Val Asp Ala Leu Gly Ala Glu Arg
945                 950                 955                 960

Asp Pro Ser Arg Thr Pro Leu Val Gln Ala Met Leu Leu Gln Asn
                965                 970                 975

Ala Pro Ala Gly Ala Glu Phe Ala Gly Leu Arg Thr Glu Thr Val
            980                 985                 990

Ala Leu Pro Arg Pro Ala Ala Ile Phe Asp Leu Thr Val Asp Cys Thr
        995                 1000                1005

Glu Arg Ala Gly Ala Leu Glu Val Met Val Glu Tyr Asn Thr Asp
    1010                1015                1020

Leu Phe Asp Ala Thr Thr Ile Glu Arg Leu Ser Gly His Leu Arg
    1025                1030                1035

Val Leu Leu Asp Ala Val Cys Ala Ala Pro Arg Arg Gln Val Arg
    1040                1045                1050

Asp Leu Pro Leu Leu Pro Ala Ala Glu Arg Asp Thr Leu Leu Thr
    1055                1060                1065

Gly Trp Asn Asp Thr Ala Ala Ala Leu Pro Thr Thr Leu Gly Val
    1070                1075                1080

His Arg Gln Phe Ala Glu Arg Ala Arg Thr Thr Pro Asp Ala Leu
    1085                1090                1095

Ala Val Thr His Cys Gly Gln Thr Leu Thr Tyr Ala Gln Leu Asp
    1100                1105                1110

Ala Arg Ala Asn Gln Leu Ala His Tyr Leu Gly Ala Leu Gly Val
    1115                1120                1125

Gly Arg Gly Thr Pro Val Val Leu Asn Leu Ala Arg Lys Pro Gln
    1130                1135                1140

Leu Ile Val Ala Met Leu Ala Val Leu Lys Ala Gly Gly Ala Tyr
    1145                1150                1155

Val Pro Thr Ala Leu Asp Thr Pro Ala Ala Arg Leu Gly His Leu
    1160                1165                1170

Leu Glu Glu Thr Gly Thr Pro Val Leu Leu Thr Thr Ala Arg Gln
    1175                1180                1185

Ala Gly Ala Leu Pro Pro Thr Glu Ala Ser Val Ile Asp Leu Asp
    1190                1195                1200

Ala Ala Gly Pro Asp Ile Ala Arg His Pro Glu His Asp Pro Gln
    1205                1210                1215

Val Ala Thr Arg Pro Glu Asp Leu Ala Tyr Ile Val Tyr Thr Ser
    1220                1225                1230

Gly Ser Thr Gly Arg Pro Lys Gly Val Ala Val Pro His Ser Ala
    1235                1240                1245

Leu Thr Asp Tyr Cys Ala Trp His Asn Asp Ala Leu Asp Val Gly
    1250                1255                1260

Pro Glu Asp Arg Gly Ser Ser Val Val Gly Leu Ala Phe Asp Val
    1265                1270                1275

Ala Val Gly Glu Val Trp Pro Tyr Leu Cys Ala Gly Ala Arg Val
    1280                1285                1290

Asp Gln Pro Asp Gln Glu Thr Leu Asp Asp Pro Thr Ala Leu Val
```

-continued

```
             1295                1300                1305
Glu  Trp  Phe  Ala  Glu  Asn  Gly  Thr  Thr  Val  Ala  Tyr  Leu  Pro  Thr
             1310                1315                1320

Pro  Arg  Ile  Glu  Ser  Leu  Leu  Asp  Val  Ala  Ala  Ile  Thr  Thr  Thr
             1325                1330                1335

Arg  Leu  Arg  Thr  Val  Leu  Val  Ile  Gly  Asp  Ser  Leu  Arg  Arg  Arg
             1340                1345                1350

Pro  Gln  Pro  Gly  Leu  Pro  Phe  Thr  Leu  Leu  Asn  Ala  Tyr  Gly  Pro
             1355                1360                1365

Ala  Glu  Ala  Thr  Val  Ala  Ala  Thr  Gln  Ala  Val  Val  Glu  Pro  Leu
             1370                1375                1380

Gly  Pro  Asp  Ala  Pro  Ala  Gly  Leu  Pro  Ser  Ile  Gly  Ala  Pro  Leu
             1385                1390                1395

Tyr  Asn  Thr  Ala  Ala  Tyr  Val  Leu  Asp  Asp  Arg  Leu  Cys  Pro  Val
             1400                1405                1410

Pro  Val  Gly  Val  Pro  Gly  Glu  Leu  Tyr  Leu  Ala  Gly  Ala  Gly  Leu
             1415                1420                1425

Ala  Gln  Gly  Tyr  Gln  Gly  Arg  Pro  Asp  Leu  Thr  Ala  Glu  Arg  Phe
             1430                1435                1440

Val  Gly  Cys  Pro  Phe  Gly  Pro  Pro  Gly  Thr  Arg  Met  Tyr  Arg  Thr
             1445                1450                1455

Gly  Asp  Ile  Val  Arg  Trp  Leu  Pro  Asp  Gly  Thr  Leu  Asp  Phe  Leu
             1460                1465                1470

Gly  Arg  Ile  Asp  Asn  Gln  Val  Lys  Leu  Arg  Gly  Tyr  Arg  Ile  Glu
             1475                1480                1485

Leu  Gly  Glu  Ile  Glu  Ser  Val  Leu  Ala  Arg  Arg  Glu  Glu  Leu  Ser
             1490                1495                1500

Gln  Val  Phe  Val  Thr  Val  Arg  Glu  Pro  Ser  Pro  Gly  Arg  Arg  Ser
             1505                1510                1515

Leu  Val  Ala  Tyr  Leu  Val  Ala  Asp  Arg  Gly  Thr  Ala  Pro  Asp  Pro
             1520                1525                1530

Glu  Glu  Leu  Ala  Gly  Tyr  Ile  Ala  Ser  Val  Leu  Pro  Glu  Tyr  Met
             1535                1540                1545

Val  Pro  Ser  Ser  Phe  Val  Leu  Leu  Asp  Ala  Leu  Pro  Leu  Thr  Ala
             1550                1555                1560

Asn  Gly  Lys  Ile  Asp  Arg  Arg  Ala  Leu  Pro  Glu  Pro  Glu  Pro  Ala
             1565                1570                1575

Gly  Gly  Glu  Gly  Ala  Ala  Tyr  Val  Ala  Pro  Gly  Asn  Glu  Val  Glu
             1580                1585                1590

Glu  Thr  Leu  Ala  Ala  Ile  Trp  Ala  Glu  Val  Leu  Gly  Val  Glu  Arg
             1595                1600                1605

Val  Gly  Val  Gln  Asp  Asn  Phe  Phe  Ala  Leu  Gly  Gly  Asp  Ser  Ile
             1610                1615                1620

Ser  Gly  Leu  Gln  Thr  Ala  Val  Arg  Ala  Arg  Arg  Ala  Gly  Leu  Arg
             1625                1630                1635

Leu  Ala  Ser  Lys  Asp  Leu  Phe  Gln  Arg  Gln  Thr  Ile  Ala  Ala  Leu
             1640                1645                1650

Ser  Pro  Val  Val  Thr  Val  Glu  Arg  Thr  Thr  Ala  Asp  Ala  Asp  Pro
             1655                1660                1665

Ala  Pro  Ser  Asp  Arg  Pro  Thr  Ala  Pro  Phe  Ala  Leu  Ser  Gly  Leu
             1670                1675                1680

Asp  Arg  Val  Gly  Val  Glu  Arg  Leu  Thr  Ala  Asp  Gly  Gly  Pro  Ala
             1685                1690                1695
```

-continued

```
Glu Asp Ala Tyr Pro Leu Thr Pro Met Gln Ser Gly Leu Leu Phe
    1700                1705                1710

His Thr Leu Met His Ala Glu Arg Gly Met Tyr Ile Glu Gln Phe
    1715                1720                1725

His Phe Ala Leu His Ser Ile Arg Glu Pro Glu Leu Leu Ala Thr
    1730                1735                1740

Ala Trp Gln Arg Val Val Asp Arg Thr Pro Val Leu Arg Thr Ser
    1745                1750                1755

Leu Ala Trp Asp Gly Leu Ala Glu Pro Leu Gln Val Val Arg Thr
    1760                1765                1770

Gly Val Arg Ile Pro Val Ala Gln Leu Asp Trp Thr Ala Leu Asp
    1775                1780                1785

Glu Ala Gly Gln Arg Gln Ala Leu Glu Arg Tyr Leu Thr Glu Asp
    1790                1795                1800

Arg Thr Arg Gly Leu Asp Leu His Thr Ala Pro Leu Ala Arg Ile
    1805                1810                1815

Ala Val Ala Arg Leu Gly Gly Asp Gln Val Arg Leu Val Trp Thr
    1820                1825                1830

Phe His His Leu Leu Leu Asp Gly Trp Ser Val Val Gln Val Leu
    1835                1840                1845

Ser Glu Val Leu Gly Glu Tyr Ala Ala Leu Ala Asp Gly Ile Pro
    1850                1855                1860

Tyr Thr Pro Gln Leu Arg His Thr Tyr Ala Glu Phe Val Gly Gln
    1865                1870                1875

Leu Ala Gly Gln Asp His Thr Ala Ala Glu Lys Tyr Trp Arg Ala
    1880                1885                1890

Ala Leu Thr Gly Arg Glu Ser Pro Thr Pro Leu Pro Tyr Asp Arg
    1895                1900                1905

Pro Arg Pro Asp Ala His Gln Ala Ala Pro Asp Ala Glu Leu Lys
    1910                1915                1920

Leu Arg Leu Pro Ala Ala Val Thr Gly Arg Leu Gly Thr Ala Ala
    1925                1930                1935

Lys Arg Ala Gly Val Thr Met Asn Thr Val Val Gln Gly Leu Trp
    1940                1945                1950

Ala Leu Leu Leu Ala Arg His Ser Gly Glu Arg Asp Val Leu Phe
    1955                1960                1965

Gly Ala Thr Val Ala Gly Arg Pro Asp Asp Leu Ala Gly Ala Glu
    1970                1975                1980

Ser Val Ile Gly Leu Phe Ile Asn Thr Leu Pro Val Arg Val Asp
    1985                1990                1995

Val Asp Pro Asp Ala Gly Leu Leu Ser Trp Leu Arg Arg Val Gln
    2000                2005                2010

Asp Glu Gln Ala Glu Ala Arg Ala His Glu Gln Val Ser Leu Ala
    2015                2020                2025

Gln Val Gln Gly Trp Ala Pro Glu Arg Ala His Gly Gly Leu Phe
    2030                2035                2040

Asp Ser Val Leu Ala Phe Glu Asn Phe Pro Ala Asp Leu Gly Pro
    2045                2050                2055

Ala Gly Asn Tyr Gly Leu Arg Leu Asp Ala Ile Glu Ala Ser Asn
    2060                2065                2070

Thr Ser Asn Tyr Pro Leu Asn Ala Ile Val Gln Leu Asn Glu Glu
    2075                2080                2085
```

-continued

```
Leu Thr Val Leu Leu Arg Tyr Asp Thr Ala Leu Phe Asp Ala Asp
    2090              2095              2100

Thr Val Ala Arg Leu Ala Gly His Leu His Thr Leu Leu Glu Glu
    2105              2110              2115

Thr Ala Glu Asn Pro Asp Arg Arg Val Gly Glu Leu Pro Leu Leu
    2120              2125              2130

Thr Ala Ala Glu Arg His Thr Ile Val His Thr Trp Thr Asp Thr
    2135              2140              2145

Ala Ser Asp Tyr Ser Val Asp Arg Arg Leu Asp Ala Val Ile Ala
    2150              2155              2160

Glu Gln Ala Ala Ala Arg Pro Thr Ala Ile Ala Val Val Asp Gly
    2165              2170              2175

Glu Arg Gln Leu Ser Tyr Gly Glu Leu Asp Arg Arg Ala Asn Gln
    2180              2185              2190

Leu Ala His His Leu Arg Ala Ala Gly Val Gly Arg Asp Ala Leu
    2195              2200              2205

Val Gly Ile Ala Val Glu Arg Ser Ala Glu Val Val Val Ala Ile
    2210              2215              2220

Leu Gly Thr Leu Lys Ala Gly Ala Ala Tyr Val Pro Leu Asp Pro
    2225              2230              2235

Glu Phe Pro Ala Gln Arg Leu Ala Thr Met Leu Ser Glu Ser Arg
    2240              2245              2250

Pro Ala Val Leu Leu Thr Gln Glu His Leu Leu Ala Gly Leu Pro
    2255              2260              2265

Pro Thr Asp Ala Arg Val Val Cys Val Asp Arg Asp Leu Ala Ala
    2270              2275              2280

Ile Glu Ala His Pro Thr Ala Ala Pro Val Ser Gly Gly Asp Ala
    2285              2290              2295

Gly Asp Leu Ala Tyr Val Thr Tyr Thr Ser Gly Ser Thr Gly Arg
    2300              2305              2310

Pro Lys Gly Val Met Val Glu His Arg Ser Leu Phe Asn Ile Ile
    2315              2320              2325

Thr Glu Ala Gly Arg Leu Tyr Asp Leu Gly Pro Asp Ser Arg Met
    2330              2335              2340

Leu Gln Phe Tyr Thr Met Ser Phe Asp Gly Gly Val Trp Glu Val
    2345              2350              2355

Phe Leu Thr Leu Thr Ala Gly Ala Thr Leu Val Ile Ala Asp Pro
    2360              2365              2370

Glu Ala Arg Gln Ser Pro Ala His Leu Ala Glu Gln Leu Arg Ala
    2375              2380              2385

Glu Ser Ile Thr Ala Leu Thr Leu Pro Pro Ala Val Ala Ser Val
    2390              2395              2400

Leu Asp Ala Ala Ser Leu Pro Gly Ile Arg Ser Leu Gly Leu Ala
    2405              2410              2415

Gly Asp Val Leu Ala Pro Glu Leu Ala Arg Glu Trp Ala Arg Gly
    2420              2425              2430

Arg Arg Leu Phe Asn Ile Tyr Gly Pro Ser Glu Ala Thr Leu Ser
    2435              2440              2445

Val Ala Leu His Arg Val Asp Pro Gly Ala Ala Gly Arg Gln Val
    2450              2455              2460

Pro Leu Gly Pro Pro Val Pro Asn Thr Arg Phe His Val Leu Asp
    2465              2470              2475

Glu Arg Leu Ala Val Val Pro Val Gly Val Thr Gly Glu Leu Tyr
```

-continued

```
                2480                2485                2490
     Ile Gly Gly Ala Gly Leu Ala Arg Gly Tyr Leu Gly Arg Pro Asp
     2495                2500                2505

Leu Thr Ala Gln Arg Phe Val Ala Asp Pro Phe Gly Pro Pro Gly
     2510                2515                2520

Ser Arg Leu Tyr Arg Thr Gly Asp Leu Ile Arg Trp Thr Pro Gln
     2525                2530                2535

Gly Arg Leu Glu Phe Ala Gly Arg Val Asp Asn Gln Val Lys Ile
     2540                2545                2550

Arg Gly Tyr Arg Val Glu Pro Ala Glu Val Glu Ser Ala Leu Leu
     2555                2560                2565

Arg Gln Pro Gly Val Ala Glu Ala Val Val Ile Ala Arg Asp Asp
     2570                2575                2580

Asp Thr Gly His Lys Arg Leu Val Ala Tyr Val Val Pro Asp Gly
     2585                2590                2595

Ser Gly Thr Ala Pro Glu Arg Ala Ala Leu Leu Arg Ala Leu Gly
     2600                2605                2610

Gly Gln Leu Pro Gly Tyr Met Val Pro Ser Ala Leu Val Thr Leu
     2615                2620                2625

Pro Glu Leu Pro Leu Gly Pro Thr Gly Lys Val Asp Val Arg Ala
     2630                2635                2640

Leu Pro Ala Pro Asp Pro Ala Ala Gly Gly Thr Ala Asp Arg Ile
     2645                2650                2655

Pro Pro Arg Thr Pro Thr Glu Glu Ala Leu Ala Leu Ile Trp Val
     2660                2665                2670

Glu Leu Leu Gly Leu Glu His Val Gly Val Glu Asp Asn Phe Phe
     2675                2680                2685

Asp Leu Gly Gly Asp Ser Ile Thr Ser Leu Arg Leu Met Ser Arg
     2690                2695                2700

Met Gly Gly Ala Phe Gly Val Asp Val Ser Pro Arg Asp Phe Phe
     2705                2710                2715

Asp Ala Pro Thr Ile Ala Ala Leu Ala Glu Arg Leu Glu Glu Lys
     2720                2725                2730

Ile Leu Ala Gln Leu Glu Glu Ala Val Gly Gly Gly Ala Leu
     2735                2740                2745

<210> SEQ ID NO 3
<211> LENGTH: 8244
<212> TYPE: DNA
<213> ORGANISM: Streptomyces hygroscopicus

<400> SEQUENCE: 3
atgggtgagt ggcgcgatcg ccgcctggac gaattgttcg ccgagcaggc cgcgagaaca       60
ccggagcgta ccgcggtggt cttcgagggc cgggcggtga gttatcggga actcgacgcc      120
cgcgccgagc ggctggccgc tgtgctggcc ggccgcggcg cgggacccga gcggttcatc      180
gcgctgctgc tgccccgctc cgccgaactg atcgtggcca tcctcgccgt actgaagtcc      240
ggcgccggat acatcccgat cgacccggag taccggccg accgcatcgc ctacatcctc      300
ggcgacgcgc gccggtggc gacgatcacc accgccgagg tgcgggacgg tctgccggac      360
ccggacaccg gctccgggac cgactggctg atcctggacg agtccgggta cgagcaggag      420
ccggccgggg cgcgcccgca gcccgccccg gccgccccgc ggtccgcgga gaaccccgcc      480
tacgtcatct acacctccgg ctcgaccggc cggcccaagg gcgtggtgat cccgcacagc      540
```

```
aatgtgggac ggctgctgtc gtccaccgcc cactggtacg gcttcgacga gcaggacgtc     600
tggccgctgt tccactcctt cgccttcgat gtctcggtct gggagatctg gggcgcgctg     660
ctgcacggcg gcaagctggt cgtcgtcccg catgccgtca cccgcgcccc ggccgacttc     720
ctgcggctgc tggtcgagga acgggtcacc gtcctgaacc agacgccttc ggcgttctac     780
cagctgatgg ccgccgaccg ggagaacccc gcgctcggcg cccaactcgc cctgcgttat     840
gtggtgttcg cgggtgaggc gctggacctg ggcaagctcg ccgactggta cgagcggcac     900
gatgaccggg cgccgacgct ggtcaacatg tacggcatca ccgagaccac cgtgcactcc     960
tcgttcctcg cactggacaa ggagggcgcg gccggcgcca cgggcagcgc cgtcggcgtc    1020
gccctccccg acctgacctt ccatgtcctc gacgaggacc tgcggcccgt cccggtcggc    1080
gcggagggcg agctgtatgt ggccgggccc ggctggcac ggaactacgc gggccggccg     1140
gggctgaccg cggagcgctt cgtggcctgc ccgttcggcc cgcccggggc ccgtatgtac    1200
cgctcgggcg acctggtgcg gccgctgccg gacggcggcc tcgaatacct gcggcgcagc    1260
gacgaccagg tcaagatccg cggtttccgg atcgaactgg gtgagatctc gcacgcactg    1320
gcccaggacc cctcggtcga ccaggccacg gtggtggtcc gcgacgaggc gtcgggcgag    1380
cgcaggctgg tggcgtacgt cgttccggcc ggctccgccc gtcccacccc gtcccggctg    1440
cgtgccgcgc tggccacccg cctgcccggc tacatggtcc ccaccgcctt ccacgtcatg    1500
ccggccttcc cgctgaccgc caacggcaag ctggaccgca gggcgctgcc cgcgcccacc    1560
cgccaggaca cgtcgacgc cgactacgcc gcccccgagg cgccaccga ggaggcgctg      1620 gccgccatct ggcgcgaggt gctcggcgtc gaacagatcg gtgccgacga cgacttcttc    1680
gagctcggcg gtgactcgct gtccgtggtg cgggcgctgt cgcggatgcg gaccggcctg    1740
gggctgcgcc tgacggccgc ggagttcttc gccacccca ccgtccgggc actggccgcg     1800
cgccgcgagc ggggcacgat cggcgcgccg gagcagatac cggccgcgcc gcgtaccggc    1860
gcgctgccgc tgtccttcac ccagcagcgg ttctggctct tccacgaact cgaccccggc    1920
gaggtcgagt acaacgtcca ctccgcgctg cggctgcgcg gcaccctcga cctccccgcg    1980
ctgcgcaccg cgctcggcgg gctgatcgcc cgccatgagc cgctgcggac gaccgtggtc    2040
tccgacgacg gccgccccac cgcggtcatc gccccgcccg agggcttccc ggtcccgctc    2100
accgtcgagg atctctccgc gctgaccggc gacgaccagg aggccgccca gcggcgactg    2160
ctggccgagg aggtcgcccg gcccttcgac ctggccgccg gccggtgct gcgggtgctg     2220 gtgatccgcc gcggcgagcg cgatcacgcc ctggtgatcg gggtgcatca cctcgccacc    2280
gacggctggt cgatggggct gctcaccgac gagctgagcg cgcgctacga cgccgcgcgc    2340
cgcggggtgc cgccgcgct ggagccgctg ccggtccact acagcgacta cgccgcctgg     2400
cagcgcgcca ccgtgacga cggccggctg gtgccccaga tcgactactg gcgcgaccgg    2460
ctggcggatg tggcaccgct gcaactgccc accgaccggc cccggccgc gctgaagacc     2520 tcggccggtg cggcgcaccg cttcaccctc gaccgccggc tggtcgccgc cctcaaggag    2580
ctgagcgccc ccatggcgc cacgctcttc atgaccctga ccgccgcgtt gcaggtgctg    2640
ctcgcccgct actccggaca gcaggacatc gcgctgggca ccgccgtctc cggccgggac    2700
cacccgcagg tggagcggct ggtcggcgcg ttcatcaaca ccgtggtgct ccgctccgac    2760
gtgcgcggcg agctgcccct ccacgaattc ctcggggagg tacgggagac ggtgctgggc    2820
gccttcgcgc accaggacct tccgttcgac cggctcgtgg acgcgctggg cgccgagcgc    2880 gaccccgagcc gtacccgct ggtccaggcg atgctgctgc tgcagaacgc cccggccggt    2940
```

-continued

```
gcggaggagt tcgccgggct gcgcaccgag accgtcgcgc tgccgcgccc ggccgcgatc      3000
ttcgacctga cggtggactg cacggagcgg gccggggcgc tggaggtgat ggtcgagtac      3060
aacaccgatc tgttcgacgc gacgaccatc gagcggctct cgggccatct gcgggtgctg      3120
ctggacgccg tatgcgcggc accgcggcgc caggtgcgcg atctgccgct gctgccggcg      3180
gccgaacgcg acacgctgct gaccggctgg aacgacaccg ccgccgcact gccgacgacg      3240
ctcggggtgc accgccagtt cgccgagcgg gcccgcacca ccccggacgc gctcgccgtc      3300
acacactgcg gacagaccct cacctacgcc caactcgacg cgcgcgccaa ccagttggcg      3360
cactacctgg gcgctctcgg cgtcggccgg ggcaccccg tggtgctgaa cctggcgcgc      3420
aagccgcagc tgatcgtggc gatgctcgcg gtgctcaagg ccggcggcgc gtacgtaccg      3480
accgcgctgg acaccccggc ggcacggctc gggcatctcc tggaggagac cggcaccccc      3540
gtgctgctga ccaccgcgcg gcaggccgga gcgctgcccc cgaccgaggc gagcgtcatc      3600
gacctcgacg cggccgggcc ggacatcgcc cggcatccgg agcacgaccc ccaggtggcg      3660
acccggcccg aggacctcgc gtacatcgtc tacacctccg ggtccaccgg ccgccccaag      3720
ggcgtcgcgg tgccgcacag cgcgctgacc gactactgcg cctggcacaa cgacgcgctg      3780
gacgtcggcc ccgaggaccg cgggtcgtcc gtggtcggcc tggccttcga cgtcgcggtc      3840
ggcgaggtgt ggccgtatct gtgcgcgggc gcccgcgtgg accagcccga ccaggagacg      3900
ctggacgatc cgacggcgct ggtggagtgg ttcgccgaga acggcaccac ggtcgcctat      3960
ctgccgaccc cgcgcatcga atccctgctg gacgtagcgg cgatcaccac cacccggctg      4020
cgcaccgtcc tggtcatcgg cgactcgctg cgccgcaggc cgcagcccgg actgccgttc      4080
accctgctca acgcctacgg gcccgcgag gcgacggtgg ccgccacca gcggtggtc      4140 gagcccctgg gacccgacgc gcccgccggg ctgccgtcca tcggcgcccc gctgtacaac      4200
accgccgcct atgtcctcga cgaccggctg tgcccggtcc ccgtcgggt gcccggcgag      4260 ctgtacctcg ccggcgcggg tctggcgcag ggctatcagg gccgcccga cctgaccgcg      4320 gagcgcttcg tcggctgccc cttcgggccg cccggaaccc ggatgtaccg cacgggtgac      4380
atcgtgcgat ggctaccgga cggcaccctg gacttcctcg gccggatcga caaccaggtc      4440
aaactgcgcg gctaccgcat cgaactcggc gagatcgaga gcgtgctggc ccgccgcgag      4500
gagctctcgc aggtgttcgt cacggtccgc gagccgtccc ccggccgccg gtccctggtc      4560
gcctacctcg tcgccgaccg gggcaccgcg cccgacccgg aggagctcgc cggatacatc      4620
gcctccgtac tcccggagta catggttccg tcctccttcg tactgctcga cgcgctgccg      4680
ctgaccgcga acggcaagat cgaccggcgg gcgctgcccg agccggagcc ggccggcggc      4740
gagggcgccg cgtatgtcgc gcccggcaac gaggtcgagg agaccctggc cgccatctgg      4800
gccgaggtgc tcgcgtcga acgggtcggc gtgcaggaca acttcttcgc cctcggcggc      4860
gactcgatca gcggtctgca gaccgccgta cgggcccgcc gggccgggct gcgactggcc      4920
tccaaggacc tcttccagcg ccagaccatc gcggcgctga gccccgtggt gacggtggag      4980
cggaccacgg cggacgccga ccccgcaccg tccgaccggc cgaccgcgcc gttcgcgctc      5040
agcggtctgg accgggtcgg tgtggagcgg ctgaccgcgg acggcggccc ggccgaggac      5100
gcctacccgc tgacccccgat gcagagcggg ctgctcttcc acaccctgat gcacgccgaa      5160
cgcggcatgt acatcgagca gttccacttc gccctgcaca gcatccgcga gccggagctg      5220
ctggccaccg cctggcagcg ggtcgtcgac cgcaccccctg tgctccgtac gtcactggcc      5280
```

```
tgggacggcc tcgccgaacc gctccaggtc gtgcgcaccg gcgtccggat accggtggca    5340
cagctcgact ggacggcact ggacgaggcc ggacagcggc aggccctgga gcggtatctg    5400
accgaggacc gcacgcgcgg gctcgatctg cacaccgcgc cactcgcccg gatcgccgtc    5460
gcccgcctgg gcggcgacca ggtccggctg gtgtggacgt tccaccatct gctgctggac    5520
ggctggagcg tcgtacaggt gctgtccgag gtgctcggcg agtacgccgc gctcgccgac    5580
ggcatcccgt acaccccgca actgcggcac acctacgccg agttcgtcgg ccagctggcg    5640
gggcaggacc acaccgccgc cgagaagtac tggcgtgccg cgctcaccgg ccgtgagtcg    5700 cccacccgc tgccgtacga ccggccgcgc cccgacgccc atcaggccgc ccccgacgcc    5760
gagctgaagc tgcggctgcc ggccgcggtg accggccgac tgggcaccgc ggcgaagcgg    5820
gccggggtga cgatgaacac cgtggtgcag ggcttgtggg cgctgctgct ggcccgccac    5880
agcggtgagc gggacgtact gttcggcgcc acggtcgccg gcggcccga cgatctggcg    5940 ggcgcggaat cggtgatcgg cctgttcatc aacacccttc cggtgcgcgt cgacgtcgat    6000
ccggacgccg gtctgctgag ctggctgcgc cgggtgcagg acgagcaggc cgaggcgcgc    6060
gcccatgagc aggtctcgct cgcccaggtc cagggctggg cgccggagcg ggcgcacggc    6120
ggactgttcg acagcgtgct ggccttcgag aacttcccgg ccgacctcgg tcccgccggg    6180
aactacgggc tgcggctcga cgccatcgag gccagcaaca cctccaacta cccgctcaac    6240
gccatcgttc agctcaacga agagctgacc gtgctgctgc gctacgacac cgcgctgttc    6300
gacgcggaca ccgtggcgcg gctggccggc catctgcaca cgctgctgga ggagaccgcc    6360 gagaacccg accgccgggt cggcgagctg cccctgctca ccgccgccga gcggcacacc    6420
atcgtgcaca cctggaccga caccgcctcg gactactcgg tcgaccgccg gctggacgcg    6480
gtcatcgccg aacaggccgc ggcccggccg accgcgatcg ccgtcgtcga cggtgaacgg    6540
cagctgagtt acgcgagtt ggaccgccgc gccaaccagc tggcacacca tctgcgcgcc    6600
gcgggcgtgg gccgggacgc cctcgtcggg atcgccgtcg agcgcagcgc ggaggtcgtc    6660
gtggccatcc tcggcacgct caaggcgggc gccgcgtatg tgccgctcga ccccgaattc    6720
cccgcgcagc ggctcgccac catgctgtcc gagtcccggc ccgcggtcct gctcacccag    6780
gaacacctgc tggcgggct gccgccgacg gacgcccggg tggtgtgcgt ggaccgggac    6840
ctggcggcca tcgaggcgca ccccaccgcc gcgccggtct ccggcggcga cgccggcgac    6900
ctggcctatg tcacctacac ctcgggctcc accggccgcc caagggcgt catggtcgag    6960 caccgctcgc tgttcaacat catcaccgag gccgacggc tctacgacct gggccccgac    7020
agccggatgc tgcagttcta cacaatgagc ttcgacggcg gcgtctggga ggtcttcctg    7080
acgctgaccc ccggcgccac cctcgtcatc gcggaccccg aggcccgcca gagcccggcc    7140
cacctcgccg agcagctgcg cgcggagtcg atcaccgcgc tgacgctgcc gcccgcggtg    7200
gcctcggtgc tggacgcggc ctcgctgccc ggcatacgca gctgggggct cgccggggat    7260
gtgctcgcgc ccgaactcgc ccgggagtgg gcgcgggggc gccggctgtt caacatctac    7320
gggcccagca aggcgaccct gtccgtcgcc ctgcaccgcg tcgacccgg ggccgccggg    7380 cgccaggtgc cgctcggacc gccggtgccc aacacccgtt tccatgtgct cgacgagcgg    7440
ctggccgtgt tccggtcgg ggtgaccggc gagctctaca tcggcggtgc gggcctggcc    7500
cgcggctacc tgggccgccc cgacctgacc gcgcagcgct tcgtcgccga cccgttcgga    7560
ccgccgggat cccgtctcta ccgcaccggt gacctgatcc gctggacccc gcaggggcgg    7620
ctggagttcg ccgggcgggt ggacaaccag gtcaagatcc gcggctaccg tgtcgagccc    7680
```

-continued

```
gccgaggtgg agagcgcact gctgcggcag cccggcgtcg cggaggcggt ggtgatcgcc      7740
cgggacgacg acaccggcca aagcggctg gtcgcctatg tcgtaccgga cgggagcgga      7800
accgccccgg aacgcgccgc cctgctgcgc gccctgggcg ccaactccc cggctacatg      7860 gtgccgtcgg ccctcgtcac cctgcccgag ctaccgctcg gaccgaccgg caaggtcgat      7920
gtgcgggcgc tgccggcacc ggatccggcc gccggcggca ccgccgaccg catcccgccc      7980
cgcaccccca cggaagaggc actggccctc atctgggtgg agctgctcgg gctcgaacac      8040
gtcggcgtcg aggacaactt cttcgacctc ggcggcgact ccatcaccag cctgcggttg      8100
atgtcgcgga tgggcggcgc gttcggtgtg gacgtctcac cccgcgactt cttcgacgcc      8160
cccaccatcg ccgcccttgc cgagcgccta gaggaaaaga tcctggcgca gttggaagaa      8220
gccgtcggag gcggcgccct atga                                            8244
```

<210> SEQ ID NO 4
<211> LENGTH: 3668
<212> TYPE: PRT
<213> ORGANISM: Streptomyces hygroscopicus

<400> SEQUENCE: 4

```
Met Thr Ser Ser Ala Ala Asp Gln Pro Asp Asn Pro Asn Thr Thr Thr
1               5                   10                  15

Pro Ala Ser Arg Ala Glu Arg Thr Ala Ala Leu Pro Ala His Val Gln
                20                  25                  30

Glu Leu Leu Arg Ala Arg Leu Ala Gly Arg Ala Ala Thr Gly Gly
        35                  40                  45

Ala Asp Thr Ile Pro Arg Ile Gly His Asp Gly Pro Val Ala Leu Ser
    50                  55                  60

Pro Ala Gln Glu Arg Leu Trp Tyr Leu His Glu Leu Glu Pro Glu Ser
65                  70                  75                  80

Asn Glu Tyr Asn Thr Leu Arg Val Leu Arg Leu Arg Gly Asp Leu Asp
                85                  90                  95

Pro Gly Ala Leu Ser Ala Leu Ser Glu Ile Val Ala Arg His Gly
            100                 105                 110

Ala Leu Arg Thr Thr Phe Gly Ser Arg Glu Gly His Ala Glu Gln Thr
        115                 120                 125

Val His Pro Val Pro Thr Pro Leu Pro Leu Val Asp Leu Ser Ala
    130                 135                 140

Ala Asp Asp Gly Glu Arg Asp Ala Leu Arg Thr Leu Leu Gln Tyr
145                 150                 155                 160

Glu Ala Arg Arg Pro Phe Asp Leu Arg Arg Gly Pro Val Leu Arg Ala
                165                 170                 175

Gln Leu Ile Arg Leu Ala Ala Asp His Val Leu Ala Leu Ala Leu
            180                 185                 190

His His Ile Val Thr Asp Gly Trp Ser Met Gly Val Leu Thr Gly Glu
        195                 200                 205

Leu Thr Ala His Tyr Ala Ala Thr Leu Arg Gly Ala Pro Ala Val Leu
    210                 215                 220

Pro Glu Leu Pro Val Ser Tyr Leu Asp Val Ala Val Trp Gln Arg Asp
225                 230                 235                 240

Gln Leu Ser Ser Ala Arg Leu Arg Glu Gly Leu Asp His Trp Arg Arg
                245                 250                 255

Glu Leu Ala Gly Leu Val Pro Leu Asp Leu Pro Thr Thr Trp Gln Arg
            260                 265                 270
```

```
Pro Pro Val Arg Thr Ser Ala Gly Ala Leu His Ser Phe Glu Ile Pro
        275                 280                 285

Pro Ala Val Ala Ala Arg Leu Arg Glu Leu Gly Arg Glu Gln Gly Ala
    290                 295                 300

Thr Leu Phe Met Ala Leu Val Ala Ala Val Gln Leu Leu Leu Ser Arg
305                 310                 315                 320

Trp Ser Gly Gln Arg Asp Ile Ala Val Gly Thr Ala Ala Ala Gly Arg
                325                 330                 335

Gly Arg Thr Glu Thr Glu Asn Leu Ile Gly Phe Phe Val Asn Asn Leu
            340                 345                 350

Val Leu Arg Ser Arg Ile Asp Glu Thr Arg Ser Phe Thr Glu Leu Leu
        355                 360                 365

Arg Ala Val Arg Ala Thr Val Leu Asp Ala Phe Ala His Glu Asp Val
        370                 375                 380

Pro Phe Gln Arg Val Val Glu Ala Leu His Pro Glu Arg Asp Leu Ser
385                 390                 395                 400

Arg Pro Pro Leu Ala Glu Val Ala Val Asn Leu His Asn Thr Pro Arg
                405                 410                 415

Thr Asp Thr Glu Leu Pro Gly Leu Arg Ile Glu Glu Met Pro Pro Pro
            420                 425                 430

Val Phe Ala Ser Ser Met Asp Leu Ser Phe Asp Phe Thr Glu Arg Asp
        435                 440                 445

Asp Arg Leu Glu Gly His Leu Thr Tyr Asn Thr Asp Leu Phe Ala Ala
    450                 455                 460

Asp Ala Ala Ala Arg Met Ala Ala Gln Leu Val Thr Leu Leu Glu Asp
465                 470                 475                 480

Leu Thr Arg Arg Pro Ala Val Pro Val Ala Gly Leu Ala Val Leu Pro
                485                 490                 495

Ala Ala Glu His Arg Arg Val Thr Glu Glu Trp Pro His Ser Gly Pro
            500                 505                 510

Gly Arg Glu Pro Arg Thr Ala Pro Glu Leu Phe Ala Ala Gln Val Ala
        515                 520                 525

Arg Thr Pro Asp Ala Asp Ala Leu Val Ser Asp Glu Glu Thr Leu Ser
    530                 535                 540

Tyr Ala Glu Leu Asp Gly Arg Ile Asn Gln Trp Ala Arg Leu Leu Leu
545                 550                 555                 560

Ala Arg Gly Ala Gly Pro Glu Thr Leu Val Ala Val Ala Leu Pro Arg
                565                 570                 575

Ser Ala Gln Met Val Thr Ala Ile Leu Ala Ile Gln Lys Thr Gly Ala
            580                 585                 590

Ala Tyr Leu Pro Leu Asp Pro Lys Ser Pro Ala Glu Arg Asn Arg Leu
        595                 600                 605

Met Ile Glu Asp Ala Arg Pro Leu Leu Val Leu Thr Ser Ala Gly Phe
    610                 615                 620

Gly Asp Gly Ala Glu Leu Gly Ala Pro Ala Leu Phe Leu Asp Asp Pro
625                 630                 635                 640

Asp Thr Arg Ala Ala Ala Gly Glu Leu Ser Ala Gly Pro Leu Ala Ala
                645                 650                 655

Ala Glu Leu Pro Ala Pro Leu Leu Pro Gly His Pro Ala Tyr Val Ile
            660                 665                 670

Tyr Thr Ser Gly Ser Thr Gly Arg Pro Lys Gly Val Val Val Thr His
        675                 680                 685
```

-continued

```
Thr Gly Val His Gly Leu Val Ala Ala Gln Ser Ala His Phe Arg Thr
690                 695                 700
Gly His Gly Ala Arg Val Leu Ser Phe Ala Ser Leu Gly Phe Asp Ala
705                 710                 715                 720
Ala Phe Ser Glu Leu Gly Met Ala Leu Leu Ser Gly Gly Ala Leu Val
                725                 730                 735
Val Val Asp Gln Glu Arg Ile Leu Pro Gly Gln Pro Leu Ala Asp Val
                740                 745                 750
Leu Ala Glu His Arg Val Thr His Val Thr Leu Pro Pro Ser Ala Leu
                755                 760                 765
Ser Ala Leu Thr Pro Gly Thr Leu Pro Lys Asp Leu Thr Leu Val Val
                770                 775                 780
Ala Gly Glu Ala Cys Pro Pro Ala Val Ala Arg Thr Trp Ser Ala His
785                 790                 795                 800
His Arg Met Ile Asn Ala Tyr Gly Pro Thr Glu Ser Thr Val Cys Ala
                805                 810                 815
Ser Met Ser Ala Ala Leu Thr Pro Asp Thr Val Ser Gly Asp Ser Val
                820                 825                 830
Pro Ile Gly Arg Pro Leu Ser Gly Val Arg Val Ser Val Leu Asp Asp
                835                 840                 845
Arg Leu Arg Pro Val Pro Ala Gly Val Pro Gly Glu Val Tyr Leu Ser
850                 855                 860
Gly Ala Ala Leu Ala Arg Gly Tyr Leu Gly Arg Leu Ala Leu Thr Ala
865                 870                 875                 880
Glu Arg Phe Val Ala Asp Pro Tyr Gly Pro Pro Gly Ser Arg Met Tyr
                885                 890                 895
Arg Thr Gly Asp Arg Ala Arg Trp Leu Ala Gly Asp Leu Asp Tyr
                900                 905                 910
Leu Gly Arg Thr Asp Asp Gln Val Lys Leu Arg Gly Phe Arg Ile Glu
                915                 920                 925
Leu Gly Glu Val Glu Ala Val Leu Ser Arg His Asp Gly Val Gly Ala
930                 935                 940
Val Ala Ala Thr Val His Lys Asp Glu Arg Gly Thr Arg Arg Leu Val
945                 950                 955                 960
Ala Tyr Val Val Pro Ala Arg Glu Asp Ala Ala Asp Pro Ala Arg Leu
                965                 970                 975
Arg Glu Phe Ala Arg Glu Val Leu Pro Glu His Met Val Pro Ser Val
                980                 985                 990
Phe Val Pro Leu Asp Arg Leu Pro Leu Asn Ala Asn Gly Lys Val Asp
                995                 1000                1005
Arg Arg Ala Leu Pro Ala Pro Asp Ile Arg Arg Asp Glu Gly Ser
        1010                1015                1020
Ala Arg Ile Ala Pro Arg Thr Pro Ala Glu Glu Thr Leu Ala Arg
        1025                1030                1035
Ile Trp Ser Glu Val Leu Gly Val Thr Asp Ile Gly Val Glu Asp
        1040                1045                1050
Asn Phe Phe Asp Leu Gly Gly Asp Ser Ile Leu Ser Leu Gln Val
        1055                1060                1065
Val Ala Arg Ala Arg Ala Ala Gly Leu Arg Leu Thr Ala Lys Gln
        1070                1075                1080
Thr Phe Leu Arg Gln Thr Ile Ala Asp Leu Ala Ala Asp Ala Val
        1085                1090                1095
Ala Glu Thr Asp Pro Ala Ala His Gly Ala Ala Asn Asp Gly Pro
```

-continued

```
              1100                1105                1110
Val Thr Gly Glu Leu Pro Leu Thr Pro Ile Gln His Trp Phe Phe
    1115                1120                1125
Asn Ser Leu Gly Asp Ser Leu Glu Gln Phe Asn Gln Ser Leu Tyr
    1130                1135                1140
Leu Glu Leu Ala Glu Gly Pro Asp Leu Pro Ala Leu Arg Ala Ala
    1145                1150                1155
Leu Ala Ala Leu Thr Glu Gln His Asp Ala Leu Arg Leu Arg Ala
    1160                1165                1170
Val Ser Glu Asp Gly Gln Trp Arg Leu His His Ala Pro Ala Glu
    1175                1180                1185
Thr Gly Gln Leu Leu Glu His Leu Asp Leu Ser Gly Val Ser Pro
    1190                1195                1200
Asp Glu Gln Asp Ala Ala Met Ala Ala Ala Val Asp Ala Ala Gln
    1205                1210                1215
Arg Asp Phe Arg Leu Ser Glu Gly Pro Leu Leu Arg Ala Arg Leu
    1220                1225                1230
Phe Thr Leu Gly Asp Ala Arg Pro Pro Arg Leu Tyr Leu Val Ala
    1235                1240                1245
His His Leu Val Ile Asp Gly Met Ser Trp Arg Ile Leu Leu Ala
    1250                1255                1260
Asp Leu Glu Thr Gly Tyr Arg Leu Ala Ala Asp Gly Arg Pro Ile
    1265                1270                1275
Asp Leu Gly Pro Arg Thr Thr Ser Phe Arg Asp Trp Ser Arg Arg
    1280                1285                1290
Leu Ser Arg His Val Ala Asp Gly Gly Leu Asp Ala Glu Leu Pro
    1295                1300                1305
Tyr Trp Lys Gly Val Gln Asp Ala Ala Arg Glu Thr Ala Pro Leu
    1310                1315                1320
Pro Val Asp Thr Gly Gly Leu Pro Asp Arg Gln Gly Ala Gln Glu
    1325                1330                1335
Glu Pro Gly Glu Asn Thr Ala Gly Ser Ala Arg Thr Val Ser Val
    1340                1345                1350
Gln Leu Ser Ala Ala Gly Thr Glu Ala Leu Leu Arg Gln Val Pro
    1355                1360                1365
Glu Ala Tyr Arg Thr Gln Ile Asn Asp Val Leu Leu Ser Ala Leu
    1370                1375                1380
Gly Arg Val Leu Thr Asp Trp Ala Gly Gly Glu Arg Val Leu Ile
    1385                1390                1395
Ala Leu Glu Gly His Gly Arg Glu Glu Leu Phe Asp Glu Val Asp
    1400                1405                1410
Leu Thr Arg Thr Val Gly Trp Phe Thr Thr Leu Phe Pro Val Ala
    1415                1420                1425
Leu Arg Met Pro Ala Asp Arg Asp Trp Gly Thr Val Leu Lys Ser
    1430                1435                1440
Val Lys Glu Gln Leu Arg Ala Val Pro His Asn Gly Leu Gly His
    1445                1450                1455
Gly Ala Leu Arg His Leu Ala Gly Pro Asn Ser Pro Leu Glu Asp
    1460                1465                1470
Gly Pro Glu Pro Glu Val Ser Phe Asn Tyr Leu Gly Gln Leu Asp
    1475                1480                1485
Val Ser Ala Asp Arg Thr Gly Leu Ala Arg Ala Met Leu Thr Ser
    1490                1495                1500
```

-continued

```
Glu Gly Ala Glu Arg Ala Ala Gly Gln His Arg Ala Gln Leu Leu
1505                1510                1515
Glu Ile Asn Gly Val Val Thr Gly Gly Arg Leu Glu Phe His Trp
1520                1525                1530
Thr Tyr Ser Val Asn Arg His Arg Ala Glu Thr Val Glu Arg Leu
1535                1540                1545
Ala Ala Gly Phe Met Thr Ala Leu Glu Ala Ile Val Ala His Cys
1550                1555                1560
Ala Ala Pro Gly Ser Gly Gly Ala Thr Pro Ser Asp Phe Pro Leu
1565                1570                1575
Ala Ala Leu Asp Gln Ala Thr Val Asp Lys Ile Ala Gly Asp Gly
1580                1585                1590
Arg Thr Val Glu Asp Ile Tyr Pro Leu Thr Ala Met Gln Ser Gly
1595                1600                1605
Met Leu Phe His Ala Leu Ser Glu Ser Gly Arg Asp Pro Tyr Thr
1610                1615                1620
Gly His Phe Gly Val Arg Val Asp Gly Ile Thr Asp Pro Gly Ala
1625                1630                1635
Leu Ala Ala Ala Trp Gln Gln Val Val Asp Arg Thr Pro Ala Leu
1640                1645                1650
Arg Thr Ala Ile Val Trp Gln Asp Val Ala Glu Pro Leu Gln Val
1655                1660                1665
Val His Ala Ala Ala Arg Val Pro Val Thr His His Asp Leu Arg
1670                1675                1680
Ser Leu Thr Glu Gln Glu Arg Gln Ala Ala Leu Asp Arg Leu Trp
1685                1690                1695
Glu Arg Arg Glu Glu Thr Val Ile Asp Leu Ala Val Ala Pro Ala
1700                1705                1710
Leu Arg Leu Thr Leu Val Arg Leu Thr Asp Ser Ala Val Gln Met
1715                1720                1725
Phe Trp Thr Ser His His Ile Leu Met Asp Gly Trp Ser Phe Ala
1730                1735                1740
Gly Leu Leu Ser Glu Val Cys Ala Gln Tyr Thr Ala Leu Thr Gly
1745                1750                1755
Gly Pro Arg Val Ala Ala Pro Ala Arg Arg Pro Tyr Arg Asp Tyr
1760                1765                1770
Val Gly Trp Leu Ala Glu Gln Asp Gln Pro Ala Ala Glu Ala His
1775                1780                1785
Trp Arg Ser Val Val Asp Gly Phe Thr Val Pro Thr Pro Leu Pro
1790                1795                1800
Tyr Asp Arg Gln Pro Val Lys Ala His Gly Thr Arg Ser Ser Arg
1805                1810                1815
Glu Val Arg Leu Gln Leu Ser Ala Glu Arg Ser Gly Arg Leu Ser
1820                1825                1830
Glu Ala Ala Arg Ser Ala Arg Leu Thr Val Asn Thr Leu Val Gln
1835                1840                1845
Gly Ala Trp Ala Ile Leu Leu Ala Arg Tyr Gly Gly Val Arg Asp
1850                1855                1860
Val Cys Phe Gly Thr Thr Val Ser Gly Arg Pro Ala Thr Leu Pro
1865                1870                1875
Gly Ala Glu Ser Met Ala Gly Leu Phe Ile Asn Thr Val Pro Val
1880                1885                1890
```

-continued

```
Arg Ala Thr Ile Asp Gly Ala Gly Ala Gly Asp Gly Ala Ala Thr
1895                1900                1905

Gly Thr Val Glu Trp Leu Arg Arg Leu Gln Ser Glu Gln Leu Asp
1910                1915                1920

Ser Arg Gln His Glu His Val Ser Leu Ala Gln Ile Gln Arg Trp
1925                1930                1935

Ser Gly Val Pro Ala Gly Thr Asn Leu Phe Asp Ser Ile Val Val
1940                1945                1950

Phe Glu Asn Tyr Pro Tyr Asp Ser Asp Ala Ala Lys Tyr Gly
1955                1960                1965

Leu Thr Leu Gly Thr Phe Gln Gly Asp Glu Val Thr Asn Tyr Ala
1970                1975                1980

Leu Thr Leu Thr Ala Tyr Val Ala Asp Glu Leu His Leu Asn Leu
1985                1990                1995

Gly Tyr Asp Pro Asp Leu Phe Asp Glu Ala Thr Val Glu Arg Met
2000                2005                2010

Ala Gly His Leu Ala Thr Leu Leu Asp Ala Val Ala Ala Ala Pro
2015                2020                2025

His Thr Pro Val Asp Asp Leu Pro Leu Leu Asp Ala Ala Glu His
2030                2035                2040

His Arg Leu Leu Thr Glu Trp Asn Asp Thr Ala Ala Gly Phe Pro
2045                2050                2055

Pro Pro Arg Pro Val His Glu Leu Phe Ala Glu Arg Ala Ala Arg
2060                2065                2070

Thr Pro Asp Ala Val Ala Val Ser Asp Ala Thr Arg Gln Leu Thr
2075                2080                2085

Phe Ala Glu Leu Glu Thr Arg Ala Asn Gln Leu Ala His His Leu
2090                2095                2100

Ala Gly Leu Gly Val Ala Pro Gly Thr Leu Val Gly Val Cys Ala
2105                2110                2115

Asp Arg Gly Val Asp Ala Val Val Ala Leu Leu Gly Val Leu Arg
2120                2125                2130

Ala Gly Gly Ala Phe Val Pro Leu Asp Pro Ala Tyr Pro Ala Glu
2135                2140                2145

Arg Leu Gln Val Met Leu Glu Asp Ala Ala Val Pro Val Val Val
2150                2155                2160

Thr Glu Glu Arg Leu Leu Asp Arg Thr Ala Gly His Asp Ala Thr
2165                2170                2175

Thr Val Cys Leu Asp Arg Asp Leu Pro Leu Leu Glu Glu Leu Pro
2180                2185                2190

Ala Arg Pro Pro Tyr Thr Ala Val Ala Pro Asp Asp Leu Ala Tyr
2195                2200                2205

Val Val Tyr Thr Ser Gly Thr Thr Gly Arg Pro Lys Gly Val Met
2210                2215                2220

Val Glu His Arg His Val His His Met Val His Ala Trp Asp Arg
2225                2230                2235

Arg Tyr Gly Leu Ala Ala Leu Gln Pro Arg Ala Leu Ser Val Ser
2240                2245                2250

Ser Ile Ser Val Asp Leu Phe Phe Ser Asp Phe Leu Leu Ser Ala
2255                2260                2265

Leu Phe Gly Gly Thr Met Val Ile Cys Pro Gln Asp Ala Val Ala
2270                2275                2280

Asp Gln Val Ala Leu Thr Asp Leu Leu Leu Lys Ser Arg Ala Gln
```

```
                2285                2290                2295
Leu Met Val Thr Val Pro Thr Leu Ala Arg Ala Val Val Ala Glu
        2300                2305                2310
Leu Ala Trp Arg Gly Val Thr Pro Glu Ala Leu Arg Val Leu Met
        2315                2320                2325
Val Gly Ser Glu Gly Trp Pro Ala Asp Ala Ala Glu Ile Leu
        2330                2335                2340
Ala Gly Leu Ala Pro Gly Thr Val Leu Val Asn Ala Tyr Gly Ser
        2345                2350                2355
Thr Glu Thr Thr Val Asp Ser Thr Val Phe Gln Leu Gly Arg Asp
        2360                2365                2370
Pro Leu Gly Asp Ala Ala Phe Val Pro Val Gly Arg Pro Leu Ala
        2375                2380                2385
Asn Thr Arg Ile Tyr Val Leu Asp Glu Arg Met Arg Pro Val Pro
        2390                2395                2400
Thr Gly Val Val Gly Glu Cys Tyr Ile Gly Gly Asp Gly Val Ser
        2405                2410                2415
Arg Gly Tyr Leu Gly Arg Pro Glu Leu Thr Ala Glu Arg Phe Leu
        2420                2425                2430
Asp Asp Pro Phe Ala Pro Glu Pro Gly Ala Arg Met Tyr Arg Thr
        2435                2440                2445
Gly Asp Leu Ala Arg Trp Arg Ala Asp Gly Asn Leu Glu Cys Leu
        2450                2455                2460
Gly Arg Val Asp Asp Gln Val Lys Ile Arg Gly Phe Arg Val Glu
        2465                2470                2475
Leu Gly Glu Val Glu Ala Ala Leu Ala Arg His Pro Ala Ile Asp
        2480                2485                2490
Ser Ala Ala Ala Ile Arg Lys Asp Asp Gly Pro Ala Arg
        2495                2500                2505
Leu Val Gly Tyr Val Val Pro Ala Ala Gly His Thr Pro Asp Leu
        2510                2515                2520
Ala Glu Leu Arg Ala Phe Ala Ala Glu Arg Leu Pro Ser Pro Ala
        2525                2530                2535
Val Pro Thr Ala Tyr Met Val Leu Asp Ala Leu Pro Met Thr Pro
        2540                2545                2550
Ser Gly Thr Val Ala Arg Arg Ala Leu Pro Ala Pro Ala Gly Ala
        2555                2560                2565
Gln Asp Ala Ala Arg Pro Tyr Thr Ala Pro Gly Ser Ala Thr Glu
        2570                2575                2580
Leu Leu Leu Cys Gly Ile Trp Gln Glu Val Leu Gly Val Glu Arg
        2585                2590                2595
Val Gly Val His Asp Asn Phe Phe Asp Leu Gly Gly Asp Ser Ile
        2600                2605                2610
Leu Ser Ile Arg Val Ile Ser Arg Ile Arg Ala Thr Leu Gly Val
        2615                2620                2625
Ala Pro Ser Pro Arg Gln Leu Phe Asp Thr Pro Thr Val Ala Gly
        2630                2635                2640
Leu Ala Ala Thr Leu Gly Arg Asp Asp Pro Ser Ala Ala Ala Asp
        2645                2650                2655
Val Pro Leu Glu Pro Ala Asp Arg Gly Ala Pro Leu Pro Leu Ser
        2660                2665                2670
Ser Ala Gln Gln Arg Gln Trp Phe Leu His Asn Phe Asp Pro Asp
        2675                2680                2685
```

```
Ser Ser Glu Tyr His Ile Val Thr Gly Leu Arg Leu Asp Gly Asp
2690                2695                2700

Leu Asp Val Ala Ala Leu Arg Gly Ala Leu Asn Gly Leu Val Ala
2705                2710                2715

Arg His Glu Ala Leu Arg Thr Thr Tyr Ala Ala Thr Gly Glu Gly
2720                2725                2730

Ala Glu Gln Ile Val His Pro Ala Gly Glu Val Val Cys Glu Arg
2735                2740                2745

Thr Asp Leu Ser Glu Val Pro Glu Asp Gln Arg Glu Asp Thr Leu
2750                2755                2760

Arg Gly His Ile Asp Arg Ala Ala Ala Arg Pro Phe Gly Leu Thr
2765                2770                2775

Glu Gly Pro Val Leu Arg Ala Glu Leu Phe Arg Leu Gly Ala Arg
2780                2785                2790

Asp His Leu Leu Leu Val Ile His His Ile Ala Thr Asp Gly
2795                2800                2805

Val Ser Met Gln Val Leu Thr Glu Glu Leu Gly Val His Tyr Ala
2810                2815                2820

Ala Ala Leu Asp Gly Thr Pro Pro Ala Leu Pro Ala Leu Pro Val
2825                2830                2835

Ser Tyr Ala Asp Tyr Ala Ala Trp Gln Arg Arg Met Leu Ser Gly
2840                2845                2850

Pro Ala Leu Asp Gly His Leu Ala Tyr Trp Gln Glu Arg Leu Ala
2855                2860                2865

Gly Val Arg Pro Leu Glu Leu Pro Thr Asp Arg Pro Arg Pro Ala
2870                2875                2880

Val Arg Ser Ser Ala Gly Arg Met Leu Leu Ile Glu Ile Glu Pro
2885                2890                2895

Arg Val Ala Ala Gly Leu Lys Glu Leu Ala Arg Arg His Asp Ala
2900                2905                2910

Thr Leu Phe Met Ala Leu Thr Ala Ala Val Gln Leu Leu Leu Ala
2915                2920                2925

Arg Tyr Thr Gly Gln Pro Asp Ile Val Val Gly Thr Pro Ala Ala
2930                2935                2940

Gly Arg Gly Arg Gln Glu Leu Glu Gly Leu Val Gly Leu Phe Val
2945                2950                2955

Asn Thr Val Ala Leu Arg Ser Thr Val Asp Glu Ser Gly Thr Phe
2960                2965                2970

Asp Ala Phe Leu Gly Ala Val Arg Asp Thr Val Leu Glu Ala Phe
2975                2980                2985

Val His Glu Asp Val Pro Phe Asp Arg Leu Val Glu Val Leu Arg
2990                2995                3000

Pro Arg Arg Asp Pro Ser Arg Asn Ala Leu Val Glu Val Phe Val
3005                3010                3015

Gly Leu Glu Thr Asp Arg Ser Ala Pro Pro Ala Leu Pro Gly Leu
3020                3025                3030

Thr Val Thr Glu Val Pro Phe Val Ser Gly Glu Val Ser His Asp
3035                3040                3045

Leu Ser Phe Asp Phe Val Asp Gly Pro Asp Gly Leu Lys Ala Ala
3050                3055                3060

Ile Gly Tyr Ser Thr Ala Leu Phe Asp Asp Gly Thr Val Glu Arg
3065                3070                3075
```

```
Met Ala Gly Gln Phe Gln Ala Leu Leu Ala Ala Val Leu Glu Asp
3080            3085                3090

His Arg Ala Leu Ala Asp Ile Ala Pro Ala Asp Glu Ala Glu Val
3095            3100                3105

Arg Arg Leu Ala Glu Leu Arg Gln Ala Ala Pro Ser Glu Pro Asp
3110            3115                3120

Ala Ser Glu Thr Asp Gly Ala Pro Ala Ala Tyr Arg Ala Pro Gly
3125            3130                3135

Thr Ala Ala Glu Arg Ala Leu Ala Glu Ile Trp Ala Ala Val Leu
3140            3145                3150

Gly Val Pro Arg Val Gly Thr Asp Asp Asn Phe Phe Gln Leu Gly
3155            3160                3165

Gly Asp Ser Leu Leu Ser Ile Gln Ala Val Gln Arg Met Arg Gln
3170            3175                3180

Ala Gly Leu Ala Val Thr Thr Lys Asp Leu Phe Val His Gln Ser
3185            3190                3195

Ile Ala Pro Leu Ala Ala Leu Ala Glu Glu Arg Ala Ala Asp Arg
3200            3205                3210

Pro Glu Ala Pro Gln Ala Gln His Asp Asp Ala Gly Thr Ala Gly
3215            3220                3225

Glu Ile Pro Leu Thr Pro Ile Gln Arg Asp Tyr Phe Ala Ala Gly
3230            3235                3240

Pro Leu Ala Pro His His Phe Thr Gln Ser Val Phe Leu Glu Leu
3245            3250                3255

His Ala Asp Leu Asp Glu Pro Ala Leu Arg His Ala Leu Ala Ala
3260            3265                3270

Leu Ile Gly His His Asp Ala Leu Arg Thr Arg Phe Val Arg Glu
3275            3280                3285

Asp Gly Asp Trp Arg Gln Tyr Ala Thr Pro Pro Glu Pro Val Asp
3290            3295                3300

Ile Leu Arg Arg His Asp Leu Ser Gly Leu Pro Glu Ala Gln Arg
3305            3310                3315

Ala Ala Ala Met Asp Glu Leu Ala Ala Ser Ala Asp Ala Gly Leu
3320            3325                3330

Asp Leu Ala Ala Gly Pro Pro Ala Ala Ala Leu Leu Phe Val Phe
3335            3340                3345

Gly Pro Gly Glu Arg Pro Ala Leu Phe Val Thr Ala His His Leu
3350            3355                3360

Val Val Asp Gly Val Ser Trp Arg Ile Leu Leu Glu Asp Leu Glu
3365            3370                3375

Ala Gly Tyr Val Gln Ala Arg Asp Gly Lys Pro Val Ser Leu Gly
3380            3385                3390

Ala Lys Ser Thr Ser Phe Gly Gln Trp Ala His Arg Leu Ala Arg
3395            3400                3405

His Ile Ala Asp Gly Gly Leu Ala Glu Gln Ala Ala Tyr Trp Gln
3410            3415                3420

Ala Leu Pro Asp Gly Thr Glu Val Pro His Asp Gly Ser Gly Pro
3425            3430                3435

Ala Val Val Glu Ser Val Gln Thr Val Thr Val Glu Leu Pro Glu
3440            3445                3450

Asp Thr Ser Glu Val Leu Leu Arg Arg Ser Ala Gly Val Phe Arg
3455            3460                3465

Thr Arg Phe His Glu Val Leu Phe Ala Ala Leu Ala Gly Thr Leu
```

-continued

```
            3470               3475               3480
Ala Arg Trp Thr Gly Glu Arg Gln Val Val Phe Asp Thr Glu Gly
    3485               3490               3495

His Gly Arg Glu Asp Leu Phe Asp Asp Val Asp Leu Ser Arg Thr
    3500               3505               3510

Val Gly Trp Phe Thr Thr Glu Tyr Pro Val Ala Leu Glu Val Ala
    3515               3520               3525

Gly Asp Arg Asp Asp Trp Pro Ala Leu Ile Arg Ser Val Arg Gly
    3530               3535               3540

Gln Leu Arg Ser Leu Pro Gly Asn Gly Phe Gly Tyr Gly Ala Leu
    3545               3550               3555

Arg His Leu Ser Pro Ala Gly Thr Pro Gly Ala Ala Leu Ala Glu
    3560               3565               3570

Arg Ala Pro Ala Gln Val Val Phe Asn Tyr His Gly Gln Ala Asp
    3575               3580               3585

Glu Ala Gln Arg Ala Ala Glu Ser Asp Leu Tyr His Ala Phe Gly
    3590               3595               3600

Asp Pro Ile Gly Arg Glu Gln Arg Pro Asp Glu Leu Thr Gly His
    3605               3610               3615

Pro Val Glu Val Val Gly Ala Val His Ser Gly Arg Leu Arg Phe
    3620               3625               3630

Thr Trp Tyr Phe Ser Arg Asn Val His His Arg Ala Thr Ile Asp
    3635               3640               3645

Lys Val Ala Glu Asp Phe Ala Asp Ala Leu Arg Ala Ile Ala Arg
    3650               3655               3660

His Ile Thr Glu Arg
    3665
```

<210> SEQ ID NO 5
<211> LENGTH: 11007
<212> TYPE: DNA
<213> ORGANISM: Streptomyces hygroscopicus

<400> SEQUENCE: 5

```
atgaccagct ctgcagcgga ccagcccgac aacccgaaca ccaccacccc ggcgtcgcgt     60
gccgagcgca ccgccgcgct gccggcccat gtgcaggagc tgctgcgcgc ccggctggcc    120
ggccgggccg ccgcgacggg cggcgcggac accatcccgc gcatcgggca cgacggcccc    180
gtcgcgctct cgcccgccca ggaacgcctc tggtacctgc atgagctcga accggagagc    240
aacgagtaca cacccctgcg cgtcctgcgg ctgcgcggcg acctcgaccc cggcgcgctg    300
tccgcggcgc tgagcgagat cgtcgcccgg cacggcgcgc tccgcaccac cttcggctcc    360
cgcgagggc acgccgagca gaccgtgcat ccgcccgtac cgacaccgct gccgctcgtc    420
gacctgtcgg cggcggacga cggcgagcgg gacgacgcgc tcggaccct gctgcagtac    480
gaggcccggc gccccttcga cctgcgccgc ggcccggtgc tgcggcgcgca gctgatccgg    540
ctggcggccg acgaccatgt cctcgcgctg gccctgcatc acatcgtcac cgacggctgg    600
tcgatgggcg tgctcaccgg cgagctcacc gcccactacg ccgcgacgct gcgcggtgcg    660
cccgccgtac tgcccgaact tccggtgagc tacctcgatg tcgccgtctg gcagcgtgac    720
cagctgagct ccgcgcggct gcgcgagggg ctcgaccact ggcgcgggga gctggccggg    780
ctggtcccgc tcgatctgcc gacgacctgg cagcggccgc cggtccgcac cagcgccgga    840
gcgctgcact ccttcgagat cccccgcgcg gtcgccgcac gccttcggga gctgggccgg    900
```

```
gaacagggcg ccacgctgtt catggcgctg gtcgccgcgg tccagctgct gctgtcgcgc    960
tggtcggggc agcgggacat cgcggtgggc accgccgcgg ccgggcgcgg ccggaccgag   1020
accgagaatc tgatcggctt cttcgtcaac aatctggtcc tgcgctcccg gatcgatgag   1080
acgcggtcgt tcaccgagct gctgcgggcg gtacgcgcga cggtcctgga cgccttcgcc   1140
cacgaggatg tgccgttcca gcgggtcgtc gaggcgctgc atccggagcg cgacctcagc   1200
cggccgccgc tggccgaggt cgcggtgaat ctgcacaaca ccccgcggac cgacacggag   1260
ctgcccgggc tgcggatcga ggagatgccg ccgccggtgt tcgcctccag catggacctc   1320
tcgttcgact tcaccgagcg cgacgaccgg ctcgaagggc acctcaccta caacaccgat   1380
ctgttcgccg cggacgccgc cgcgcggatg ccgcgcagc tggtcaccct gctcgaggac   1440
ctcacccgcc ggcccgcggt cccggtggcc gggctggccg tgctgccggc cgccgagcac   1500
cgtcgggtga ccgaggagtg gccgcactcc gggcccggcc gggagccgcg taccgcaccg   1560
gagttgttcg ccgcgcaggt cgcgcggacc cctgatgcgg atgcgctggt ctccgacgag   1620
gagacgctca gctatgccga gctggacggc cgtatcaacc agtgggcgcg gctgctactg   1680
gccccggggtg ccgggccgga gacgctggtg gcggtggcgc tgccccgctc cgcgcagatg   1740
gtcacggcga tcctggcgat ccagaagacc ggtgccgcct atctgccgct ggacccgaag   1800
agccccgcgg aacgcaaccg gctgatgatc gaggacgccc gccgctgct ggtgctgacc   1860
tcggccgggt tcggcgacgg cgcggaactc ggcgcgcccg cactgttcct ggacgacccg   1920
gacacccgcg ccgccgcagg cgagctgtcc gccggcccgc tggcggccgc cgagctgccc   1980
gccccgctgc tgcccggcca cccggcctac gtcatctaca cctccggttc caccggccgc   2040
cccaagggcg tggtggtcac ccacaccggt gtgcacggcc tcgtggcggc gcagtcggcg   2100
cacttccgta ccgggcacgg cgcgcgggtg ctgtcgttcg cctcgctcgg cttcgacgcg   2160
gccttctccg agctgggcat ggcgctgctg tccggcggtg cgctggtcgt cgtcgaccag   2220
gagcggatcc tgcccggaca ccgctggcc gacgtgctgg ccgagcaccg ggtcacccat   2280
gtgacgctgc cgcccagcgc gctgtccgcg ctgacccccgg ggacgctgcc gaaggacctc   2340
accctggtcg tggccggcga ggcctgcccg cccgcggtgg cccgcacctg gtccgcccat   2400
caccgcatga tcaacgccta cggcccccacc gagtccacgg tctgcgccag catgagcgcc   2460
gcgctgaccc cggacaccgt cagcggcgac tcggtcccca tcggccgccc gctctccggc   2520
gtccgggtca gcgtcctgga cgaccggctg cgcccggtgc cggccggcgt ccccggcgag   2580
gtgtatctct ccgcgccgc gctggcccgc ggctacctcg gcggctcgc gctgaccgcg   2640
gagcggttcg tcgccgaccc gtacggtccg ccgggaagcc ggatgtaccg caccggcgac   2700
cgcgcccgct ggctggccgg cggcgacctg gactacctgg gccgcaccga cgaccaggtc   2760
aaactgcgcg gcttccggat cgagctcggc gaggtcgagg ccgtactgtc gcgccacgac   2820
ggggtcggcc cggtggccgc cacggtgcac aaggacgagc ggggcacccg ccgcctggtg   2880
gcgtacgtcg tcccggcgcg ggaggacgcg ccgacccgg cgcggctgcg cgagttcgcc   2940
cgcgaggtgc tgcccgagca catggtgccc tcggtcttcg tgccgctgga ccggctgccg   3000
ctgaacgcca acggcaaggt cgaccggcgg gcgctgcccg cacccgacat ccggcgcgac   3060
gagggcagcg cccgtatcgc gccgcgcacc ccggcggagg agacgctggc gcgcatctgg   3120
tcggaggtgc tgggcgtcac ggacatcggc gtcgaggaca acttcttcga cctcggcggc   3180
gactccatcc tcagccttca ggtggtggcg cgggcccggg ccgccggact gcggctgacc   3240
gccaagcaga ccttcctgcg gcagaccatc gccgatctcg ccgccgacgc cgtcgccgag   3300
```

-continued

```
accgaccccg ccgcgcacgg tgcggccaac gacggcccgg tcaccggcga gctgccgctc    3360 accccatcc agcactggtt cttcaactcc ctcggcgaca gcctggagca gttcaaccag     3420
tcgctgtatc tggagctggc cgagggcccc gacctcccgg cgctgcgcgc cgcactggcc    3480
gcgctgaccg aacagcacga cgcactgcgg ctccgcgccg tatccgagga cgggcagtgg    3540
cggctgcacc acgcgcccgc cgagaccggt caactcctcg aacacctcga tctgtccggc    3600
gtctcgcccg acgagcagga cgccgcgatg gcggccgccg tcgacgcggc gcagcgggac    3660
ttccggctgt ccgaggggcc gctgctgcgg gcccggctgt tcaccctcgg cgacgcccgg    3720
ccgccccggc tgtacctcgt cgcgcaccac ctcgtcatcg acggcatgtc ctggcgcatc    3780
ctgctggcgg acctggagac cggctaccgc ctggcggcgg acggccggcc gatcgacctg    3840
gggccccgga ccacctcgtt ccgcgactgg tcgcgccggc tgtcgcgcca tgtcgcggac    3900
ggcggcctgg acgccgaact gccgtactgg aagggcgtac aggacgcggc gcgcgagacc    3960
gccccgctcc ccgtcgacac cggcgggctc cccgaccgcc agggcgccca ggaggagccc    4020
ggcgagaaca ccgccgggtc ggcccgcacc gtctccgtac agctgtccgc cgcgggcacc    4080
gaggcgctgc tgcggcaggt gcccgaggcc taccgcaccc agatcaacga cgtcctgctc    4140
agcgcgctgg gccgggtgct gaccgactgg gcgggcggcg agcgggtgct gatcgccctg    4200
gagggccacg gccgcgagga gctcttcgac gaggtggacc tcaccgcac cgtcggctgg     4260 ttcaccaccc tcttcccggt cgccctgcgg atgccggccg accgggactg gggaacggtc    4320
ctcaagagcg tcaaggaaca gctgcgggcg gtgccccaca acggactcgg ccatggcgcg    4380
ctgcgtcatc tggcagggcc caactcccct ctggaggacg gtccggagcc cgaggtcagc    4440
ttcaactacc tcgccagct ggacgtgtcc gccgaccgca ccggcctcgc ccgcgccatg     4500
ctcaccagcg agggcgccga gcgggccgcc ggccagcacc gtgcgcagct gctggagatc    4560
aacggcgtgg tcaccggcgg ccggctggag ttccactgga cgtactcggt gaaccggcac    4620
cgcgcagaga ccgtcgaacg gctcgccgcg ggcttcatga ccgcgctgga agcgatcgtg    4680
gcgcactgcg ccgcccccgg ttccggcggc gccaccccgt ccgacttccc gctggccgcc    4740
ctcgaccagg ccaccgtcga caagatcgcc ggcgacggcc gcacggtcga ggacatctac    4800
ccgctcaccg cgatgcagag cggcatgctc ttccacgcgc tgagcgagtc cggacgcgac    4860
ccgtacaccg ggcacttcgg cgtccgcgtg gacggcatca ccgacccggg ggcactggcc    4920
gcggcctggc agcaggtcgt cgaccggacc cccgccctgc gcaccgccat cgtctggcag    4980
gacgtcgcgg aaccccttca ggtggtgcac gcggccgccc gtgtgccggt cacccatcac    5040
gacctgcggt ccctgaccga gcaggaacgg caggccgccc tggaccggct gtgggagcgg    5100
cgcgaggaga ccgtcatcga tctcgccgtc gcgcccgcgc tgcggctgac cctcgtccgg    5160
ctcaccgaca cgcgccgtcca gatgttctgg acctcgcacc acatcctgat ggacggctgg    5220
agcttcgccg ggctgctgtc ggaggtgtgc gcccagtaca ccgcgctgac cggcggcccc    5280
cgcgtggcgg cccccggcccg ccgcccgtac cgcgactatg tcggctggct ggccgaacag    5340
gaccagccgg ccgccgaggc gcactggcgc tcggtggtcg acgggttcac ggtgccgacg    5400
ccgctgccct acgaccggca gccggtgaag gcacacggca cccggtcctc gcgtgaggtg    5460
cggctgcagc tgtccgccga gcgctccggg cggctgtccg aggccgcccg gtcggcgcgg    5520
ctgaccgtca acacgctggt gcagggcgcc tgggcgatcc tgctggcgcg ctacggcggg    5580
gtgcgcgacg tctgcttcgg caccaccgtc tccggccgtc ccgccaccct gcccggcgcc    5640
```

```
gagtcgatgg ccgggctgtt catcaacacc gtgccggtac gggcgaccat cgacggtgcc    5700
ggtgccggcg acggcgccgc caccggcacc gtcgagtggc tgcggcggct gcagagcgag    5760
cagctcgact cccggcagca cgagcatgtc tcgctggcgc agatccagcg ctggagcggc    5820
gtaccggccg gcaccaacct cttcgacagc atcgtcgtct cgagaacta cccctacgac     5880 agcgatgcgg ccgccaagta cgggctgacc ctcggcacgt tccagggcga cgaggtcacc    5940
aactacgccc tcaccctgac cgcgtacgtg gccgacgagc tgcatctcaa cctcggctac    6000
gacccggatc tgttcgacga ggcgaccgtc gagcggatgg ccgggcatct ggcgacgctg    6060
ctcgacgccg tcgccgccgc cccgcacacc ccggtggacg acctcccgct gctcgatgcg    6120
gccgaacacc accggcttct caccgagtgg aacgacaccg ccgccggctt ccgccgccg    6180 cggccggtcc atgagctctt cgccgagcgg ccgcccgta ccccgacgc ggtggcggtc     6240 agcgacgcca cccggcagct gaccttcgcc gagctggaga cccgcgccaa ccaactggcg    6300
caccacctgg ccggtctggg cgtggcgccc ggcacgctgg tcggggtgtg cgccgaccgc    6360
ggggtggacg ccgtggtggc gctgctgggc gtgctgcggg ccggcggtgc cttcgtaccg    6420
ctggaccccg cctatccggc ggagcggctc caggtcatgc tggaggacgc cgcggtgccg    6480
gtcgtggtga ccgaggagcg gctgctggac cggaccgccg gcacgacgc gacgacggtg    6540 tgcctggacc gcgatctgcc gctgctggag gagctgccgg cccgcccgcc gtacaccgcc    6600
gtggcaccgg acgacctggc gtatgtcgtc tatacgtcgg gcaccaccgg gcgccccaag    6660
ggcgtgatgg tcgagcaccg gcacgtccac cacatggtgc acgcctggga ccggcgctac    6720
gggctcgccg cgctgcaacc gcgcgcgctg tccgtctcca gcatctccgt cgacctgttc    6780
ttcagcgact cctgctctc cgccctcttc ggcggcacga tggtgatctg tccgcaggac    6840
gccgtcgccg accaggtggc gctgaccgat ctgctgctca agagccgggc ccagctgatg    6900
gtgacggtgc cgacgctggc ccgcgcggtg gtcgccgagc tcgcctggcg cggtgtgaca    6960
ccggaggcgc tgcgggtgct gatggtgggc tccgagggct ggccggccga tgccgcggcc    7020
gagatcctgg ccggtctcgc gccgggcacg gtgctggtca acgcgtacgg atcgaccgag    7080
accacggtcg actccacggt cttccagctc ggccgcgacc cgctgggcga cgccgccttc    7140
gtaccggtcg gcaggccgct cgccaacacc cggatctatg tgctggacga gcggatgcgc    7200
ccggttccca ccggcgtcgt cggcgagtgc tacatcggcg gcgacggagt gtcgcgcggc    7260
tatctgggcc gcccggagct gaccgccgag cgtttcctcg acgaccgtt cgcgccggag    7320 ccgggcgccc ggatgtaccg gaccggtgac ctcgcgcgct ggcgggccga cggcaacctc    7380
gaatgcctcg gccgggtcga cgaccaggtc aagatccgcg gcttccgggt ggaactcggc    7440
gaggtggagg ccgcgttggc ccgccacccg gcgatcgact cggcggccgc cgcgatccgc    7500
aaggacgacg gtgggccggc ccgtctggtg ggctatgtcg tgcccgccgc cggccacacc    7560
cccgacctgg ccgagctacg ggccttcgcc gccgaacggc tgccgtcgcc cgccgtcccc    7620
accgcgtaca tggtgctgga cgcgctgccg atgacgccga gcggcaccgt cgcccggcgt    7680
gcgctgccgg ccccggccgg ggcgcaggac ccgcccggc cctacaccgc gccgggcagc    7740
gccaccgagc tgctgctctg cggtatctgg caggaggtcc tgggcgtcga acgggtcggc    7800
gtgcacgaca acttcttcga cctgggcggg gactcgatcc tcagcatccg ggtcatctcc    7860
cggatccggg ccacgctggg cgtcgcccg tcgccccgcc agctcttcga caccccgacg    7920
gtggccggtc tcgccgccac cctcggccgg gacgacccct cggcggccgc cgacgtcccc    7980
ctggagccgg ccgaccgcgg cgcaccgctg ccgctgtcgt ccgcccagca acgccagtgg    8040
```

-continued

```
ttcctgcaca acttcgaccc ggacagcagc gagtaccaca tcgtcaccgg gctccggctc    8100
gacggtgatc tggacgtcgc ggcgctgcga ggggccctga acgggctcgt cgcccggcac    8160
gaggcgctgc gtaccaccta cgcggccacc ggcgagggcg ccgagcagat cgtgcacccc    8220
gcgggcgagg tggtctgcga gcgtacggat ctgtccgagg tgcccgagga ccagcgcgag    8280
gacaccctgc gcgggcacat cgaccgcgcc gccgccggc cgttcggcct caccgagggc     8340
ccggtcctgc gcgccgaact gttccggctc ggcgcccgtg accatctgct gctgctcgtc    8400
atccaccaca tcgccaccga cggtgtctcg atgcaggtgc tcaccgagga gctcggcgtc    8460
cactacgccg cggcgctcga cggcacaccg cccgccctgc cggcgctgcc ggtctcctac    8520
gccgactacg cggcctggca gcgccggatg ctgtccggcc cggcgctgga cggccatctc    8580
gcctactggc aggagcggct ggccggtgtc cggccgctgg agctgcccac cgaccggccc    8640
cggccggcgg tccgcagctc cgcgggccgg atgctgctga tcgagatcga gccgcgggtg    8700
gccgcgggcc tcaaggaact ggcccgccgc catgacgcca ccctgttcat ggcgctcacc    8760
gcggcggtcc agctgctgct ggcccgctac accggacagc cggacatcgt cgtgggcacc    8820
ccggccgccg gccggggccg gcaagaactc gagggggctcg tcgggctgtt cgtcaacacg    8880
gtggcgctgc ggtccaccgt cgacgagagc gggaccttcg acgccttcct cggtgcggtg    8940
cgcgacaccg tcctcgaagc gtttgtgcac gaggacgtgc cgttcgaccg gctggtcgag    9000
gtgctgcgac cgcgccgcga ccccagccgt aacgcactgg tggaggtgtt cgtcggactg    9060
gagacggacc ggtcggcgcc gccggcgctg cccggactga cggtgaccga ggtcccgttc    9120
gtcagcggcg aggtcagcca tgacctcagc ttcgacttcg tcgacgggcc cgacggcctg    9180
aaggcggcca tcggctacag caccgcgctg ttcgacgacg gcaccgtcga gcggatggcc    9240
ggccagttcc aggcgctgct cgccgcggtc ctggaggacc atcgcgcgct cgccgacatc    9300
gcacccgcgc acgaggccga ggtgcggcgg ctcgccgaac tgcggcaggc cgcgccctcg    9360
gagcccgacg cgtcggaaac cgacggcgcg ccggccgcct accgcgcgcc cgggaccgct    9420
gccgagcggg ccctggcgga gatctgggcc gccgtgctgg gggtgccgcg ggtcgggacc    9480
gacgacaact tcttccagct gggcggcgac tccctgctca gcatccaggc ggtgcagcgg    9540
atgcggcagg ccggcctggc ggtgaccacc aaggatctgt tcgtccacca gagcatcgcc    9600
ccgctggcgg ccctcgccga ggaacgggcg gcggaccggc cggaggcccc ccaggcgcag    9660
cacgacgatg ccgggacggc gggcgagata ccgctcaccc cgatccagcg cgactacttc    9720
gcggccgggc cgctcgcccc gcaccacttc acccagtcgg tgttcctcga actgcacgcc    9780
gatctcgacg agccggcgct gcggcacgca ctggccgcgc tgatcggcca ccacgacgcc    9840
ctgcggaccc gcttcgtacg cgaagacggc gactggcggc agtacgccac cccgccggag    9900
ccggtggaca tcctgcgccg gcacgacctg tccgggctgc cggaggctca acgggccgcc    9960
gccatggacg agttggcggc ctcggccgac gccgggctcg atctggcggc cgggccgccg    10020
gccgcggcgc tgctgttcgt cttcgggccc ggggagcggc cggcgctgtt cgtgaccgcg    10080
caccatctcg tcgtcgacgg cgtctcctgg cggatcctgc tggaggacct ggaagccggc    10140
tacgtccagg cccgcgacgg gaagccggtg tccctgggcg ccaaaagcac ctcgttcggg    10200
cagtgggcgc accggctcgc ccggcacatc gccgacggc gcctcgccga gcaggccgcc    10260
tactggcagg cgctgcccga cggcaccgag gtcccgcacg acggctcggg gcccgcggtg    10320
gtggagtccg tgcagaccgt cacggtggag ctgccggagg acaccagcga ggtgctgctg    10380
```

| | |
|---|---:|
| cgccggtccg ccggggtctt ccggacccgc ttccacgagg tgctgttcgc cgcgctcgcc | 10440 |
| ggcaccctgg cccggtggac gggcgaacgc caggtcgtgt tcgacaccga gggccacggc | 10500 |
| cgggaggacc tcttcgacga cgtcgatctc tcccggaccg tcggctggtt caccaccgag | 10560 |
| taccccgtcg cccttgaggt ggccggcgac cgggacgact ggccggcgct catcaggtcg | 10620 |
| gtacgcggac agctgcggtc gctgcccggc aacggcttcg gttacggcgc gctgcggcat | 10680 |
| ctgagcccgg ccggcacccc gggtgccgca ctcgccgaac gggccccggc ccaggtggtg | 10740 |
| ttcaactacc acggccaggc cgacgaggcg cagcgcgcgg cggagagcga cctctaccac | 10800 |
| gcgttcggcg acccgatcgg ccgggagcag cggcccgacg agctgaccgg cacccggtg | 10860 |
| gaggtggtgg cgccgtgca ctccgggcgg ctccgcttca cctggtactt ctcgcgcaat | 10920 |
| gttcatcaca gggccaccat cgacaaggtg gccgaggact cgccgacgc gctgcgcgcc | 10980 |
| atcgcccggc acatcacgga gcggtga | 11007 |

<210> SEQ ID NO 6
<211> LENGTH: 972
<212> TYPE: DNA
<213> ORGANISM: Streptomyces hygroscopicus

<400> SEQUENCE: 6

| | |
|---|---:|
| atgtccgcca cgccgcgccc gcgacccgtt ctacgccgt tccgccccgg agacggccgc | 60 |
| tcgctgctgg cggcctggtg ccgcagcgcc ccggacgatc cgatcaccgc cgcccgcttc | 120 |
| cggacgctga tcctgctcga ccccaatttc gacccagagg ggttacgggt ggccgatctc | 180 |
| gacgggcagg tggtgggcgc cgtctacgcc gtgcgccgcc gtaccccgct ggccggcacc | 240 |
| gacctggagc cggacgtcgg ctggatcctg ttcttcttcg tcgatccgcc gcaccgccgt | 300 |
| acgggcctcg gccgccggct gctcaccgat gccctcgact ggctgcgcgg acacggccgc | 360 |
| acccgggtcg acttcgcccc gtacgccccc cactacgtgc tccccggcct ggaccgggcc | 420 |
| gcgtacccga aggccgcccg gctgctggcg agcctcggct tccgtccccg ctacgaggcc | 480 |
| gcggcgatgg accgcggcct ggtcggctac cgcatgccgg acgaggtacg gcggcacgag | 540 |
| gcggcccctga cggcgcgcgg ccaccgattc ggcaccccgt ccgacgacga tctggtggac | 600 |
| ctgctcgggc tggccgagga gttcaccccc gactgggcgc gggcgatccg gcagtgcctg | 660 |
| accggcggcg cccctctgga ccgcatcgtc agcgcccgcg cacccgacgg gcggatggcg | 720 |
| ggctgggcca tgcacggcgc gtacgacggt acggccgagc ggttcggccc cttcggcgta | 780 |
| cggaaggagc tgcgcggcgc cggtctgggc aaggtgctgc tgcatctgac gctggagcgg | 840 |
| atgcgggcgc tcggcgtgca cggggcgtgg ttcctgtgga cgggcgagca gagcccggcg | 900 |
| gggcatctct accgcgcgag cggattcacc acgacccgga ggttcacggt gctgcggtgg | 960 |
| gaggcgggat ga | 972 |

<210> SEQ ID NO 7
<211> LENGTH: 1416
<212> TYPE: DNA
<213> ORGANISM: Streptomyces hygroscopicus

<400> SEQUENCE: 7

| | |
|---|---:|
| atgaggcgcc gtacattcac ggccggggcc gcggcggggg ccgccctgtt ggccggggcc | 60 |
| ggatgcgacg cgcccggtgg cgccgggcac ggagacggaa agcacggaga cggagacggc | 120 |
| ggtgacggcc ggggcagcgg cggccgtcgc ggcgcccccg tcaccctgac cgtcctcacg | 180 |
| cactacgcga gcgaaccgct cgcctcggcg ctgcaaaccg tcgtcgacgc ctggaacgcg | 240 |

-continued

```
acgcaccggc gcatcacggt gcgcacggcc gcggtcaagt tccccgatct gctgacgact      300
tacatggtgc ggcaggccgc gggccagggc gccgacatca tccatccgta ctgcctgtgg      360
accggccagc tggtgcgggc cggagtactg cgcccggtgc cgcccacggc cacgcggcag      420
atccgccggg acttcacccc ggcggccgtg gcggcgtcgt ccgtgcacgg cacgctctac      480
ggctacccca cggaggtgca gacctacgcg ctctactaca acaagcggct gctgcggcag      540
gccggtatcg acggaccgcc gggtacctgg caggagctgg aggacgcggc gtaccgcacc      600
gcccgccgcg accgccacgg caacatgctg gtgcagggct cgggctgtc acgggccgac       660
gatgcgagcg tcgtggggca gacgctggcc ctgctggccg cgcgcggcgg cacattcctc      720
acctccgacg gacggcggac cgccatcggc tcggcggccg gcgggatgt gctcgacctg       780
gagcgccggc tcatcgaccg cggcgccgcc gactccggta tctcgctcct gagggccttt      840
ccgtccggcc aggtggcgat ggcgatcaac gccggctggt ggacggcgag tctgcgcggc      900
gcgatggggg cggactaccg cgaggtcggg gtggcgccgg tgccggggcc cgcaccggac      960
gaccgcggca cgctcgccac gggcttcctg ctcggcgtga acgcgaagag cagatatccg     1020
ggggaggcct gggagttcct gcactggctc aacggtgtgc gggcgccggc cgcccggccg     1080
gggcgcagcg cggggaggagg cgtcccggtg tccaggatga gcgcgctcca ggtgtcggtc    1140
ggttcgatga ccgggcgggc ggacgatatg cgggcgctgc tggaggcgca cggcgagagg    1200
gacgccgacg gccgtggtgg cggcgaccgg aacctcggcc ccttcctgga cgcgctgcgc    1260
tacgccgtcc cggaaccgaa cggtccgcgc gcgcagcagg ccaaatcgct gctgcgcaag    1320
aacatcgagg acgtctggac gggccgggcc tcggtcgatg ccgcgctgcg caccgccggc    1380
cggcagatcg accaggaact gtcccggccc tactga                              1416
```

<210> SEQ ID NO 8  
<211> LENGTH: 912  
<212> TYPE: DNA  
<213> ORGANISM: Streptomyces hygroscopicus

<400> SEQUENCE: 8

```
atggcttcag ccggcggtgg tcccgtcagg gcggcccggc ggcggcagac cgccgtcgcc       60
tatctgttcc tgaccccggc cctgctgttc ttcgcggtct tcctcgccct gccgctgctg      120
ttcgccgtgc tgctcgcgca gtcgcgctgg gccggcttcg acctcgccga tatcgagccg      180
gtcgggatgg ccaacttcac cgacctcttc gcccgcggct cgaccttcct gacgcccgtc      240
ctcaccaata cgctgctgta cgccgtcggc accgtcgcga tcgccctcat cggcgcgctc      300
accctcgcga cctgcatcga caaccttcgt ttccaggggc tttggcggac cctctatttc      360
ctcccgatcg tgacgaccgt ggtcgccgtc ggcaacgtat ggaagtacat gtacgcaccg      420
ggcgggctga tcaacggagt gctcaacggt ctgggtctgc attccgtggc ctttctccag      480
gaccccggca cggcgctgcc gtccgtcgtc gtggtgcagg catgggcctc catgggaacc      540
gcgatcctga ttctcaccgc gggcctgaag tcgatccccg aggcctatta cgaggccgcc      600
gagctggacg gtgccggcgc cggcaccgtt tccggcgca tcaccctgcc gctgctccgg       660
ccgtccctgc tcttcgtctg catcacccaa ttcatcaccg gattacagtc gttcgccctg      720
atcaatgtca tgacgacga cggcggaccg ggcgatgcga cgaatgtcgc ggccctggag       780
atgtatcagc aggcgttcag gtacggcgac tggggaatcg ccagtgccgc cgcctttgtg      840
ctgttcctgg tcattgtcgc gatcacggtg gggcagctct ggctgttccg ccggaaaggc      900
ggggaatcgt ga                                                         912
```

<210> SEQ ID NO 9
<211> LENGTH: 891
<212> TYPE: DNA
<213> ORGANISM: Streptomyces hygroscopicus

<400> SEQUENCE: 9

| | | | | | |
|---|---|---|---|---|---|
| gtgagccggt | ccgctcgtcg | gcgcccgggc | cgtcgccgcc | cctggggctc | gtacgccgtg | 60 |
| gtcgtcgccg | gggccgccct | caccctcgtc | ccgttcctcg | acatgctgct | gacctcgttc | 120 |
| aaggggcccg | gcgaatacgg | gaaactcccc | taccgattcc | tcccccaggc | gttcgacctt | 180 |
| tccaactacc | gtgccgcgat | ggagcagctg | gatctgcccc | tgcttttccg | caacagcgtc | 240 |
| atcgccaccg | ccgtcatcac | cggatccatc | ctggtgacct | ccgcgctcgc | cggatacgcg | 300 |
| ctggccaagc | tgcgcttccc | cggccgggag | gtgatcttcc | gcctggtcct | gtccacgatg | 360 |
| atgttcccgc | cgttcctctt | cttcatcccg | cactttctga | tcctggtgca | ctggcccggc | 420 |
| gccggcggca | acgacctgct | gggccgcggc | ggggcgggcc | tcaccgtgag | ccttgcggcg | 480 |
| ctggtcatgc | cgttcctcgt | atccggtttc | gggatctttc | tgatgcggca | attcatggtc | 540 |
| tccatcccgg | acgaactgct | ggaggcggcc | cgtatcgacg | gcgccggcga | attcgccctc | 600 |
| tggtggcgca | tcgtgctgcc | ccagacgaaa | ccggtggcgg | tcaccctcgc | gctgctcacc | 660 |
| ttcgtcaacg | cctggaacga | atacatctgg | gcgctgctga | tctccaccgc | caatccgcgg | 720 |
| ctgatgacgc | tgccggtggg | catccagatg | ctgcagagct | atctcgaccc | cgaccgtatg | 780 |
| gtcccggtca | tgatggccgg | cctggtgctg | agcatcctgc | cggtcctgct | gctcttcctg | 840 |
| ctgctccaga | agcactacct | gcgcggggtg | atgctcagcg | gcctcaagtg | a | 891 |

<210> SEQ ID NO 10
<211> LENGTH: 1278
<212> TYPE: DNA
<213> ORGANISM: Streptomyces hygroscopicus

<400> SEQUENCE: 10

| | | | | | |
|---|---|---|---|---|---|
| atgagttccg | gtttctcctg | ggctgttgtg | gcaactgtgg | tgagagtttc | tgaccccctca | 60 |
| ggaggaacca | tggcttccga | ctcgtcgtcc | ccgacgccga | tgccggccgt | gtcgttgatc | 120 |
| gtgccgacgt | tcaacgaggc | agcgaacatt | gatgagttgc | tcgacggcgt | gtgtgcggcg | 180 |
| atcccggcgg | gtctggaggt | cgaggtgctg | ttcgtcgacg | actcgacgga | tgacacaccg | 240 |
| gaagtcatcg | agaaggcggc | cgcgcgctgt | ccgatgccgg | tgtcggtgct | gcaccgggag | 300 |
| gttcccgaag | gggggctcgg | cggagcggtg | gtggccggga | tcgcccgtac | gagtgcgccg | 360 |
| tggatcatgg | tgatggacgc | cgatctgcag | catccgccgg | agctgctgcc | gcagttgatc | 420 |
| gaggctggtg | agcgcgcggc | ggccgagttg | gtggtggcca | gcagatacgc | ggagggcggg | 480 |
| agccgtggcg | ggctggccgg | cgggtaccgg | gtggccgtgt | cggggcgtc | gaccgcgctg | 540 |
| accaagtcgc | tgttccccg | gctgctgcgc | ggggtctccg | acccgatgag | cgggtgcttc | 600 |
| gccatccggc | gggaggcggt | cgaccgcgcc | gtacaggagg | cgagacccg | gcaggaaggg | 660 |
| gggctgcggc | cgctcggcta | caagattctg | ctggagctcg | cggtgcgctg | ccggccgcgc | 720 |
| gggtggtgg | aggtgccgta | cgagttcggg | gagcggttcg | ccggcgagtc | gaagtcgacg | 780 |
| gtgcgcgagg | ggctgcggtt | cctgcggcat | ctggcggagc | tgcggaccag | cgacaagcgg | 840 |
| gcccggatgg | tggccttcgg | gctgatcggg | gtgtcgggct | tcgtaccgaa | tctgctggcg | 900 |
| ctgtgggcgc | tgaccggtgc | cacgaccctg | cattacgcgg | tggcggaggt | gctggccaat | 960 |

| | |
|---|---:|
| cagctcgggg tgctgtggaa cttcgccctg ctggacttcc tggtctaccg gagcgggaaa | 1020 |
| ccggggcgcg gggccggccg gctgctgggg ttcgcgcgc tcagcaacgc ggatctgctg | 1080 |
| gcgcggatcc cgttgatgat gctgttcgtg gagcaggccg ggatgggcc ggtgccggcg | 1140 |
| accgtgatca gtctcgtggt ggtgttcgcg ctgcggttcc tgctggtcga cacgttgatc | 1200 |
| taccggcgca aggggcggc tgccaagcgc gcggcggacg cggcggtcac cggcgggcag | 1260 |
| ggcgagcgcg ctgcttag | 1278 |

<210> SEQ ID NO 11
<211> LENGTH: 1413
<212> TYPE: DNA
<213> ORGANISM: Streptomyces hygroscopicus

<400> SEQUENCE: 11

| | |
|---|---:|
| gtgaccgtcg tgctgctcgc cctgtccgac aggtacggct acaacgtcga cgagctgtat | 60 |
| ttccggctgc tcggcgaaca cggctgggcc tgggctaca ccgaccagcc gccgctggtg | 120 |
| ccggcgctgg tgcacgccac cgcccaggtc ctcggcgact cggtgtgggc gatccgggtg | 180 |
| ccggcggcgc tgtgcgcagg ggccgtggtg ctgctcgggg cgctgatcac cgccgaactc | 240 |
| ggcggcaccc gccgggcaca gactctttcc gccctgggtc tgggcagctc gttcctggtg | 300 |
| ctcagcgtcg gccacatcat ggtgaccacc accctggaca tgctcgcctg gccgcggtg | 360 |
| ctgctcttcg tcctgcgggc gctgctgcgc tcggagggca agtggtggct gtgggcgggg | 420 |
| gtggtgctgg gcctggcgct gtacgccaag tacatcgtgg cgctgctgcc ggtggcgctg | 480 |
| ctggccgggc tcgcgctggt cggtccgcgg aaggtgttcc gtgaccggtg gctgtacgcg | 540 |
| gggatcgcgt tggcgctggc catcggctcg ccgaacctga tctaccaggc cacccatgac | 600 |
| ttcccgcagc tgcagatggc cgatgcgctg ggtgccaccg acggcccgat gaaccgggtc | 660 |
| atcttcgtgc cgagcctggt gatcctgctc ggtccggtgc tgaccgtggt gtgggtcgcg | 720 |
| gggctggtga agctgctgcg tgacccggca tggcggccgg tgcgggcgct ggcaccggcg | 780 |
| ttcgtggtcg gggtggcgct gaccctctac ggcggtggcc ggcccgacta cgtcggcggg | 840 |
| ttcctgatcg ggctgttcgc ggccggggcg gtggccgccg accggtggat ggggcggcgt | 900 |
| acgtcccggc gggtgctgct gtgcgccgga ctggccgcca gtgcggtgct ccaggtgctg | 960 |
| atggcgctgc cggtgctgcc gcagagctcc ccgttcgtgc cgctgaacaa catctccctg | 1020 |
| gagagcgtcg gctggccgcg gctcgccgag caggtgcgca cggcgtacga ggcgctgccg | 1080 |
| cggcagcagc gggagcgggc cgtggtgctc gccgacaacc tcgggagat cggcgcgctg | 1140 |
| gaccgctacg ggcacgggct gcccgcggtg ttcagcggcc acaacgaact gcacaagtgg | 1200 |
| ggcccgccgc cggagcgcgc cgatgtggtg gtcgcggtgg gcgtgccccg gtcccggctg | 1260 |
| gccgcggggt tcacctcgtg caccgtcgtg ggacgggtcg acaacggcgt cggcgtcgag | 1320 |
| aacgccgagc agggcagacc gatcacggtg tgccacggcc gcaaggcttc ctgggcccga | 1380 |
| ctgtggccct cctaccacta cttgagcggc tga | 1413 |

<210> SEQ ID NO 12
<211> LENGTH: 1530
<212> TYPE: DNA
<213> ORGANISM: Streptomyces hygroscopicus

<400> SEQUENCE: 12

| | |
|---|---:|
| atgacgacat ccctcgacag ggattccagg gcggccgcgg ccgggccggg ggtgttccgc | 60 |
| ccggcgccga tggcgtggcg gccggtcgcc gtggtggtgg ccgcgctggc cgtgctgttg | 120 |

-continued

```
ttcgccttcg ccggcgaata cggctaccac gccgacgagt tgtacttccg gctgctcggg      180
gtgcacggct tcgcctgggg ctatgtggac cagccgccgc tgctgccact ggccgtacgg      240
acctcgatgg agatcttcgg cgacagcatg tgggcgatcc gggtgcccgc cgtgctgtgc      300
gcggcggccg tgaccgcgct cggcgcgatg atcgccgccg agctgggcgg ttcccggcgg      360
gcccagacgc tgaccgcgtt cggggtggcc acctcgacga tggtgctcag cttcggccac      420
tggatcctca ccaccagctt cgacaccgtg gcgtgggccg cggtgctgct gttcgtgatg      480
cgggtgctgc tgcgcggcga gagcaagtgg tggctgtggg ccggggtggt ggtcggtgtc      540
gcgctgtacg ccaagtacat cgtgctgctg ctgccggtgg cgctgctggt ggggctggcg      600
ctggtcggtc cgcggaaggt cttccgcgac gggaagctgt acgcgggcac ggcgctggcg      660
ctggtcatcg gctcgccgaa cctgatctac caggccaccc atgacttccc gcagctgcag      720
atggcggagg ggctggcggg caccgacggc gaggcgaacc gcgccatgtt cgccacgaac      780
ctgatcctgc tgttcggccc cgcgctgttc gtgctgtgca tgatcgggct ggtcaagctg      840
ttccgggtgc cggagtggaa gcccgtacgg acactggccg tcggctatct cgcggccacc      900
gcggcgtcgt acctcatcga gggcggccgg ccggactaca ccggcggact gctgatcgcg      960
ctgctggccg ccgggtgtgt gacggccgac cggtgggcgg gcgcccgcaa gctgcggctc     1020
tcggtgctcg cggtctcgct gacgctcagc accgcgtgc agatgctgct gtcgctgccg     1080
gtgatcccca agagctcgct gcgcgacttc cagatcgcca gcatggcgct ggagacggtg     1140
ggctggcccc gtctggtcca gcagaccgag gcggcctacc gcgcactgcc ggccgcggac     1200
cgcgaccgcg cgatcgtgct caccgagaac ttcggcgagg cgggcgccct ggaccactac     1260
gggcacgggc tgccgaaggt gtacagcggc cacaacgagc tgtaccactg gggcccgccg     1320
ccgcagcgcg ccgaggtggt ggtcgcggtg gcatcgacc ggaaccggct gtccgccgac     1380
ttcaccagct gcaaggtcgt cgaccacatc gacaaccgcc tgggcatcga caatccggaa     1440
cagggcgtgc cgatcacggt gtgccacggc cccaagaagc cctggtccgc gctgtggccg     1500
acctaccggc actacaacgc ctatctgtag                                     1530
```

<210> SEQ ID NO 13
<211> LENGTH: 1014
<212> TYPE: DNA
<213> ORGANISM: Streptomyces hygroscopicus

<400> SEQUENCE: 13

```
atgagtaccg aggtttccga ggcgcaggcg cgacgcgccg tggcagacat cttcaactcg       60
acgctggctt cttcggccat cggcgccgcg tgggagctcg gagctcttga cgagctgcgg      120
gagaacggca agttggatgt ctccgatttc gccgtacgcc atgatctgca cgagccggcg      180
gtggtcggca tgttcaccgc gctggcgagt gtgggaatcg tgcggcgcga gggcgccacc      240
gtcgtcgtcg gcccgtactt cgacgaggcc aataccacc gttcactgtt ccactggctc      300
aatcagggca gcggcgagct cttccgccgc atgccgcagg tgctgccgaa cgagaaccgc      360
acaggaaagt tctaccagcg ggacgcgggg gcgatcagct acgcgtgccg cgagatcagc      420
gagcgctatt tcgacccggc gttctgggcc gcgtcgacg tctgggtta caccccccacc      480 accgtcgccg acctggggtc cggcagcggt gagcggctga tccagatcgc ccggcggttc      540
cccggcgtcc gcggcctcgg cgtggacatc gccgacggcg cgatcgccat ggcggagaag      600
gaggtggccg ccaagggatt cggcgaccag atctccttcg tgcggggcga cgcgcgcacc      660
```

| | |
|---|---:|
| atcgaccagg tctcggcgcg cggggaattc gccgaggtcg atctgctcac ctgcttcatg | 720 |
| atggggcacg acttctggcc ccgcgagaac tgtgtgcaga cgctgcgaaa gctgcgcgcg | 780 |
| gcattcccga atgtgcgccg gttcctgctc ggcgacgcca cccgcaccgt cggtatcccc | 840 |
| gaccgcgaac tccccgtatt caccctggga ttcgagttcg gcacgacat gatgggcgtt | 900 |
| tacctgccga ccctcgatga atgggacggg gtattcgaag aggtgggctg cgctgtgtg | 960 |
| aagaagcacg ccatcgactc gctgtcggtc tccgtggtct tcgaactcga gtaa | 1014 |

<210> SEQ ID NO 14
<211> LENGTH: 1320
<212> TYPE: DNA
<213> ORGANISM: Streptomyces hygroscopicus

<400> SEQUENCE: 14

| | |
|---|---:|
| atggaccacg aaagcctgca cagcaccctg accgaactgg cggcccgcca tcgggtgccc | 60 |
| ggcgcgcagc tcgccgtcat ccacgagggg gaacggttcc tggtgcacac cggagtgtgt | 120 |
| gacaccgcct ccggagcccc cgtggagcgg cacaccgcct tccccgtcgg ctcgctgacc | 180 |
| aagccgttca ccgccgccct cgcgatgatc ctggtggccg acggggacgt ggacctggac | 240 |
| gagccgctga gggggcagct gccggagttc ggggcgggcg aactcgtcac cctccggcag | 300 |
| ttgctcagcc acacctcggg cctgccctcc gatgtgccgg agggcagcga cgaggccggc | 360 |
| ggcggcgacc gtgcccgctg gtggcccgg tactgccgta cggcggatct cacgcatgcg | 420 |
| cccgggacgt tcttctcgta ctccaacatc ggctatgtcg tcgtgggccg gctcatcgag | 480 |
| gcggtcaccg gcatgagctg gcaggaggcg atcagcgcga tcctgctcga accctgggc | 540 |
| accggcccg cgttcgtcgt cggagccccc gccaccgtc cggtggccac cgggcacgcc | 600 |
| gtccaggcgg tccgcgaccg ggtggtgccg ataccggacc aggatcttcc cgaggtcgag | 660 |
| atgcccaacg gggcgctggc gctgagcgcc gaggacctgg tcggcttcgc ccggctgtac | 720 |
| ttcgccggct gccccggaccc tcagccgctg gaccgggcga ccgccgacga catgtgcttc | 780 |
| gaccagctgg cctcgatcgc catcggcccg tacggcatgg ccgacggctg ggcctgggc | 840 |
| tgggcgaggt tcgacgacgg tgcggcggac gtctacggcc acaacggcac cggcgacggc | 900 |
| acctcctgtc atctgcgctt cgaccccggc aacggctccg cggtcgcgct gaccgccaac | 960 |
| gccaacaccg gcgcccagct gtgggacgcc ctggtgcccc ggctgcgggc catgggtctg | 1020 |
| gcggtcggcg accgcccggc gcccgagccg cccaccaccc cgccgccggt cccggacgac | 1080 |
| tgtccgggcc gctacaccaa cggcgacacc gagttcgtgg tgcagcccgg cgccgacggc | 1140 |
| gggctgctgc tgagcttcgg cggggcgccc cactcggagc tgctgtgctc ccccgatctg | 1200 |
| cgcttcacca tgcgggagct gggcagcggt gcccggtccc cgggccgctt cgtgaccgat | 1260 |
| cccgccaccg ggcggatcgg ctacctccag atcaccgggc gactcgcccc ccgacgctga | 1320 |

<210> SEQ ID NO 15
<211> LENGTH: 1353
<212> TYPE: DNA
<213> ORGANISM: Streptomyces hygroscopicus

<400> SEQUENCE: 15

| | |
|---|---:|
| atgaccacgg cccccacgga cgcggagacg gcacgcggca gcgcggccgt cccgctgtcc | 60 |
| cgcaaccgcg actacaacat cctgtggtcc agccagctga tgtccgaact cgccatggag | 120 |
| atggccgcg tagccgtgcc gctgctgatc ctcgcccggc acggctcacc gctccagctg | 180 |
| ggcctggcct cctccgcgat ggcggccgcg cacatgatct cggtggtgcc ggccggggtg | 240 |

-continued

```
atcgcggacc gctgggaccg ccgccggctg atgctgggct gccaggtgct acgggtgctg      300
ggcatggtga gcctggccgg cgcgctgctg ctggaccggt acgcgttctg gcatgtgctg      360
ctggtcgtgg tgctggaggg cttcctcggc tcggtcttcg accccgcgga acatgccgcg      420
ctgccccagg tggtgccgcc cgaccagctc tccacggcgg tggccagaaa cgcggcgcgc      480
ccctacatcg ccaccctcgt ggggccgggc gtcgccggtt tcctcttcag cgccctgccg      540
ctcgggccgt tcgcgaccaa tgcggtgatg ttcgcgctgt cgtccgtggc gctgtgcttt      600
ctgcggctgc cccgggggcg gtccgccgtg gtccggaccg cgacgggcc cgacagcgcc       660 ggagcggacc acgacaggcc ggaccacgac ggacgggacg acgcgaacga cgacactgcg      720
ccgcggcccg gggcgccgc ccaggacttc gctgccggct tccgctgggt gctggggcag       780
ccggtgatcc gcaccacgat ggcctggatg atgatcacga acctggtctt cagctcgctg      840
ctgatcgtgc tgctcgcgct tcgggcgag acaaggtcg cgccggtga gctgggtctg         900 acgatggcct gcttcggcgc cggcggactg ctcggcgggc tcttcgcggc ccggatgcac      960
gccgccgccc ggccaccggt gatcctcctc ggcttcacct ggaccgccgc cctgggcgcc      1020
gccctgatgg cggtggtgcc caccggtctg ccccaggag cgctgctcgg cctgatggcg       1080
ctcttcgccc cgctcgccaa caccaccgtg ctgacctacc agttgaccgt caccccggac      1140
gagctgcggg gccggatgag cggcgtcgcc gggttctgct cggggggcgc cggtgtcctg      1200
gggcccgcgc tcggcggtgc gctgacgggg gcggccggcg ggggcgtgac ccccgtactc      1260
atctgcgccg gctgcctggt cctggtcgct gtcgcggcca ccgcgagccc cacgctgcgg      1320
cggtttcccg acatcgcgga ccggcagccc tga                                   1353
```

<210> SEQ ID NO 16
<211> LENGTH: 1227
<212> TYPE: DNA
<213> ORGANISM: Streptomyces hygroscopicus

<400> SEQUENCE: 16

```
atgcagaccc cccacacacc gagccaggca cagtcccagc cacggcaaaa gccgcagccg       60
ccgtcgcagt cgcagtcgca gtcgcagccg aatctgaggt ccctgaccgg attacggttc      120
ctgggcttat tacccgtctt cctcacccat gccgcgttcg agggcgtctt cagcgacgcg      180
gacgtgagct ggggcttcct cgacgcgatg gggaacaccg gctatgccgc ggtctcgttc      240
ttcttcgtgc tgagcggctt tgtgatcacc tggtcctacc gctcccgcga caccaccgc       300 acgttctggc gccgacgcgc cttccgggtc ttccccaacc atctcgtggc ctatgtgttc      360
gcgctggctc tgatgctcgc ggcgggcgcc gccttcgacg ccccgccct gatctcccag       420 atgttcctgg tgcacgcatg ggtgcccgac ccgctgttca tcgacaccgg caacacggtg      480
acctggtccc tcggggtcga tgtggtgttc tacgggctct tcccggtgct gctcgtgctg      540
gtgaacaaga tcaagccaac ccgtttgtgg tactgggccg gtgctgccgt gctcatggtg      600
atcgccatcc ccacagtggc gctgaccctg ctcccggaca ccccgccat gtcggtgggc       660 gatgtctccc gcagccagta ctggttcacc tacttcttcc gctctcccg aaccgtggag       720 tgcgtgctgg gcatgctgat ggcgcggatc gtgctgtccg gcaagtggat aggcctgcgg      780
gtgctgcccg cctcggccct ggtggtcgtg gggtatgtcg tcgcacagca actcccttc       840 ctctaccggc tcagcgcggt gctgatcgtg ccgatcgtgc tgctcaccgc ctccgtggcg      900
gtggccgacg ccgagggccg ggggaccccg ctcggcggca aggtcatggt ccggctcggt      960
```

| | |
|---|---|
| gaactctcct tcgccttcta cctcgtgcac caggcgctcc tggcgtacgg gcacatcctg | 1020 |
| atcagcccga agaacgccca gggcgaggtg ctgccccgta cctgggacac gcctggcggc | 1080 |
| atcgcggtga tcgtcctgtc gttcgtggtg tccctgggac tcgcgtggct gctgcacaac | 1140 |
| ggggtggaga agccggtgat gccgttgg tcccggtcca ggcgccgcgt cacccagcag | 1200 |
| ccgccggcaa aggtgccggc aacttag | 1227 |

<210> SEQ ID NO 17
<211> LENGTH: 1371
<212> TYPE: DNA
<213> ORGANISM: Streptomyces hygroscopicus

<400> SEQUENCE: 17

| | |
|---|---|
| gtgtggagtg cgcgaaagat ctcggccaaa ctccggcgca acgggggagt aaggctgacc | 60 |
| gctgccagaa gtccgcgcgc gccgtggatg tccggtgccg gcgaccacgc ccggatcatc | 120 |
| catcagccga cagtggtgcg gccgccgttg cggcgcaccg agccgcaccg cctgtcgcgc | 180 |
| atctggcgag aggtccgcat gcagacaaga caatccaacc cgaacctgag atccctgacc | 240 |
| ggtttgcggt tcgtggcgat gctgccggtc ttcctcaccc atgcggcgtt cgagggcgtc | 300 |
| ttcagcgacg cgaaggtgag ctggggcttc ctcgacgcga tggggagcac cggctatatg | 360 |
| gccgtctcgt tcttcttcgt gctcagcggc tttgtgatca cgtggtcgta ccggcccacc | 420 |
| gacaccgcgc gcaagttctg gcgccggcgc ttcttccggg tcttccccaa ccacgtcgtg | 480 |
| acctatgcgc tcgccctcgg gctgatcgct gcggtggggc tgagtgtcgg cgtactgccc | 540 |
| tcggtcaccc agctcttcct cgtccagtcc tgggtgcccg accggcgtt caccgacacc | 600 |
| ggcaacagcg tgagctggtc gctcgcggtg gatgtggtgt tctacgcgct cttcccggtg | 660 |
| ctgctcacgc tggtgaacaa gatcaagccg aatcggctct ggtactgggt cggtggctcc | 720 |
| gtcatcggtg tggccgtggt accggccatc gcgctcgccg cgctcccgag cacccccgag | 780 |
| atgccgctcg gcggggtgtc cgtcagccag tactggttca cctacttctt cccgctcttc | 840 |
| cggctgctgg agtgtgtgct cggcatgctg atggcgcgga tcgtgctgtc cggcaagtgg | 900 |
| atacgcctgc gggtgctgcc cgccgccgtc ctcgtggtga tcgcgtacta cttcgcccag | 960 |
| caggtcccgt acctctaccg gctgagtgcg gtgacggtgc tgccggtcgc gctgctgacg | 1020 |
| gcggcggccg cggtggcgga ctccgagggc cggggcaccc tgttcggcag caaggtcatg | 1080 |
| gtctggttcg gcgaactctc cttcgccttc tacctgctgc acaacctcgt cctgaagtac | 1140 |
| ggccatctgc tgctcggcca caccgaggag gagggcgagc tggtgggcca cacctggggc | 1200 |
| gtgcccgagg gaatcgccct gatcgccgcc gccttcgcgg tgtccctgct gctggcctgg | 1260 |
| ctgctgcaca acggagtgga gaagcaggcg atgccgct ggtcccgacg caagccggct | 1320 |
| ccagtggctg aagtaaccag tgggttctat gcgaaggacg gggcaattta g | 1371 |

<210> SEQ ID NO 18
<211> LENGTH: 1026
<212> TYPE: DNA
<213> ORGANISM: Streptomyces hygroscopicus

<400> SEQUENCE: 18

| | |
|---|---|
| gtgctgacgc tccacctgca ggatgacgac gtcgccgcga tcgacgctgt ggctgacgaa | 60 |
| ctcagccggc gatacgactc cgtggagtcc acggagttcc aggccgagag ccgcctctac | 120 |
| gcggacgagt tgccacgtcg cgtgcgacga gcgctgcacg aataccgcag caccgagaag | 180 |
| tccggcatcc tggtcgtcac cggcctgccc gtggacgact cggcgctcgg ggcgaccccg | 240 |

```
gccgaccgcc ggcacaagcc ggtgccgtcc acgtcactgc gccaggacat cgccttctac    300
ctcatagcca atctgctggg cgaccccatc ggctgggcca cccagcagga cggcttcatc    360
atgcatgacg tctaccccgt ccagggcttc gagcacgaac agatcggctg ggcagcgag     420 gagacgctca cctggcacac cgaggacgcc ttccatccgc tgcgcacgga ctatctcgga    480
ctgatgtgtc tgcgcaatcc ggacggcgtc gagaccaccg cctgcgatat cgccgatgtc    540
gagatcgacg acgagacccg ggagaccctc tcgcaggagc gcttccggat cctgccggac    600
gacgcgcacc gcatccacgg caaggccccg ggggacgaga gcgcacgcga gagtgcgctg    660
cgtgagcgca gccggcagcg ggtggcctcg gccctggagt cgcccgaccc ggtggccgtg    720
ctcttcgggg accgcgacga cccgtatctg cggatcgacc gcactacat gcagggcgtc     780 cagggcgaga ccgagcagcg ggcgctggag accatcggcg ccgcgatcga cgacgccatg    840
tccggtgtcg tgctcagccc cggtgacatc gttttcatcg acaactaccg cgtcgtccac    900
ggacgtaagc cgttccgtgc ccgcttcgac ggtacggacc gctggctgcg gcggctcaac    960
atcgcccggg acctgcgcaa gtcgcgcgag gccaggctcg ccgccaccac ccgcgtcatc   1020
tactga                                                             1026
```

<210> SEQ ID NO 19
<211> LENGTH: 28
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(32)
<223> OTHER INFORMATION: where n is inosine

<400> SEQUENCE: 19
acstcsggcw cgcaccggcc ngccsaag                                         28

<210> SEQ ID NO 20
<211> LENGTH: 32
<212> TYPE: DNA
<213> ORGANISM: Artificial Sequence
<220> FEATURE:
<223> OTHER INFORMATION: PCR primer

<400> SEQUENCE: 20
agctcsaysc gstagccscg saycttsacc tg                                    32

<210> SEQ ID NO 21
<211> LENGTH: 323
<212> TYPE: PRT
<213> ORGANISM: Streptomyces hygroscopicus

<400> SEQUENCE: 21

Met Ser Ala Thr Pro Arg Pro Arg Pro Val Leu Arg Pro Phe Arg Pro
1               5                   10                  15

Gly Asp Gly Arg Ser Leu Leu Ala Ala Trp Cys Arg Ser Ala Pro Asp
            20                  25                  30

Asp Pro Ile Thr Ala Ala Arg Phe Arg Thr Leu Ile Leu Leu Asp Pro
        35                  40                  45

Asn Phe Asp Pro Glu Gly Leu Arg Val Ala Asp Leu Asp Gly Gln Val
    50                  55                  60

Val Gly Ala Val Tyr Ala Val Arg Arg Thr Pro Leu Ala Gly Thr
65                  70                  75                  80

```
Asp Leu Glu Pro Asp Val Gly Trp Ile Leu Phe Phe Val Asp Pro
                85                  90                  95

Pro His Arg Arg Thr Gly Leu Gly Arg Arg Leu Leu Thr Asp Ala Leu
                100                 105                 110

Asp Trp Leu Arg Gly His Gly Arg Thr Arg Val Asp Phe Ala Pro Tyr
            115                 120                 125

Ala Pro His Tyr Val Leu Pro Gly Leu Asp Arg Ala Ala Tyr Pro Glu
        130                 135                 140

Ala Ala Arg Leu Leu Ala Ser Leu Gly Phe Arg Pro Arg Tyr Glu Ala
145                 150                 155                 160

Ala Ala Met Asp Arg Gly Leu Val Gly Tyr Arg Met Pro Asp Glu Val
                165                 170                 175

Arg Arg His Glu Ala Ala Leu Thr Ala Arg Gly His Arg Phe Gly Thr
                180                 185                 190

Pro Ser Asp Asp Asp Leu Val Asp Leu Leu Gly Leu Ala Glu Glu Phe
            195                 200                 205

Thr Pro Asp Trp Ala Arg Ala Ile Arg Gln Cys Leu Thr Gly Gly Ala
        210                 215                 220

Pro Leu Asp Arg Ile Val Ser Ala Arg Ala Pro Asp Gly Arg Met Ala
225                 230                 235                 240

Gly Trp Ala Met His Gly Ala Tyr Asp Gly Thr Ala Glu Arg Phe Gly
                245                 250                 255

Pro Phe Gly Val Arg Lys Glu Leu Arg Gly Ala Gly Leu Gly Lys Val
                260                 265                 270

Leu Leu His Leu Thr Leu Glu Arg Met Arg Ala Leu Gly Val His Gly
            275                 280                 285

Ala Trp Phe Leu Trp Thr Gly Glu Gln Ser Pro Ala Gly His Leu Tyr
        290                 295                 300

Arg Ala Ser Gly Phe Thr Thr Thr Arg Arg Phe Thr Val Leu Arg Trp
305                 310                 315                 320

Glu Ala Gly

<210> SEQ ID NO 22
<211> LENGTH: 471
<212> TYPE: PRT
<213> ORGANISM: Streptomyces hygroscopicus

<400> SEQUENCE: 22

Met Arg Arg Arg Thr Phe Thr Ala Gly Ala Ala Ala Gly Ala Ala Leu
1               5                   10                  15

Leu Ala Gly Ala Gly Cys Asp Ala Pro Gly Gly Ala Gly His Gly Asp
                20                  25                  30

Gly Glu His Gly Asp Gly Asp Gly Gly Asp Gly Arg Gly Ser Gly Gly
            35                  40                  45

Arg Arg Gly Ala Pro Val Thr Leu Thr Val Leu Thr His Tyr Ala Ser
        50                  55                  60

Glu Pro Leu Ala Ser Ala Leu Gln Thr Val Val Asp Ala Trp Asn Ala
65                  70                  75                  80

Thr His Arg Arg Ile Thr Val Arg Thr Ala Ala Val Lys Phe Pro Asp
                85                  90                  95

Leu Leu Thr Thr Tyr Met Val Arg Gln Ala Ala Gly Gln Gly Ala Asp
                100                 105                 110

Ile Ile His Pro Tyr Cys Leu Trp Thr Gly Gln Leu Val Arg Ala Gly
            115                 120                 125
```

```
Val Leu Arg Pro Val Pro Pro Thr Ala Thr Arg Gln Ile Arg Arg Asp
    130                 135                 140

Phe Thr Pro Ala Ala Val Ala Ala Ser Ser Val His Gly Thr Leu Tyr
145                 150                 155                 160

Gly Tyr Pro Thr Glu Val Gln Thr Tyr Ala Leu Tyr Asn Lys Arg
                165                 170                 175

Leu Leu Arg Gln Ala Gly Ile Asp Gly Pro Gly Thr Trp Gln Glu
            180                 185                 190

Leu Glu Asp Ala Ala Tyr Arg Thr Ala Arg Arg Asp Arg His Gly Asn
            195                 200                 205

Met Leu Val Gln Gly Phe Gly Leu Ser Arg Ala Asp Asp Ala Ser Val
    210                 215                 220

Val Gly Gln Thr Leu Ala Leu Leu Ala Ala Arg Gly Gly Thr Phe Leu
225                 230                 235                 240

Thr Ser Asp Gly Arg Arg Thr Ala Ile Gly Ser Ala Ala Gly Arg Asp
                245                 250                 255

Val Leu Asp Leu Glu Arg Arg Leu Ile Asp Arg Gly Ala Ala Asp Ser
            260                 265                 270

Gly Ile Ser Leu Leu Arg Ala Phe Pro Ser Gly Gln Val Ala Met Ala
        275                 280                 285

Ile Asn Ala Gly Trp Trp Thr Ala Ser Leu Arg Gly Ala Met Gly Ala
    290                 295                 300

Asp Tyr Arg Glu Val Gly Val Ala Pro Val Pro Gly Pro Ala Pro Asp
305                 310                 315                 320

Asp Arg Gly Thr Leu Ala Thr Gly Phe Leu Leu Gly Val Asn Ala Lys
                325                 330                 335

Ser Arg Tyr Pro Gly Glu Ala Trp Glu Phe Leu His Trp Leu Asn Gly
            340                 345                 350

Val Arg Ala Pro Ala Ala Arg Pro Gly Arg Ser Ala Gly Gly Val
        355                 360                 365

Pro Val Ser Arg Met Ser Ala Leu Gln Val Ser Val Gly Ser Met Thr
    370                 375                 380

Gly Arg Ala Asp Asp Met Arg Ala Leu Leu Gly Gly Asp Gly Glu Arg
385                 390                 395                 400

Asp Ala Asp Gly Arg Gly Gly Asp Arg Asn Leu Gly Pro Phe Leu
                405                 410                 415

Asp Ala Leu Arg Tyr Ala Val Pro Glu Pro Asn Gly Pro Arg Ala Gln
            420                 425                 430

Gln Ala Lys Ser Leu Leu Arg Lys Asn Ile Glu Asp Val Trp Thr Gly
        435                 440                 445

Arg Ala Ser Val Asp Ala Ala Leu Arg Thr Ala Gly Arg Gln Ile Asp
    450                 455                 460

Gln Glu Leu Ser Arg Pro Tyr
465                 470

<210> SEQ ID NO 23
<211> LENGTH: 303
<212> TYPE: PRT
<213> ORGANISM: Streptomyces hygroscopicus

<400> SEQUENCE: 23

Met Ala Ser Ala Gly Gly Gly Pro Val Arg Ala Ala Arg Arg Gln
1               5                   10                  15

Thr Ala Val Ala Tyr Leu Phe Leu Thr Pro Ala Leu Leu Phe Phe Ala
```

-continued

```
                  20                  25                  30
Val Phe Leu Ala Leu Pro Leu Leu Phe Ala Val Leu Leu Ala Gln Ser
            35                  40                  45
Arg Trp Ala Gly Phe Asp Leu Ala Asp Ile Glu Pro Val Gly Met Ala
        50                  55                  60
Asn Phe Thr Asp Leu Phe Ala Arg Gly Ser Thr Phe Leu Thr Pro Val
 65                  70                  75                  80
Leu Thr Asn Thr Leu Leu Tyr Ala Val Gly Thr Val Ala Ile Ala Leu
                85                  90                  95
Ile Gly Ala Leu Thr Leu Ala Thr Cys Ile Asp Asn Leu Arg Phe Gln
            100                 105                 110
Gly Leu Trp Arg Thr Leu Tyr Phe Leu Pro Ile Val Thr Thr Val Val
        115                 120                 125
Ala Val Gly Asn Val Trp Lys Tyr Met Tyr Ala Pro Gly Gly Leu Ile
130                 135                 140
Asn Gly Val Leu Asn Gly Leu Gly Leu His Ser Val Ala Phe Leu Gln
145                 150                 155                 160
Asp Pro Gly Thr Ala Leu Pro Ser Val Val Val Gln Ala Trp Ala
            165                 170                 175
Ser Met Gly Thr Ala Ile Leu Ile Leu Thr Ala Gly Leu Lys Ser Ile
                180                 185                 190
Pro Glu Ala Tyr Tyr Glu Ala Ala Glu Leu Asp Gly Ala Gly Ala Gly
            195                 200                 205
Thr Val Phe Arg Arg Ile Thr Leu Pro Leu Leu Arg Pro Ser Leu Leu
        210                 215                 220
Phe Val Cys Ile Thr Gln Phe Ile Thr Gly Leu Gln Ser Phe Ala Leu
225                 230                 235                 240
Ile Asn Val Met Thr Asp Asp Gly Pro Gly Asp Ala Thr Asn Val
                245                 250                 255
Ala Ala Leu Glu Met Tyr Gln Gln Ala Phe Arg Tyr Gly Asp Trp Gly
            260                 265                 270
Ile Ala Ser Ala Ala Phe Val Leu Phe Leu Val Ile Val Ala Ile
        275                 280                 285
Thr Val Gly Gln Leu Trp Leu Phe Arg Arg Lys Gly Gly Glu Ser
    290                 295                 300

<210> SEQ ID NO 24
<211> LENGTH: 296
<212> TYPE: PRT
<213> ORGANISM: Streptomyces hygroscopicus

<400> SEQUENCE: 24

Val Ser Arg Ser Ala Arg Arg Pro Gly Arg Arg Pro Trp Gly
 1               5                  10                  15
Ser Tyr Ala Val Val Ala Gly Ala Ala Leu Thr Leu Val Pro Phe
                20                  25                  30
Leu Asp Met Leu Leu Thr Ser Phe Lys Gly Pro Gly Glu Tyr Gly Lys
            35                  40                  45
Leu Pro Tyr Arg Phe Leu Pro Gln Ala Phe Asp Leu Ser Asn Tyr Arg
        50                  55                  60
Ala Ala Met Glu Gln Leu Asp Leu Pro Leu Phe Arg Asn Ser Val
 65                  70                  75                  80
Ile Ala Thr Ala Val Ile Thr Gly Ser Ile Leu Val Thr Ser Ala Leu
                85                  90                  95
```

```
Ala Gly Tyr Ala Leu Ala Lys Leu Arg Phe Pro Gly Arg Glu Val Ile
            100                 105                 110

Phe Arg Leu Val Leu Ser Thr Met Met Phe Pro Pro Phe Leu Phe Phe
        115                 120                 125

Ile Pro His Phe Leu Ile Leu Val His Trp Pro Gly Ala Gly Gly Asn
    130                 135                 140

Asp Leu Leu Gly Arg Gly Gly Ala Gly Leu Thr Val Ser Leu Ala Ala
145                 150                 155                 160

Leu Val Met Pro Phe Leu Val Ser Gly Phe Gly Ile Phe Leu Met Arg
                165                 170                 175

Gln Phe Met Val Ser Ile Pro Asp Glu Leu Leu Glu Ala Ala Arg Ile
            180                 185                 190

Asp Gly Ala Gly Glu Phe Ala Leu Trp Trp Arg Ile Val Leu Pro Gln
        195                 200                 205

Thr Lys Pro Val Ala Val Thr Leu Ala Leu Leu Thr Phe Val Asn Ala
    210                 215                 220

Trp Asn Glu Tyr Ile Trp Ala Leu Leu Ile Ser Thr Ala Asn Pro Arg
225                 230                 235                 240

Leu Met Thr Leu Pro Val Gly Ile Gln Met Leu Gln Ser Tyr Leu Asp
                245                 250                 255

Pro Asp Arg Met Val Pro Val Met Met Ala Gly Leu Val Leu Ser Ile
            260                 265                 270

Leu Pro Val Leu Leu Leu Phe Leu Leu Gln Lys His Tyr Leu Arg
        275                 280                 285

Gly Val Met Leu Ser Gly Leu Lys
    290                 295

<210> SEQ ID NO 25
<211> LENGTH: 425
<212> TYPE: PRT
<213> ORGANISM: Streptomyces hygroscopicus

<400> SEQUENCE: 25

Met Ser Ser Gly Phe Ser Trp Ala Val Ala Thr Val Val Arg Val
1               5                   10                  15

Ser Asp Pro Ser Gly Gly Thr Met Ala Ser Asp Ser Ser Pro Thr
                20                  25                  30

Pro Met Pro Ala Val Ser Leu Ile Val Pro Thr Phe Asn Glu Ala Ala
        35                  40                  45

Asn Ile Asp Glu Leu Leu Asp Gly Val Cys Ala Ala Ile Pro Ala Gly
    50                  55                  60

Leu Glu Val Glu Val Leu Phe Val Asp Asp Ser Thr Asp Thr Pro
65                  70                  75                  80

Glu Val Ile Glu Lys Ala Ala Ala Arg Cys Pro Met Pro Val Ser Val
                85                  90                  95

Leu His Arg Glu Val Pro Gly Gly Leu Gly Gly Ala Val Val Ala
            100                 105                 110

Gly Ile Ala Arg Thr Ser Ala Pro Trp Ile Met Val Met Asp Ala Asp
        115                 120                 125

Leu Gln His Pro Pro Glu Leu Leu Pro Gln Leu Ile Glu Ala Gly Glu
    130                 135                 140

Arg Ala Ala Ala Glu Leu Val Val Ala Ser Arg Tyr Ala Glu Gly Gly
145                 150                 155                 160

Ser Arg Gly Gly Leu Ala Gly Gly Tyr Arg Val Ala Val Ser Gly Ala
                165                 170                 175
```

```
Ser Thr Ala Leu Thr Lys Ser Leu Phe Pro Arg Leu Leu Arg Gly Val
            180                 185                 190

Ser Asp Pro Met Ser Gly Cys Phe Ala Ile Arg Arg Glu Ala Val Asp
        195                 200                 205

Arg Ala Val Gln Glu Gly Glu Thr Arg Gln Glu Gly Gly Leu Arg Pro
    210                 215                 220

Leu Gly Tyr Lys Ile Leu Glu Leu Ala Val Arg Cys Arg Pro Arg
225                 230                 235                 240

Gly Val Val Glu Val Pro Tyr Glu Phe Gly Glu Arg Phe Ala Gly Glu
                245                 250                 255

Ser Lys Ser Thr Val Arg Glu Gly Leu Arg Phe Leu Arg His Leu Ala
            260                 265                 270

Glu Leu Arg Thr Ser Asp Lys Arg Ala Arg Met Val Ala Phe Gly Leu
        275                 280                 285

Ile Gly Val Ser Gly Phe Val Pro Asn Leu Leu Ala Leu Trp Ala Leu
    290                 295                 300

Thr Gly Ala Thr Thr Leu His Tyr Ala Val Ala Glu Val Leu Ala Asn
305                 310                 315                 320

Gln Leu Gly Val Leu Trp Asn Phe Ala Leu Leu Asp Phe Leu Val Tyr
                325                 330                 335

Arg Ser Gly Lys Pro Gly Arg Gly Ala Gly Arg Leu Leu Gly Phe Ala
            340                 345                 350

Ala Leu Ser Asn Ala Asp Leu Leu Ala Arg Ile Pro Leu Met Met Leu
        355                 360                 365

Phe Val Glu Gln Ala Gly Met Gly Pro Val Pro Ala Thr Val Ile Ser
    370                 375                 380

Leu Val Val Phe Ala Leu Arg Phe Leu Leu Val Asp Thr Leu Ile
385                 390                 395                 400

Tyr Arg Arg Lys Gly Ala Ala Ala Lys Arg Ala Ala Asp Ala Ala Val
                405                 410                 415

Thr Gly Gly Gln Gly Glu Arg Ala Ala
            420                 425

<210> SEQ ID NO 26
<211> LENGTH: 470
<212> TYPE: PRT
<213> ORGANISM: Streptomyces hygroscopicus

<400> SEQUENCE: 26

Val Thr Val Val Leu Ala Leu Ser Asp Arg Tyr Gly Tyr Asn Val
1               5                   10                  15

Asp Glu Leu Tyr Phe Arg Leu Leu Gly Glu His Gly Trp Ala Trp Gly
            20                  25                  30

Tyr Thr Asp Gln Pro Pro Leu Val Pro Ala Leu Val His Ala Thr Ala
        35                  40                  45

Gln Val Leu Gly Asp Ser Val Trp Ala Ile Arg Val Pro Ala Ala Leu
    50                  55                  60

Cys Ala Gly Ala Val Leu Leu Gly Ala Leu Ile Thr Ala Glu Leu
65                  70                  75                  80

Gly Gly Thr Arg Arg Ala Gln Thr Leu Ser Ala Leu Gly Leu Gly Ser
                85                  90                  95

Ser Phe Leu Val Leu Ser Val Gly His Ile Met Val Thr Thr Thr Leu
            100                 105                 110

Asp Met Leu Ala Trp Ala Ala Val Leu Leu Phe Val Leu Arg Ala Leu
```

```
                115                 120                 125
Leu Arg Ser Glu Gly Lys Trp Trp Leu Trp Ala Gly Val Leu Gly
    130                 135                 140

Leu Ala Leu Tyr Ala Lys Tyr Ile Val Ala Leu Leu Pro Val Ala Leu
145                 150                 155                 160

Leu Ala Gly Leu Ala Leu Val Gly Pro Arg Lys Val Phe Arg Asp Arg
                165                 170                 175

Trp Leu Tyr Ala Gly Ile Ala Leu Ala Leu Ala Ile Gly Ser Pro Asn
            180                 185                 190

Leu Ile Tyr Gln Ala Thr His Asp Phe Pro Gln Leu Gln Met Ala Asp
        195                 200                 205

Ala Leu Gly Ala Thr Asp Gly Pro Met Asn Arg Val Ile Phe Val Pro
    210                 215                 220

Ser Leu Val Ile Leu Leu Gly Pro Val Leu Thr Val Val Trp Val Ala
225                 230                 235                 240

Gly Leu Val Lys Leu Leu Arg Asp Pro Ala Trp Arg Pro Val Arg Ala
                245                 250                 255

Leu Ala Pro Ala Phe Val Val Gly Val Ala Leu Thr Leu Tyr Gly Gly
            260                 265                 270

Gly Arg Pro Asp Tyr Val Gly Gly Phe Leu Ile Gly Leu Phe Ala Ala
        275                 280                 285

Gly Ala Val Ala Ala Asp Arg Trp Met Gly Arg Arg Thr Ser Arg Arg
    290                 295                 300

Val Leu Leu Cys Ala Gly Leu Ala Ala Ser Ala Val Leu Gln Val Leu
305                 310                 315                 320

Met Ala Leu Pro Val Leu Pro Gln Ser Ser Pro Phe Val Pro Leu Asn
                325                 330                 335

Asn Ile Ser Leu Glu Ser Val Gly Trp Pro Arg Leu Ala Glu Gln Val
            340                 345                 350

Arg Thr Ala Tyr Glu Ala Leu Pro Arg Gln Arg Glu Arg Ala Val
        355                 360                 365

Val Leu Ala Asp Asn Leu Gly Glu Ile Gly Ala Leu Asp Arg Tyr Gly
    370                 375                 380

His Gly Leu Pro Ala Val Phe Ser Gly His Asn Glu Leu His Lys Trp
385                 390                 395                 400

Gly Pro Pro Pro Glu Arg Ala Asp Val Val Ala Val Gly Val Pro
                405                 410                 415

Arg Ser Arg Leu Ala Ala Gly Phe Thr Ser Cys Thr Val Val Gly Arg
            420                 425                 430

Val Asp Asn Gly Val Gly Val Glu Asn Ala Glu Gln Gly Arg Pro Ile
        435                 440                 445

Thr Val Cys His Gly Arg Lys Ala Ser Trp Ala Arg Leu Trp Pro Ser
    450                 455                 460

Tyr His Tyr Leu Ser Gly
465                 470

<210> SEQ ID NO 27
<211> LENGTH: 509
<212> TYPE: PRT
<213> ORGANISM: Streptomyces hygroscopicus

<400> SEQUENCE: 27

Met Thr Thr Ser Leu Asp Arg Asp Ser Arg Ala Ala Ala Gly Pro
1               5                   10                  15
```

```
Gly Val Phe Arg Pro Ala Pro Met Ala Trp Arg Pro Val Ala Val Val
            20                  25                  30

Val Ala Ala Leu Ala Val Leu Leu Phe Ala Phe Ala Gly Glu Tyr Gly
        35                  40                  45

Tyr His Ala Asp Glu Leu Tyr Phe Arg Leu Leu Gly Val His Gly Phe
    50                  55                  60

Ala Trp Gly Tyr Val Asp Gln Pro Pro Leu Leu Pro Leu Ala Val Arg
65                  70                  75                  80

Thr Ser Met Glu Ile Phe Gly Asp Ser Met Trp Ala Ile Arg Val Pro
                85                  90                  95

Ala Val Leu Cys Ala Ala Val Thr Ala Leu Gly Ala Met Ile Ala
                100                 105                 110

Ala Glu Leu Gly Gly Ser Arg Arg Ala Gln Thr Leu Thr Ala Phe Gly
            115                 120                 125

Val Ala Thr Ser Thr Met Val Leu Ser Phe Gly His Trp Ile Leu Thr
        130                 135                 140

Thr Ser Phe Asp Thr Val Ala Trp Ala Ala Val Leu Leu Phe Val Met
145                 150                 155                 160

Arg Val Leu Leu Arg Gly Glu Ser Lys Trp Trp Leu Trp Ala Gly Val
                165                 170                 175

Val Val Gly Val Ala Leu Tyr Ala Lys Tyr Ile Val Leu Leu Leu Pro
            180                 185                 190

Val Ala Leu Leu Val Gly Leu Ala Leu Val Gly Pro Arg Lys Val Phe
        195                 200                 205

Arg Asp Gly Lys Leu Tyr Ala Gly Thr Ala Leu Ala Leu Val Ile Gly
210                 215                 220

Ser Pro Asn Leu Ile Tyr Gln Ala Thr His Asp Phe Pro Gln Leu Gln
225                 230                 235                 240

Met Ala Glu Gly Leu Ala Gly Thr Asp Gly Glu Ala Asn Arg Ala Met
                245                 250                 255

Phe Ala Thr Asn Leu Ile Leu Leu Phe Gly Pro Ala Leu Phe Val Leu
            260                 265                 270

Cys Met Ile Gly Leu Val Lys Leu Phe Arg Val Pro Glu Trp Lys Pro
        275                 280                 285

Val Arg Thr Leu Ala Val Gly Tyr Leu Ala Ala Thr Ala Ala Ser Tyr
290                 295                 300

Leu Ile Glu Gly Gly Arg Pro Asp Tyr Thr Gly Gly Leu Leu Ile Ala
305                 310                 315                 320

Leu Leu Ala Ala Gly Cys Val Thr Ala Asp Arg Trp Ala Gly Ala Arg
                325                 330                 335

Lys Leu Arg Leu Ser Val Leu Ala Val Ser Leu Thr Leu Ser Thr Ala
            340                 345                 350

Val Gln Met Leu Leu Ser Leu Pro Val Ile Pro Lys Ser Ser Leu Arg
        355                 360                 365

Asp Phe Gln Ile Ala Ser Met Ala Leu Glu Thr Val Gly Trp Pro Arg
370                 375                 380

Leu Val Gln Gln Thr Glu Ala Ala Tyr Arg Ala Leu Pro Ala Ala Asp
385                 390                 395                 400

Arg Asp Arg Ala Ile Val Leu Thr Glu Asn Phe Gly Glu Ala Gly Ala
                405                 410                 415

Leu Asp His Tyr Gly His Gly Leu Pro Lys Val Tyr Ser Gly His Asn
            420                 425                 430

Glu Leu Tyr His Trp Gly Pro Pro Pro Gln Arg Ala Glu Val Val Val
```

```
            435                 440                 445
Ala Val Gly Ile Asp Arg Asn Arg Leu Ser Ala Asp Phe Thr Ser Cys
    450                 455                 460

Lys Val Asp His Ile Asp Asn Arg Leu Gly Ile Asp Asn Pro Glu
465                 470                 475                 480

Gln Gly Val Pro Ile Thr Val Cys His Gly Pro Lys Lys Pro Trp Ser
                485                 490                 495

Ala Leu Trp Pro Thr Tyr Arg His Tyr Asn Ala Tyr Leu
            500                 505

<210> SEQ ID NO 28
<211> LENGTH: 337
<212> TYPE: PRT
<213> ORGANISM: Streptomyces hygroscopicus

<400> SEQUENCE: 28

Met Ser Thr Glu Val Ser Glu Ala Gln Ala Arg Arg Ala Val Ala Asp
1               5                   10                  15

Ile Phe Asn Ser Thr Leu Ala Ser Ser Ala Ile Gly Ala Ala Trp Glu
                20                  25                  30

Leu Gly Ala Leu Asp Glu Leu Arg Glu Asn Gly Lys Leu Asp Val Ser
            35                  40                  45

Asp Phe Ala Val Arg His Asp Leu His Glu Pro Ala Val Val Gly Met
    50                  55                  60

Phe Thr Ala Leu Ala Ser Val Gly Ile Val Arg Arg Glu Gly Ala Thr
65                  70                  75                  80

Val Val Val Gly Pro Tyr Phe Asp Glu Ala Asn His His Arg Ser Leu
                85                  90                  95

Phe His Trp Leu Asn Gln Gly Ser Gly Glu Leu Phe Arg Arg Met Pro
            100                 105                 110

Gln Val Leu Pro Asn Glu Asn Arg Thr Gly Lys Phe Tyr Gln Arg Asp
        115                 120                 125

Ala Gly Ala Ile Ser Tyr Ala Cys Arg Glu Ile Ser Glu Arg Tyr Phe
    130                 135                 140

Asp Pro Ala Phe Trp Ala Ala Val Asp Gly Leu Gly Tyr Thr Pro Thr
145                 150                 155                 160

Thr Val Ala Asp Leu Gly Ser Gly Ser Gly Glu Arg Leu Ile Gln Ile
                165                 170                 175

Ala Arg Arg Phe Pro Gly Val Arg Gly Leu Gly Val Asp Ile Ala Asp
            180                 185                 190

Gly Ala Ile Ala Met Ala Glu Lys Glu Val Ala Ala Lys Gly Phe Gly
        195                 200                 205

Asp Gln Ile Ser Phe Val Arg Gly Asp Ala Arg Thr Ile Asp Gln Val
    210                 215                 220

Ser Ala Arg Gly Glu Phe Ala Glu Val Asp Leu Leu Thr Cys Phe Met
225                 230                 235                 240

Met Gly His Asp Phe Trp Pro Arg Glu Asn Cys Val Gln Thr Leu Arg
                245                 250                 255

Lys Leu Arg Ala Ala Phe Pro Asn Val Arg Arg Phe Leu Leu Gly Asp
            260                 265                 270

Ala Thr Arg Thr Val Gly Ile Pro Asp Arg Glu Leu Pro Val Phe Thr
        275                 280                 285

Leu Gly Phe Glu Phe Gly His Asp Met Met Gly Val Tyr Leu Pro Thr
    290                 295                 300
```

```
Leu Asp Glu Trp Asp Gly Val Phe Glu Glu Gly Gly Trp Arg Cys Val
305                 310                 315                 320

Lys Lys His Ala Ile Asp Ser Leu Ser Val Ser Val Phe Glu Leu
                325                 330                 335

Glu
```

<210> SEQ ID NO 29
<211> LENGTH: 439
<212> TYPE: PRT
<213> ORGANISM: Streptomyces hygroscopicus

<400> SEQUENCE: 29

```
Met Asp His Glu Ser Leu His Ser Thr Leu Thr Glu Leu Ala Ala Arg
1               5                   10                  15

His Arg Val Pro Gly Ala Gln Leu Ala Val Ile His Glu Gly Glu Arg
                20                  25                  30

Phe Leu Val His Thr Gly Val Cys Asp Thr Ala Ser Gly Ala Pro Val
            35                  40                  45

Glu Arg His Thr Ala Phe Pro Val Gly Ser Leu Thr Lys Pro Phe Thr
50                  55                  60

Ala Ala Leu Ala Met Ile Leu Val Ala Asp Gly Asp Val Asp Leu Asp
65                  70                  75                  80

Glu Pro Leu Arg Gly Gln Leu Pro Glu Phe Ala Gly Glu Leu Val
                85                  90                  95

Thr Leu Arg Gln Leu Leu Ser His Thr Ser Gly Leu Pro Ser Asp Val
                100                 105                 110

Pro Glu Gly Ser Asp Glu Ala Gly Gly Asp Arg Ala Arg Trp Val
                115                 120                 125

Ala Arg Tyr Cys Arg Thr Ala Asp Leu Thr His Ala Pro Gly Thr Val
            130                 135                 140

Phe Ser Tyr Ser Asn Ile Gly Tyr Val Val Gly Arg Leu Ile Glu
145                 150                 155                 160

Ala Val Thr Gly Met Ser Trp Gln Glu Ala Ile Ser Ala Ile Leu Leu
                165                 170                 175

Glu Pro Leu Gly Thr Arg Pro Ala Phe Val Val Gly Ala Pro Ala Thr
                180                 185                 190

Arg Pro Val Ala Thr Gly His Ala Val Gln Ala Val Arg Asp Arg Val
            195                 200                 205

Val Pro Ile Pro Asp Gln Asp Leu Pro Glu Val Glu Met Pro Asn Gly
210                 215                 220

Ala Leu Ala Leu Ser Ala Glu Asp Leu Val Gly Phe Ala Arg Leu Tyr
225                 230                 235                 240

Phe Ala Gly Cys Pro Asp Pro Gln Pro Leu Asp Arg Ala Thr Ala Asp
                245                 250                 255

Asp Met Cys Phe Asp Gln Leu Ala Ser Ile Ala Ile Gly Pro Tyr Gly
                260                 265                 270

Met Ala Asp Gly Trp Gly Leu Gly Trp Ala Arg Phe Asp Asp Gly Ala
            275                 280                 285

Ala Asp Val Tyr Gly His Asn Gly Thr Gly Asp Gly Thr Ser Cys His
290                 295                 300

Leu Arg Phe Asp Pro Ala Asn Gly Ser Ala Val Ala Leu Thr Ala Asn
305                 310                 315                 320

Ala Asn Thr Gly Ala Gln Leu Trp Asp Ala Leu Val Pro Arg Leu Arg
                325                 330                 335
```

```
Ala Met Gly Leu Ala Val Gly Asp Arg Pro Ala Pro Glu Pro Pro Thr
            340                 345                 350

Thr Pro Pro Val Pro Asp Asp Cys Pro Gly Arg Tyr Thr Asn Gly
        355                 360                 365

Asp Thr Glu Phe Val Val Gln Pro Gly Ala Asp Gly Gly Leu Leu Leu
    370                 375                 380

Ser Phe Gly Gly Ala Pro His Ser Glu Leu Leu Cys Ser Pro Asp Leu
385                 390                 395                 400

Arg Phe Thr Met Arg Glu Leu Gly Ser Gly Ala Arg Ser Pro Gly Arg
                405                 410                 415

Phe Val Thr Asp Pro Ala Thr Gly Arg Ile Gly Tyr Leu Gln Ile Thr
                420                 425                 430

Gly Arg Leu Ala Pro Arg Arg
        435

<210> SEQ ID NO 30
<211> LENGTH: 450
<212> TYPE: PRT
<213> ORGANISM: Streptomyces hygroscopicus

<400> SEQUENCE: 30

Met Thr Thr Ala Pro Thr Asp Ala Glu Thr Ala Arg Gly Ser Ala Ala
1               5                   10                  15

Val Pro Leu Ser Arg Asn Arg Asp Tyr Asn Ile Leu Trp Ser Ser Gln
            20                  25                  30

Leu Met Ser Glu Leu Ala Met Glu Met Ala Ala Val Ala Val Pro Leu
        35                  40                  45

Leu Ile Leu Ala Arg His Gly Ser Pro Leu Gln Leu Gly Leu Ala Ser
    50                  55                  60

Ser Ala Met Ala Ala His Met Ile Ser Val Val Pro Ala Gly Val
65                  70                  75                  80

Ile Ala Asp Arg Trp Asp Arg Arg Leu Met Leu Gly Cys Gln Val
                85                  90                  95

Leu Arg Val Leu Gly Met Val Ser Leu Ala Gly Ala Leu Leu Leu Asp
            100                 105                 110

Arg Tyr Ala Phe Trp His Val Leu Leu Val Val Val Leu Glu Gly Phe
        115                 120                 125

Leu Gly Ser Val Phe Asp Pro Ala Glu His Ala Ala Leu Pro Gln Val
    130                 135                 140

Val Pro Pro Asp Gln Leu Ser Thr Ala Val Ala Arg Asn Ala Ala Arg
145                 150                 155                 160

Pro Tyr Ile Ala Thr Leu Val Gly Pro Gly Val Ala Gly Phe Leu Phe
                165                 170                 175

Ser Ala Leu Pro Leu Gly Pro Phe Ala Thr Asn Ala Val Met Phe Ala
            180                 185                 190

Leu Ser Ser Val Ala Leu Cys Phe Leu Arg Leu Pro Arg Gly Arg Ser
        195                 200                 205

Ala Val Val Arg Thr Gly Asp Gly Pro Asp Ser Ala Gly Ala Asp His
    210                 215                 220

Asp Arg Pro Asp His Asp Gly Arg Asp Ala Asn Asp Asp Thr Ala
225                 230                 235                 240

Pro Arg Pro Gly Gly Ala Ala Gln Asp Phe Ala Ala Gly Phe Arg Trp
                245                 250                 255

Val Leu Gly Gln Pro Val Ile Arg Thr Thr Met Ala Trp Met Met Ile
            260                 265                 270
```

-continued

```
Thr Asn Leu Val Phe Ser Ser Leu Leu Ile Val Leu Leu Ala Leu Ser
            275                 280                 285

Gly Glu Asp Lys Val Gly Ala Gly Glu Leu Gly Leu Thr Met Ala Cys
        290                 295                 300

Phe Gly Ala Gly Gly Leu Leu Gly Gly Leu Phe Ala Ala Arg Met His
305                 310                 315                 320

Ala Ala Ala Arg Pro Pro Val Ile Leu Leu Gly Phe Thr Trp Thr Ala
                325                 330                 335

Ala Leu Gly Ala Ala Leu Met Ala Val Val Pro Thr Gly Leu Pro Gln
            340                 345                 350

Gly Ala Leu Leu Gly Leu Met Ala Leu Phe Ala Pro Leu Ala Asn Thr
            355                 360                 365

Thr Val Leu Thr Tyr Gln Leu Thr Val Thr Pro Asp Glu Leu Arg Gly
            370                 375                 380

Arg Met Ser Gly Val Ala Gly Phe Cys Ser Gly Ala Gly Val Leu
385                 390                 395                 400

Gly Pro Ala Leu Gly Gly Ala Leu Thr Gly Ala Ala Gly Gly Val
                405                 410                 415

Thr Pro Val Leu Ile Cys Ala Gly Cys Leu Val Leu Val Ala Val Ala
                420                 425                 430

Ala Thr Ala Ser Pro Thr Leu Arg Arg Phe Pro Asp Ile Ala Asp Arg
            435                 440                 445

Gln Pro
    450

<210> SEQ ID NO 31
<211> LENGTH: 408
<212> TYPE: PRT
<213> ORGANISM: Streptomyces hygroscopicus

<400> SEQUENCE: 31

Met Gln Thr Pro His Thr Pro Ser Gln Ala Gln Ser Gln Pro Arg Gln
1               5                   10                  15

Lys Pro Gln Pro Ser Gln Ser Gln Ser Gln Ser Gln Pro Asn Leu
            20                  25                  30

Arg Ser Leu Thr Gly Leu Arg Phe Leu Gly Leu Leu Pro Val Phe Leu
        35                  40                  45

Thr His Ala Ala Phe Glu Gly Val Phe Ser Asp Ala Asp Val Ser Trp
    50                  55                  60

Gly Phe Leu Asp Ala Met Gly Asn Thr Gly Tyr Ala Ala Val Ser Phe
65                  70                  75                  80

Phe Phe Val Leu Ser Gly Phe Val Ile Thr Trp Ser Tyr Arg Ser Arg
                85                  90                  95

Asp Thr Thr Arg Thr Phe Trp Arg Arg Arg Ala Phe Arg Val Phe Pro
            100                 105                 110

Asn His Leu Val Ala Tyr Val Phe Ala Leu Ala Leu Met Leu Ala Ala
        115                 120                 125

Gly Ala Ala Phe Asp Ala Pro Ala Leu Ile Ser Gln Met Phe Leu Val
    130                 135                 140

His Ala Trp Val Pro Asp Pro Leu Phe Ile Asp Thr Gly Asn Thr Val
145                 150                 155                 160

Thr Trp Ser Leu Gly Val Asp Val Val Phe Tyr Gly Leu Phe Pro Val
                165                 170                 175

Leu Leu Val Leu Val Asn Lys Ile Lys Pro Thr Arg Leu Trp Tyr Trp
```

```
                180             185             190
Ala Gly Ala Ala Val Leu Met Val Ile Ala Ile Pro Thr Val Ala Leu
        195                 200                 205

Thr Leu Leu Pro Asp Thr Pro Ala Met Ser Val Gly Asp Val Ser Arg
        210                 215                 220

Ser Gln Tyr Trp Phe Thr Tyr Phe Pro Leu Ser Arg Thr Val Glu
225                 230                 235                 240

Cys Val Leu Gly Met Leu Met Ala Arg Ile Val Leu Ser Gly Lys Trp
                245                 250                 255

Ile Gly Leu Arg Val Leu Pro Ala Ser Ala Leu Val Val Gly Tyr
        260                 265                 270

Val Val Ala Gln Gln Leu Pro Phe Leu Tyr Arg Leu Ser Ala Val Leu
        275                 280                 285

Ile Val Pro Ile Val Leu Leu Thr Ala Ser Val Ala Val Ala Asp Ala
        290                 295                 300

Glu Gly Arg Gly Thr Pro Leu Gly Gly Lys Val Met Val Arg Leu Gly
305                 310                 315                 320

Glu Leu Ser Phe Ala Phe Tyr Leu Val His Gln Ala Leu Leu Ala Tyr
                325                 330                 335

Gly His Ile Leu Ile Ser Pro Lys Asn Ala Gln Gly Glu Val Leu Pro
                340                 345                 350

Arg Thr Trp Asp Thr Pro Gly Gly Ile Ala Val Ile Val Leu Ser Phe
                355                 360                 365

Val Val Ser Leu Gly Leu Ala Trp Leu Leu His Asn Gly Val Glu Lys
        370                 375                 380

Pro Val Met Arg Arg Trp Ser Arg Ser Arg Arg Val Thr Gln Gln
385                 390                 395                 400

Pro Pro Ala Lys Val Pro Ala Thr
                405

<210> SEQ ID NO 32
<211> LENGTH: 456
<212> TYPE: PRT
<213> ORGANISM: Streptomyces hygroscopicus

<400> SEQUENCE: 32

Val Trp Ser Ala Arg Lys Ile Ser Ala Lys Leu Arg Arg Asn Gly Gly
1               5                   10                  15

Val Arg Leu Thr Ala Ala Arg Ser Pro Arg Ala Pro Trp Met Ser Gly
            20                  25                  30

Ala Gly Asp His Ala Arg Ile Ile His Gln Pro Thr Val Val Arg Pro
        35                  40                  45

Pro Leu Arg Arg Thr Glu Pro His Arg Leu Ser Arg Ile Trp Arg Glu
    50                  55                  60

Val Arg Met Gln Thr Arg Gln Ser Asn Pro Asn Leu Arg Ser Leu Thr
65                  70                  75                  80

Gly Leu Arg Phe Val Ala Met Leu Pro Val Phe Leu Thr His Ala Ala
                85                  90                  95

Phe Glu Gly Val Phe Ser Asp Ala Lys Val Ser Trp Gly Phe Leu Asp
            100                 105                 110

Ala Met Gly Ser Thr Gly Tyr Met Ala Val Ser Phe Phe Val Leu
        115                 120                 125

Ser Gly Phe Val Ile Thr Trp Ser Tyr Arg Pro Thr Asp Thr Ala Arg
    130                 135                 140
```

-continued

```
Lys Phe Trp Arg Arg Phe Arg Val Phe Pro Asn His Val Val
145                 150                 155                 160

Thr Tyr Ala Leu Ala Leu Gly Leu Ile Ala Val Gly Leu Ser Val
            165                 170                 175

Gly Val Leu Pro Ser Val Thr Gln Leu Phe Leu Val Gln Ser Trp Val
            180                 185                 190

Pro Asp Pro Ala Phe Thr Asp Thr Gly Asn Ser Val Ser Trp Ser Leu
            195                 200                 205

Ala Val Asp Val Val Phe Tyr Ala Leu Phe Pro Val Leu Leu Thr Leu
            210                 215                 220

Val Asn Lys Ile Lys Pro Asn Arg Leu Trp Tyr Trp Val Gly Gly Ser
225                 230                 235                 240

Val Ile Gly Val Ala Val Val Pro Ala Ile Ala Leu Ala Ala Leu Pro
            245                 250                 255

Ser Thr Pro Glu Met Pro Leu Gly Gly Val Ser Val Ser Gln Tyr Trp
            260                 265                 270

Phe Thr Tyr Phe Phe Pro Leu Phe Arg Leu Leu Glu Cys Val Leu Gly
            275                 280                 285

Met Leu Met Ala Arg Ile Val Leu Ser Gly Lys Trp Ile Arg Leu Arg
            290                 295                 300

Val Leu Pro Ala Ala Val Leu Val Val Ile Ala Tyr Tyr Phe Ala Gln
305                 310                 315                 320

Gln Val Pro Tyr Leu Tyr Arg Leu Ser Ala Val Thr Val Leu Pro Val
            325                 330                 335

Ala Leu Leu Thr Ala Ala Ala Val Ala Asp Ser Glu Gly Arg Gly
            340                 345                 350

Thr Leu Phe Gly Ser Lys Val Met Val Trp Phe Gly Glu Leu Ser Phe
            355                 360                 365

Ala Phe Tyr Leu Leu His Asn Leu Val Leu Lys Tyr Gly His Leu Leu
            370                 375                 380

Leu Gly His Thr Glu Glu Gly Glu Leu Val Gly His Thr Trp Gly
385                 390                 395                 400

Val Pro Glu Gly Ile Ala Leu Ile Ala Ala Phe Ala Val Ser Leu
            405                 410                 415

Leu Leu Ala Trp Leu Leu His Asn Gly Val Glu Lys Gln Ala Met Arg
            420                 425                 430

Arg Trp Ser Arg Arg Lys Pro Ala Pro Val Ala Glu Val Thr Ser Gly
            435                 440                 445

Phe Tyr Ala Lys Asp Gly Ala Ile
450                 455

<210> SEQ ID NO 33
<211> LENGTH: 341
<212> TYPE: PRT
<213> ORGANISM: Streptomyces hygroscopicus

<400> SEQUENCE: 33

Val Leu Thr Leu His Leu Gln Asp Asp Val Ala Ala Ile Asp Ala
1               5                   10                  15

Val Ala Asp Glu Leu Ser Arg Arg Tyr Asp Ser Val Glu Ser Thr Glu
            20                  25                  30

Phe Gln Ala Glu Ser Arg Leu Tyr Ala Asp Glu Leu Pro Arg Arg Val
            35                  40                  45

Arg Arg Ala Leu His Glu Tyr Arg Ser Thr Glu Lys Ser Gly Ile Leu
        50                  55                  60
```

Val Val Thr Gly Leu Pro Val Asp Asp Ser Ala Leu Gly Ala Thr Pro
65                  70                  75                  80

Ala Asp Arg Arg His Lys Pro Val Pro Ser Thr Ser Leu Arg Gln Asp
            85                  90                  95

Ile Ala Phe Tyr Leu Ile Ala Asn Leu Leu Gly Asp Pro Ile Gly Trp
            100                 105                 110

Ala Thr Gln Gln Asp Gly Phe Ile Met His Asp Val Tyr Pro Val Gln
            115                 120                 125

Gly Phe Glu His Glu Gln Ile Gly Trp Gly Ser Glu Glu Thr Leu Thr
130                 135                 140

Trp His Thr Glu Asp Ala Phe His Pro Leu Arg Thr Asp Tyr Leu Gly
145                 150                 155                 160

Leu Met Cys Leu Arg Asn Pro Asp Gly Val Glu Thr Thr Ala Cys Asp
                165                 170                 175

Ile Ala Asp Val Glu Ile Asp Asp Glu Thr Arg Glu Thr Leu Ser Gln
            180                 185                 190

Glu Arg Phe Arg Ile Leu Pro Asp Asp Ala His Arg Ile His Gly Lys
            195                 200                 205

Ala Pro Gly Asp Glu Ser Ala Arg Glu Ser Ala Leu Arg Glu Arg Ser
210                 215                 220

Arg Gln Arg Val Ala Ser Ala Leu Glu Ser Pro Asp Pro Val Ala Val
225                 230                 235                 240

Leu Phe Gly Asp Arg Asp Asp Pro Tyr Leu Arg Ile Asp Pro His Tyr
            245                 250                 255

Met Gln Gly Val Gln Gly Glu Thr Glu Gln Arg Ala Leu Glu Thr Ile
            260                 265                 270

Gly Ala Ala Ile Asp Asp Ala Met Ser Gly Val Val Leu Ser Pro Gly
            275                 280                 285

Asp Ile Val Phe Ile Asp Asn Tyr Arg Val Val His Gly Arg Lys Pro
290                 295                 300

Phe Arg Ala Arg Phe Asp Gly Thr Asp Arg Trp Leu Arg Arg Leu Asn
305                 310                 315                 320

Ile Ala Arg Asp Leu Arg Lys Ser Arg Glu Ala Arg Leu Ala Ala Thr
            325                 330                 335

Thr Arg Val Ile Tyr
            340

<210> SEQ ID NO 34
<211> LENGTH: 882
<212> TYPE: DNA
<213> ORGANISM: Streptomyces hygroscopicus

<400> SEQUENCE: 34
gtgctgagct gctactcctc ctcggtcgcg atggagatcc tctcccgctc gctgtccgag    60
acgatcgagt cggtggccct ggtccacccg accttcgaca catcgccga cctgctgcgc   120 ggcaacggcc tgaagctggt gccgctggcg gaggacccgc tgcacggcga cgacctcgac   180
gtgagcctgc tgaagtcggt gggctgtgtc ttcctcacca cgcccaacaa ccccaccggc   240
aaggtcgtct cccgggagcg gctgacccgg ctggccgagc agtgcgccga gcacggcgtc   300
atcctcgcgc tggacacgtc cttccgcggc ttcgacaccc gcgcccacta cgaccactac   360
gaggtgctca acgccagtgg tgtgcgctgg tggtgatcg aggacaccgg caagctgtgg   420
ccgaccctcg acctcaaggt cggcatgctc gtccactccg agaacctcgc gctgccggtc   480

```
gagaagatct actccgacat cctgctcggt gtctccccgc tgatcctcgc gatggtccgc    540
cgcttctccg aggacgccgc ggccggcggt ctggaggatc tgcaccgctt catcgccgcc    600
aaccgtgcca tggtgcgcgc ggaactcgcc ggtctgccgg gcgtcacggt ccccgacccc    660
gacagccggg ccagcgtcga gcgggtcgcc atcgatgacc tgacgggcac gcaggtctgg    720
gcgaagctgc gggagcacaa cgtctacgcg ctcccgtgcc gccgttcca ctgggccaac     780 ccgtccgagg gtgaccacac cctgcggctc gcgctggccc tgccacgga cccgctcgcc     840 cagtccgtgc gcgccctgcg ccacgtgctg aaacagcgtt ga                       882
```

<210> SEQ ID NO 35
<211> LENGTH: 293
<212> TYPE: PRT
<213> ORGANISM: Streptomyces hygroscopicus

<400> SEQUENCE: 35

```
Val Leu Ser Cys Tyr Ser Ser Val Ala Met Glu Ile Leu Ser Arg
1               5                   10                  15

Ser Leu Ser Glu Thr Ile Glu Ser Val Ala Leu Val His Pro Thr Phe
            20                  25                  30

Asp Asn Ile Ala Asp Leu Leu Arg Gly Asn Gly Leu Lys Leu Val Pro
        35                  40                  45

Leu Ala Glu Asp Pro Leu His Gly Asp Asp Leu Asp Val Ser Leu Leu
    50                  55                  60

Lys Ser Val Gly Cys Val Phe Leu Thr Thr Pro Asn Asn Pro Thr Gly
65                  70                  75                  80

Lys Val Val Ser Arg Glu Arg Leu Thr Arg Leu Ala Glu Gln Cys Ala
                85                  90                  95

Glu His Gly Val Ile Leu Ala Leu Asp Thr Ser Phe Arg Gly Phe Asp
            100                 105                 110

Thr Arg Ala His Tyr Asp His Tyr Glu Val Leu Asn Ala Ser Gly Val
        115                 120                 125

Arg Trp Val Val Ile Glu Asp Thr Gly Lys Leu Trp Pro Thr Leu Asp
    130                 135                 140

Leu Lys Val Gly Met Leu Val His Ser Glu Asn Leu Ala Leu Pro Val
145                 150                 155                 160

Glu Lys Ile Tyr Ser Asp Ile Leu Leu Gly Val Ser Pro Leu Ile Leu
                165                 170                 175

Ala Met Val Arg Arg Phe Ser Glu Asp Ala Ala Ala Gly Gly Leu Glu
            180                 185                 190

Asp Leu His Arg Phe Ile Ala Ala Asn Arg Ala Met Val Arg Ala Glu
        195                 200                 205

Leu Ala Gly Leu Pro Gly Val Thr Val Pro Asp Pro Asp Ser Arg Ala
    210                 215                 220

Ser Val Glu Arg Val Ala Ile Asp Asp Leu Thr Gly Thr Gln Val Trp
225                 230                 235                 240

Ala Lys Leu Arg Glu His Asn Val Tyr Ala Leu Pro Cys Arg Pro Phe
                245                 250                 255

His Trp Ala Asn Pro Ser Glu Gly Asp His Thr Leu Arg Leu Ala Leu
            260                 265                 270

Ala Arg Ser Thr Asp Pro Leu Ala Gln Ser Val Arg Ala Leu Arg His
        275                 280                 285

Val Leu Lys Gln Arg
    290
```

<210> SEQ ID NO 36
<211> LENGTH: 1248
<212> TYPE: DNA
<213> ORGANISM: Streptomyces hygroscopicus

<400> SEQUENCE: 36

```
atgacgcctg tcgcagaagg aggactcccg cacggctccg tgccctcgct gtcgcacacg      60
cggcagtggc ggcccggggt cgtgcaggag gtcgccccgg ccggcgtcct cgacctgggc     120
cccggctaca tcgagccggc actcctgccc gtacgcctgc tgcggggcgc gtacgagcaa     180
gcgctggcga gtacggcgc cgcggcgctg ggctacggtc acgacccggg cgcgcagccg     240
ctgcgcgacc ggctggccgc ccgcgccgcc gcggcggacg gcctcccctg cgacccggac     300
caggtgctgc tgacctccgg cacgtcccag gccctctatc tgctggcgac ctcgctcgcg     360
gccccgggcg acacagtgct gacggaggag ctctgttacg acctgggaca gcggatattc     420
cgggactgct cactgcggct ccgccaggtc gccatggacg gtcggggat gctgcccgac     480
gcgctggacc gcgccctgac cgagggcgcg cgagcgggcg cgaaaaccgc tttcgtctac     540
ctcaccccca cccaccacaa ccccacgggc cacacgatgc cgctggcgcg ccgccgcctg     600
ctgctcgaag tggccgcccg gcacgatgtg ctgatcgtgg aggacgacgc ctacacggaa     660
ctgtccctga tccctgaccg cactcccccg ccctcgctgg ccgccctggc cggctaccgg     720
cgggtggtgc ggctgtgcag cttctccaag accctcggcc ccggactgcg gctgggctgg     780
ctgctcgccg accgggaact ggccggccgg ctggccacgc acggcctgtt cgtcagcggg     840
ggttcgctca accacaccac ctcgctcgcc gtgagcaccc tgctcgcgag cggcgcgtac     900
gaccgtcatc tcgacgcgtt ccgggcgcag ttgcgtgctc gtaggacgc gctcgtgggc     960
gctctacgcg cgatgctgga cgacggggtg gagctgcgca ccccggaggg cggattcttc    1020
ctgtggctgc gggccgggga cggggccgac gagcgtgagc tgctcgacgg cgccgcccgg    1080
gcgggcgtca ggatcgccgc cggatcgcgc ttcggcacaa cccaggggc cggcttgcgc     1140
ctggccttca gcttcaaccc gcccgcgtta ctggagcagg ccgccaagcg gctgaccacc    1200
gcatggtccg gcagcacgcc ggacctcgag atcggagtga gatcgtga              1248
```

<210> SEQ ID NO 37
<211> LENGTH: 400
<212> TYPE: PRT
<213> ORGANISM: Streptomyces hygroscopicus

<400> SEQUENCE: 37

```
Met Thr Pro Val Ala Glu Gly Gly Leu Pro His Gly Ser Val Pro Ser
1               5                   10                  15

Leu Ser His Thr Arg Gln Trp Arg Pro Gly Val Val Gln Glu Val Ala
                20                  25                  30

Pro Ala Gly Val Leu Asp Leu Gly Pro Gly Tyr Ile Glu Pro Ala Leu
            35                  40                  45

Leu Pro Val Arg Leu Leu Arg Gly Ala Tyr Glu Gln Ala Leu Ala Glu
        50                  55                  60

Tyr Gly Ala Ala Ala Leu Gly Tyr Gly His Asp Pro Gly Ala Gln Pro
65                  70                  75                  80

Leu Arg Asp Arg Leu Ala Ala Arg Ala Ala Ala Asp Gly Leu Pro
                85                  90                  95

Cys Asp Pro Asp Gln Val Leu Leu Thr Ser Gly Thr Ser Gln Ala Leu
            100                 105                 110
```

Tyr Leu Leu Ala Thr Ser Leu Ala Ala Pro Gly Asp Thr Val Leu Thr
            115                 120                 125

Glu Glu Leu Cys Tyr Asp Leu Gly Gln Arg Ile Phe Arg Asp Cys Ser
            130                 135                 140

Leu Arg Leu Arg Gln Val Ala Met Asp Gly Ser Gly Met Leu Pro Asp
145                 150                 155                 160

Ala Leu Asp Arg Ala Leu Thr Glu Gly Ala Arg Ala Gly Ala Lys Thr
                165                 170                 175

Ala Phe Val Tyr Leu Thr Pro Thr His His Asn Pro Thr Gly His Thr
            180                 185                 190

Met Pro Leu Ala Arg Arg Arg Leu Leu Glu Val Ala Ala Arg His
        195                 200                 205

Asp Val Leu Ile Val Glu Asp Asp Ala Tyr Thr Glu Leu Ser Leu Ile
            210                 215                 220

Pro Asp Arg Thr Pro Pro Ser Leu Ala Ala Leu Ala Gly Tyr Arg
225                 230                 235                 240

Arg Val Val Arg Leu Cys Ser Phe Ser Lys Thr Leu Gly Pro Gly Leu
                245                 250                 255

Arg Leu Gly Trp Leu Leu Ala Asp Arg Glu Leu Ala Gly Arg Leu Ala
            260                 265                 270

Thr His Gly Leu Phe Val Ser Gly Gly Ser Leu Asn His Thr Thr Ser
        275                 280                 285

Leu Ala Val Ser Thr Leu Leu Ala Ser Gly Ala Tyr Asp Arg His Leu
            290                 295                 300

Asp Ala Phe Arg Ala Gln Leu Arg Ala Arg Arg Asp Ala Leu Val Gly
305                 310                 315                 320

Ala Leu Arg Ala Met Leu Asp Asp Gly Val Glu Leu Arg Thr Pro Glu
                325                 330                 335

Gly Gly Phe Phe Leu Trp Leu Arg Ala Gly Asp Gly Ala Asp Glu Arg
            340                 345                 350

Glu Leu Leu Asp Gly Ala Ala Arg Ala Gly Val Arg Ile Ala Ala Gly
        355                 360                 365

Ser Arg Phe Gly Thr Thr Gln Gly Ala Gly Leu Arg Leu Ala Phe Ser
            370                 375                 380

Phe Asn Pro Pro Ala Leu Leu Glu Gln Ala Ala Lys Arg Leu Thr Thr
385                 390                 395                 400

<210> SEQ ID NO 38
<211> LENGTH: 909
<212> TYPE: DNA
<213> ORGANISM: Streptomyces hygroscopicus

<400> SEQUENCE: 38
atggtccggc agcacgccgg acctcgagat cggagtgaga tcgtgacgac cagcaccggg      60
accaacggcc ggcacacggt ggccggtcca ggcagcgccg gtcccgtcgg gtacagcctg     120
ccgctctcgc cgacgggcga gtcggcgatg ctcacaccac cgccgtggca cttctccggc     180
gaggtcgtca tggtcgacta ccgcgtcgac ccggacgcgg cccgacggtt cctgccgccg     240
ggcctggagc cgggtgccga cccgggcgcc gcggcggcgg tgttcgcgac ctggcagtgg     300
tgttcgcagg acgagcgga gctgaccgac cccggtcgct gccagttcgg ggagttcctg     360
atcctgctca gctgcgagtt cgaggggcgt cccatggcgc gctgcccgta cgcctgggtg     420
gaccaggccg tgcccatgat gcgcggctgg gtgcagggga tgcccaagca gttcggcgtg     480
attcaccaga gccggcccgt cacggtcggc aaggcgggct cccggctggc gcccggcggt     540

```
cgtttcgacg gcgcgctgtc cgtgcacgga cgacgcgtcg tggaggcctc ggtcaccgtg      600
gacaggtcga cggaccagcc gccggcgctg cacgatgttc ccctggcgca cacctggtg       660 ttcccggagt gggtgccctc cggcggcggg ccgcgaccac ggctggtcgc ctccgaggta      720
agcgatgtgg aattctcccc gatctggacc ggatcgggtg atctcacgtt ctttgacgga      780 ctggggatg atttcggggc gctcgcaccg ttggaagtag gtagcggcca cgtgttctcg       840
tacggggaga ccttgcacgg cggccggctg ctcagcgact actcggtatc agaacgacat      900
cagccatga                                                              909
```

<210> SEQ ID NO 39
<211> LENGTH: 302
<212> TYPE: PRT
<213> ORGANISM: Streptomyces hygroscopicus

<400> SEQUENCE: 39

```
Met Val Arg Gln His Ala Gly Pro Arg Asp Arg Ser Glu Ile Val Thr
1               5                   10                  15

Thr Ser Thr Gly Thr Asn Gly Arg His Thr Val Ala Gly Pro Gly Ser
            20                  25                  30

Ala Gly Pro Val Gly Tyr Ser Leu Pro Leu Ser Pro Thr Gly Glu Ser
        35                  40                  45

Ala Met Leu Thr Pro Pro Trp His Phe Ser Gly Glu Val Val Met
    50                  55                  60

Val Asp Tyr Arg Val Asp Pro Asp Ala Ala Arg Arg Phe Leu Pro Pro
65                  70                  75                  80

Gly Leu Glu Pro Gly Ala Asp Pro Gly Ala Ala Ala Val Phe Ala
            85                  90                  95

Thr Trp Gln Trp Cys Ser Gln Asp Gly Ala Glu Leu Thr Asp Pro Gly
        100                 105                 110

Arg Cys Gln Phe Gly Glu Phe Leu Ile Leu Leu Ser Cys Glu Phe Glu
    115                 120                 125

Gly Arg Pro Met Ala Arg Cys Pro Tyr Ala Trp Val Asp Gln Ala Val
130                 135                 140

Pro Met Met Arg Gly Trp Val Gln Gly Met Pro Lys Gln Phe Gly Val
145                 150                 155                 160

Ile His Gln Ser Arg Pro Val Thr Val Gly Lys Ala Gly Ser Arg Leu
                165                 170                 175

Ala Pro Gly Gly Arg Phe Asp Gly Ala Leu Ser Val His Gly Arg Arg
            180                 185                 190

Val Val Glu Ala Ser Val Thr Val Asp Arg Ser Thr Asp Gln Pro Pro
        195                 200                 205

Ala Leu His Asp Val Pro Leu Ala His Thr Leu Val Phe Pro Glu Trp
    210                 215                 220

Val Pro Ser Gly Gly Pro Arg Pro Arg Leu Val Ala Ser Glu Val
225                 230                 235                 240

Ser Asp Val Glu Phe Ser Pro Ile Trp Thr Gly Ser Gly Asp Leu Thr
                245                 250                 255

Phe Phe Asp Gly Leu Gly Asp Asp Phe Gly Ala Leu Ala Pro Leu Glu
            260                 265                 270

Val Gly Ser Gly His Val Phe Ser Tyr Gly Glu Thr Leu His Gly Gly
        275                 280                 285

Arg Leu Leu Ser Asp Tyr Ser Val Ser Glu Arg His Gln Pro
    290                 295                 300
```

<210> SEQ ID NO 40
<211> LENGTH: 216
<212> TYPE: DNA
<213> ORGANISM: Streptomyces hygroscopicus

<400> SEQUENCE: 40

```
gtgggcacaa accccttcga cgaccccgac ggccggtatc tggtgctggt caacgaggaa    60
gaccagcatt cactctggcc ggctttcgcc gaggtgcccc agggctggac ggtggcgctc   120
gcggaaaccg accgtcagtc cgcgctcgac ttcatcaccg agcactggac cgacatgcgg   180
ccgcgcagcc tggtgcgggc gatggaagag gcttag                             216
```

<210> SEQ ID NO 41
<211> LENGTH: 71
<212> TYPE: PRT
<213> ORGANISM: Streptomyces hygroscopicus

<400> SEQUENCE: 41

```
Val Gly Thr Asn Pro Phe Asp Asp Pro Asp Gly Arg Tyr Leu Val Leu
 1               5                  10                  15

Val Asn Glu Glu Asp Gln His Ser Leu Trp Pro Ala Phe Ala Glu Val
            20                  25                  30

Pro Gln Gly Trp Thr Val Ala Leu Ala Glu Thr Asp Arg Gln Ser Ala
        35                  40                  45

Leu Asp Phe Ile Thr Glu His Trp Thr Asp Met Arg Pro Arg Ser Leu
    50                  55                  60

Val Arg Ala Met Glu Glu Ala
65                  70
```

<210> SEQ ID NO 42
<211> LENGTH: 1266
<212> TYPE: DNA
<213> ORGANISM: Streptomyces hygroscopicus

<400> SEQUENCE: 42

```
gtgaccctga ccgcggcgct gaccggggcg ttcgccccg cccgcccgtc cctcaggagc    60
gagaaggccg cccccgccgc cccccactcc ccccagtgga cagccacctg gggagccgcc   120
atgcagcagg cgacgaacga ggccacggag gacaccccga ctggtcccg gcagggattc   180
aagaacgaga ccctgcgcca ggtgatccgg ctcagcgtcg gcggccccga gctccgtatc   240
cgcctctcca acgcctacgg caccaagccc ctccacatcg ccggcgccac cgtcgccagg   300
tccgacggcg aggccaaggc gcgccccggc accgtacgca ccctcacctt ccgccatgcg   360
cccgccctca ccatccccgc gggccgcgac accgtcagcg acgcggtggc catgccgacc   420
gccaacctcg aaaaactcac cgtcaccctg cgcttcaccg cccccaccgg cccggccacc   480
atgcaccgct tcaccacggc cacgtcctac cgcgccccg gcgaccggct acgcagcccc   540
gccgccgatg acttcaaccg ccgtgcctcg cacgcctggt actacctgac ggccgtcgat   600
gtgacccagg agccgccccg ttcggccgac tccctcatgg tcttcggcga ctccctcatg   660
gacggcgtcg gcaccagccc cgacaccgac aaccgcttct ccgacaaact cgccgaacgc   720
ctcatcgccg ccgccgcccc caggggaatg accaacgccg gctggcgggt gaccccctg    780
ctgcacgatt cccccctgct tcggcgagaag ggcaccgccc gcttcgccaa ggaactgcgc   840
gatcgcgccg ccctgcgcac cgtcttcatc cacctcggcg ccaatgacct cgcccagtcc   900
cagcaggacg accctgcac aggaaccgc cccccggtga ccgcccaaca gctcatcgac   960
```

-continued

```
ggccaccgcg ccctggtccg cgcggcccac gcccgcggta tcaaggccat cggtgtgacg      1020
atcctccccc tcaggagcgc cgtcttcccc ttcaccaccc ccgccggtga caagatccgc      1080
cggcagctca accactggat ccgcaccagc cacacctacg acgccgtcct cgacgccgac      1140
cgcgtcctga ccgaccccgc gaaccccaac cgccccgcc  ccggctacat ctcccaggac      1200
ggcctccacc ccagcgacgc cggctacctg gccctcgcct ccgccgtcga cctgaacgcc      1260
ctctga                                                                 1266
```

<210> SEQ ID NO 43
<211> LENGTH: 421
<212> TYPE: PRT
<213> ORGANISM: Streptomyces hygroscopicus

<400> SEQUENCE: 43

```
Val Thr Leu Thr Ala Ala Leu Thr Gly Ala Phe Ala Pro Ala Arg Pro
1               5                   10                  15

Ser Leu Arg Ser Glu Lys Ala Ala Pro Ala Ala Pro His Ser Pro Gln
            20                  25                  30

Trp Thr Ala Thr Trp Gly Ala Ala Met Gln Gln Ala Thr Asn Glu Ala
        35                  40                  45

Thr Glu Asp Thr Pro Asn Trp Ser Arg Gln Gly Phe Lys Asn Glu Thr
    50                  55                  60

Leu Arg Gln Val Ile Arg Leu Ser Val Gly Gly Pro Glu Leu Arg Ile
65                  70                  75                  80

Arg Leu Ser Asn Ala Tyr Gly Thr Lys Pro Leu His Ile Ala Gly Ala
                85                  90                  95

Thr Val Ala Arg Ser Asp Gly Glu Ala Lys Ala Arg Pro Gly Thr Val
            100                 105                 110

Arg Thr Leu Thr Phe Arg His Ala Pro Ala Leu Thr Ile Pro Ala Gly
        115                 120                 125

Arg Asp Thr Val Ser Asp Ala Val Ala Met Pro Thr Ala Asn Leu Glu
    130                 135                 140

Lys Leu Thr Val Thr Leu Arg Phe Thr Ala Pro Thr Gly Pro Ala Thr
145                 150                 155                 160

Met His Arg Phe Thr Thr Ala Thr Ser Tyr Arg Ala Pro Gly Asp Arg
                165                 170                 175

Leu Arg Ser Pro Ala Ala Asp Asp Phe Asn Arg Arg Ala Ser His Ala
            180                 185                 190

Trp Tyr Tyr Leu Thr Ala Val Asp Val Thr Gln Glu Pro Pro Arg Ser
        195                 200                 205

Ala Asp Ser Leu Met Val Phe Gly Asp Ser Leu Met Asp Gly Val Gly
    210                 215                 220

Thr Ser Pro Asp Thr Asp Asn Arg Phe Ser Asp Lys Leu Ala Glu Arg
225                 230                 235                 240

Leu Ile Ala Ala Gly Arg Pro Gln Gly Met Thr Asn Ala Gly Leu Ala
                245                 250                 255

Gly Asp Pro Leu Leu His Asp Ser Pro Cys Phe Gly Glu Lys Gly Thr
            260                 265                 270

Ala Arg Phe Ala Lys Glu Leu Arg Asp Arg Ala Ala Leu Arg Thr Val
        275                 280                 285

Phe Ile His Leu Gly Ala Asn Asp Leu Ala Gln Ser Gln Gln Asp Asp
    290                 295                 300

Pro Cys Thr Arg Asn Arg Pro Pro Val Thr Ala Gln Gln Leu Ile Asp
```

```
                305                 310                 315                 320
Gly His Arg Ala Leu Val Arg Ala Ala His Ala Arg Gly Ile Lys Ala
                    325                 330                 335

Ile Gly Val Thr Ile Leu Pro Leu Arg Ser Ala Val Phe Pro Phe Thr
                340                 345                 350

Thr Pro Ala Gly Asp Lys Ile Arg Arg Gln Leu Asn His Trp Ile Arg
            355                 360                 365

Thr Ser His Thr Tyr Asp Ala Val Leu Asp Ala Asp Arg Val Leu Thr
        370                 375                 380

Asp Pro Ala Asn Pro Asn Arg Pro Arg Pro Gly Tyr Ile Ser Gln Asp
385                 390                 395                 400

Gly Leu His Pro Ser Asp Ala Gly Tyr Leu Ala Leu Ala Ser Ala Val
                    405                 410                 415

Asp Leu Asn Ala Leu
                420

<210> SEQ ID NO 44
<211> LENGTH: 1632
<212> TYPE: DNA
<213> ORGANISM: Streptomyces hygroscopicus

<400> SEQUENCE: 44
atgctcaccg tcttgcggt ggccgacttc cgcgaccggg tacgccggcc cgcgtatgtc      60
gtgatcctgg ccgcggccgt cgccctcggt tacgtggcgg tgcccgactc ggacgccaaa    120
tggatgatca tgcagatcgg tgatcaccgc gggatctaca cagcgccta cgtcggcatg     180 gtgacggccc tggccagcgg tctgtggatc accctcggcg gcttctacat cgtccgcaac    240
tccatcgaac gcgaccgcag cacccgcgtc ggccagctgc tcgccgccac cccgctgcgc    300
accaccgcgt acatgctcgg caagttcctc agcaacctca tgctgctgtc ctccatgctc    360
gtggtgctcg cgctcaccgc cctggtcatg caactggccc gcggcgagtc gcacgacatc    420
gacctgatcg ccctctggca gcccttcctc ctcatcgcgc tgccgctggt cgcgctgacc    480
gccgccctcg cgctcctctt cgaatcgctg ccgctgctgc gcaccggcct gggcaacatc    540
ctgtggttct gcatctggat ggtcgtctcg acggccggcc agggccccgg tctgcccctc    600
gacggcatcg gcgtcaacag cgtcgtccgg tcgatgtatg acgacatggt cgcccagcac    660
atcgatgtca ccggcgcgtt cagcctcggt ctgacctacc tcgacaagcc cctcgggctc    720
ttcacctggg acggcttcac gcccaccgcc ggctatgtcc tcggccgggt gacgctgctg    780
ctgatcgccg tcgtgatcgc catgctcccc gcgctgtggt tcggccgctt cgaccccgcg    840
cgaacctggc tgggccaggg cgcaccccc gagcaggccc cggccgacgg tgtcgtccag    900
ccggtcttca tcgacgaggt cggcccgggg acgcctccgc tgtccgttca gggccatggg    960
ggagcttccc cgtcccggcc caccgtcgcc acgctgctgc gcacccgccc ggagccgggc    1020
gccgtgaccc tgcgcgtctg gccggcgag gtccgcatcc tgctgcaagg tgtgcgctgg    1080
tggtggtgga ccggtgccgc attcctcatg atcgccgcgc tcctcctccc ggggatccac    1140
ggcatcatcc gcgtgatgct gccgctgtcc tggatctggc cggtgctgat ctggtcgcgg    1200
ctgggcaccc agcgccacga gtaccacgtc gacggcatgc tcggcgccta ccccgcggtg    1260
cgccgccggg tcttcgccga atgggccgcg ggcctgacca tcaccgccgt ggccggcatc    1320
ggtcccctga tccgcctggt ggccgccgcc gactggttcg gtctggccgg ctgggtcggc    1380
ggggccctgt tcatcccgtc cctggccctc accctgggca cgctcagccg tacccatcgc    1440
```

```
ctcttccagg cggtctacct gccgctctgg tacagcgtcg ccaacggact gccgatcttc    1500
gacttcatgg gcgcgctgcg cgacagcagc gaactggccg ccgtgcagcc gtcggtgacc    1560
gtcgtggttt ccgcggccct gatggccatc gtcttcatga ccggcgtact ccgccgcttc    1620
ggccgcgact ga                                                        1632
```

<210> SEQ ID NO 45
<211> LENGTH: 543
<212> TYPE: PRT
<213> ORGANISM: Streptomyces hygroscopicus

<400> SEQUENCE: 45

```
Met Leu Thr Gly Leu Ala Val Ala Asp Phe Arg Asp Arg Val Arg Arg
1               5                   10                  15

Pro Ala Tyr Val Val Ile Leu Ala Ala Val Ala Leu Gly Tyr Val
            20                  25                  30

Ala Val Pro Asp Ser Asp Ala Lys Trp Met Ile Met Gln Ile Gly Asp
        35                  40                  45

His Arg Gly Ile Tyr Asn Ser Ala Tyr Val Gly Met Val Thr Ala Leu
    50                  55                  60

Ala Ser Gly Leu Trp Ile Thr Leu Gly Gly Phe Tyr Ile Val Arg Asn
65                  70                  75                  80

Ser Ile Glu Arg Asp Arg Ser Thr Arg Val Gly Gln Leu Leu Ala Ala
                85                  90                  95

Thr Pro Leu Arg Thr Thr Ala Tyr Met Leu Gly Lys Phe Leu Ser Asn
            100                 105                 110

Leu Met Leu Leu Ser Ser Met Leu Val Val Leu Ala Leu Thr Ala Leu
        115                 120                 125

Val Met Gln Leu Ala Arg Gly Glu Ser His Asp Ile Asp Leu Ile Ala
    130                 135                 140

Leu Trp Gln Pro Phe Leu Leu Ile Ala Leu Pro Leu Val Ala Leu Thr
145                 150                 155                 160

Ala Ala Leu Ala Leu Leu Phe Glu Ser Leu Pro Leu Leu Arg Thr Gly
                165                 170                 175

Leu Gly Asn Ile Leu Trp Phe Cys Ile Trp Met Val Val Ser Thr Ala
            180                 185                 190

Gly Gln Gly Pro Gly Leu Pro Leu Asp Gly Ile Gly Val Asn Ser Val
        195                 200                 205

Val Arg Ser Met Tyr Asp Asp Met Val Ala Gln His Ile Asp Val Thr
    210                 215                 220

Gly Ala Phe Ser Leu Gly Leu Thr Tyr Leu Asp Lys Pro Leu Gly Leu
225                 230                 235                 240

Phe Thr Trp Asp Gly Phe Thr Pro Thr Ala Gly Tyr Val Leu Gly Arg
                245                 250                 255

Val Thr Leu Leu Leu Ile Ala Val Val Ile Ala Met Leu Pro Ala Leu
            260                 265                 270

Trp Phe Gly Arg Phe Asp Pro Ala Arg Thr Trp Leu Gly Gln Gly Arg
        275                 280                 285

Thr Pro Glu Gln Ala Pro Ala Asp Gly Val Val Gln Pro Val Phe Ile
    290                 295                 300

Asp Glu Val Gly Pro Gly Thr Pro Pro Leu Ser Val Gln Gly His Gly
305                 310                 315                 320

Gly Ala Ser Pro Ser Arg Pro Thr Val Ala Thr Leu Leu Arg Thr Arg
                325                 330                 335
```

```
Pro Glu Pro Gly Ala Val Thr Leu Arg Val Trp Ala Gly Glu Val Arg
            340                 345                 350

Ile Leu Leu Gln Gly Val Arg Trp Trp Trp Thr Gly Ala Ala Phe
        355                 360                 365

Leu Met Ile Ala Ala Leu Ser Ser Pro Gly Ile His Gly Ile Ile Arg
        370                 375                 380

Val Met Leu Pro Leu Ser Trp Ile Trp Pro Val Leu Ile Trp Ser Arg
385                 390                 395                 400

Leu Gly Thr Gln Arg His Glu Tyr His Val Asp Gly Met Leu Gly Ala
                405                 410                 415

Tyr Pro Ala Val Arg Arg Val Phe Ala Glu Trp Ala Ala Gly Leu
                420                 425                 430

Thr Ile Thr Ala Val Ala Gly Ile Gly Pro Leu Ile Arg Leu Val Ala
        435                 440                 445

Ala Ala Asp Trp Phe Gly Leu Ala Gly Trp Val Gly Gly Ala Leu Phe
        450                 455                 460

Ile Pro Ser Leu Ala Leu Thr Leu Gly Thr Leu Ser Arg Thr His Arg
465                 470                 475                 480

Leu Phe Gln Ala Val Tyr Leu Pro Leu Trp Tyr Ser Val Ala Asn Gly
                485                 490                 495

Leu Pro Ile Phe Asp Phe Met Gly Ala Leu Arg Asp Ser Ser Glu Leu
            500                 505                 510

Ala Ala Val Gln Pro Ser Val Thr Val Val Ser Ala Ala Leu Met
            515                 520                 525

Ala Ile Val Phe Met Thr Gly Val Leu Arg Arg Phe Gly Arg Asp
        530                 535                 540

<210> SEQ ID NO 46
<211> LENGTH: 921
<212> TYPE: DNA
<213> ORGANISM: Streptomyces hygroscopicus

<400> SEQUENCE: 46
gtgctcgacc tcgtcaacat caccaaggtc tacaagggcg gcaagcacgc cgtggacgac      60
ctgacgatgc gtctggaacc cggcatgctc ggcctgctgg ccccaacgg cgccggcaag     120 tcgtccctca tgcggatcgc ctccacggtc acccggccca ccagcggaaa ggtcctcttc     180
cacggagagg acgcggtcgc caagcccaac gcgctgcgcc gggccctcgg ttacctcccg     240
caggacttcg gcgtctaccc gaacctgacc tcccgcgagt tcctcaggta tctggcggcg     300
gccaagggcg tctcggccaa gaccgccaag gcccgtatcg atgagctcct ggagctcgtc     360
aacctcaccg aagcggtcaa gcgtcccctg ggcaagtact ccggcggcat gctgcgccgg     420
gtcggcatcg cccaggtgct gctcgccgac cgcaggtga tcatcgtgga cgagccgacc     480
gcggggctgg accccgagga gcgggtcagg ttccgcaatc tgctcagcga tctgcggcc     540 gacaaggtcg tgatgctctc cacccacatc gtctccgacg tcgagtcggt ggcctccgac     600
atcgcggtga tggccggcgg ccggctgcag cgccgcggca ccccgagga cctgctgcgc     660 tcggtggacg gccaggtgtg ggaggtgctg gtcgacccct cgtccgtagc ggcggtgcag     720
gcgcagtaca ccgtcagccg cctggtccgc acgaccgagg cgtccgtat ccggctgctc     780 tcgcgcgagc tgccgtacga gggcgccgtc cagctgacgc ccgacctgga agacgcctac     840
ctcgccatca tccgtggggt cgacggcggc cgggccgccc agggcttcgg cgaacggccg     900
ctccaggcac gggtggtgtg a                                               921
```

```
<210> SEQ ID NO 47
<211> LENGTH: 306
<212> TYPE: PRT
<213> ORGANISM: Streptomyces hygroscopicus

<400> SEQUENCE: 47
```

| | | | | | | | | | | | | | | | |
|---|---|---|---|---|---|---|---|---|---|---|---|---|---|---|---|
| Val | Leu | Asp | Leu | Val | Asn | Ile | Thr | Lys | Val | Tyr | Lys | Gly | Gly | Lys | His |
| 1 | | | | 5 | | | | | 10 | | | | | 15 | |
| Ala | Val | Asp | Asp | Leu | Thr | Met | Arg | Leu | Glu | Pro | Gly | Met | Leu | Gly | Leu |
| | | | 20 | | | | | 25 | | | | | 30 | | |
| Leu | Gly | Pro | Asn | Gly | Ala | Gly | Lys | Ser | Ser | Leu | Met | Arg | Ile | Ala | Ser |
| | | | | 35 | | | | | 40 | | | | | 45 | |
| Thr | Val | Thr | Arg | Pro | Thr | Ser | Gly | Lys | Val | Leu | Phe | His | Gly | Glu | Asp |
| | | 50 | | | | | 55 | | | | | 60 | | | |
| Ala | Val | Ala | Lys | Pro | Asn | Ala | Leu | Arg | Arg | Ala | Leu | Gly | Tyr | Leu | Pro |
| 65 | | | | | 70 | | | | | 75 | | | | | 80 |
| Gln | Asp | Phe | Gly | Val | Tyr | Pro | Asn | Leu | Thr | Ser | Arg | Glu | Phe | Leu | Arg |
| | | | | 85 | | | | | 90 | | | | | 95 | |
| Tyr | Leu | Ala | Ala | Ala | Lys | Gly | Val | Ser | Ala | Lys | Thr | Ala | Lys | Ala | Arg |
| | | | | 100 | | | | | 105 | | | | | 110 | |
| Ile | Asp | Glu | Leu | Leu | Glu | Leu | Val | Asn | Leu | Thr | Glu | Ala | Val | Lys | Arg |
| | | | 115 | | | | | 120 | | | | | 125 | | |
| Pro | Leu | Gly | Lys | Tyr | Ser | Gly | Gly | Met | Leu | Arg | Arg | Val | Gly | Ile | Ala |
| | | 130 | | | | | 135 | | | | | 140 | | | |
| Gln | Val | Leu | Leu | Ala | Asp | Pro | Gln | Val | Ile | Ile | Val | Asp | Glu | Pro | Thr |
| 145 | | | | | 150 | | | | | 155 | | | | | 160 |
| Ala | Gly | Leu | Asp | Pro | Glu | Glu | Arg | Val | Arg | Phe | Arg | Asn | Leu | Leu | Ser |
| | | | | 165 | | | | | 170 | | | | | 175 | |
| Asp | Leu | Ala | Ala | Asp | Lys | Val | Val | Met | Leu | Ser | Thr | His | Ile | Val | Ser |
| | | | | 180 | | | | | 185 | | | | | 190 | |
| Asp | Val | Glu | Ser | Val | Ala | Ser | Asp | Ile | Ala | Val | Met | Ala | Gly | Gly | Arg |
| | | | 195 | | | | | 200 | | | | | 205 | | |
| Leu | Gln | Arg | Arg | Gly | Thr | Pro | Glu | Asp | Leu | Leu | Arg | Ser | Val | Asp | Gly |
| | | 210 | | | | | 215 | | | | | 220 | | | |
| Gln | Val | Trp | Glu | Val | Leu | Val | Asp | Pro | Ser | Ser | Val | Ala | Ala | Val | Gln |
| 225 | | | | | 230 | | | | | 235 | | | | | 240 |
| Ala | Gln | Tyr | Thr | Val | Ser | Arg | Leu | Val | Arg | Thr | Thr | Glu | Gly | Val | Arg |
| | | | | 245 | | | | | 250 | | | | | 255 | |
| Ile | Arg | Leu | Leu | Ser | Arg | Glu | Leu | Pro | Tyr | Glu | Gly | Ala | Val | Gln | Leu |
| | | | | 260 | | | | | 265 | | | | | 270 | |
| Thr | Pro | Asp | Leu | Glu | Asp | Ala | Tyr | Leu | Ala | Ile | Ile | Arg | Gly | Val | Asp |
| | | | 275 | | | | | 280 | | | | | 285 | | |
| Gly | Gly | Arg | Ala | Ala | Gln | Gly | Phe | Gly | Glu | Arg | Pro | Leu | Gln | Ala | Arg |
| | | 290 | | | | | 295 | | | | | 300 | | | |
| Val | Val | | | | | | | | | | | | | | |
| 305 | | | | | | | | | | | | | | | |

```
<210> SEQ ID NO 48
<211> LENGTH: 429
<212> TYPE: DNA
<213> ORGANISM: Streptomyces hygroscopicus

<400> SEQUENCE: 48
gtgcaccacc ccgtgactct ggaggaaccg atgttctcag gcaccatctc gaagcggccc      60
gccacactcg tcgtcgcggt ggcggccgtc gccgccaccc tcggcctctc cggctgctcc     120
```

```
gtggacgcct cgaaggcgaa gcccgaatcg aagtcgttca cgtactcggg caagtccctg      180
aaggtgacga cgcacgaggt cgccaccaag gtggtcgccg ccgaccgcaa ggacatcaag      240
gtcacccgct ggttcgactc ggccgcgggc accgagcacc tgaagtggac cctcaagggc      300
gacaccctgg acatcgacgc cggctgcagc ggtatcgcga tctgcgacgc caagttcaag      360
gtcgaggtcc ccaagggcat cgcggtgacc aaggacggcg agaagaccga cctgaccggg      420
aagagctga                                                               429
```

<210> SEQ ID NO 49
<211> LENGTH: 142
<212> TYPE: PRT
<213> ORGANISM: Streptomyces hygroscopicus

<400> SEQUENCE: 49

```
Val His His Pro Val Thr Leu Glu Glu Pro Met Phe Ser Gly Thr Ile
1               5                   10                  15

Ser Lys Arg Pro Ala Thr Leu Val Val Ala Val Ala Ala Val Ala Ala
            20                  25                  30

Thr Leu Gly Leu Ser Gly Cys Ser Val Asp Ala Ser Lys Ala Lys Pro
        35                  40                  45

Glu Ser Lys Ser Phe Thr Tyr Ser Gly Lys Ser Leu Lys Val Thr Thr
    50                  55                  60

His Glu Val Ala Thr Lys Val Val Ala Ala Asp Arg Lys Asp Ile Lys
65                  70                  75                  80

Val Thr Arg Trp Phe Asp Ser Ala Ala Gly Thr Glu His Leu Lys Trp
                85                  90                  95

Thr Leu Lys Gly Asp Thr Leu Asp Ile Asp Ala Gly Cys Ser Gly Ile
            100                 105                 110

Ala Ile Cys Asp Ala Lys Phe Lys Val Glu Val Pro Lys Gly Ile Ala
        115                 120                 125

Val Thr Lys Asp Gly Glu Lys Thr Asp Leu Thr Gly Lys Ser
    130                 135                 140
```

<210> SEQ ID NO 50
<211> LENGTH: 1173
<212> TYPE: DNA
<213> ORGANISM: Streptomyces hygroscopicus

<400> SEQUENCE: 50

```
atggattacg acgttcctcc ccggcaaaag cgccgccggt ggtgcggggt ggccgcggca       60
atgatgctcg cccccgccgt catagcgcca ccgagcgcct atctgctggg ggtcatggcc      120
gcattgacgc tggccgtatc gatacttgcc tggccgaccg gccggatctc cctggcccag      180
gcggcgggcg cgtcgcgct gctctccctc gccgcggacg tcggctactt cgggcagccc      240
ggcctggtga tcctctggta cccgttcgag acggtcgcgc tgctcgttct cctggagcgg      300
gtggtacgtc atgtgcccag ccccggggtg ggcatcgtcg cccgctgac cggcgcagcc      360 gtcatcctgc tgcccctgcg cttcaccctg cacgccccca ccgccgggct caaggaatcg      420
gtcttcgcgg ccttgctggc cctgatcccg gcggcctgcg cgacgggtgt ggggctctat      480
ctgcggtcgc tggacaaccg ccgggcgtat gccgtggtgc tggcgcgccg tgaacagcgc      540
ctcgaagtcg cccgcgatct gcatgacttc gtcgcccacg aggtgaccgg catcgttctg      600
gaggcccagg ccgcccaagt cagcgaggac gccgggcccg aggagcaccg cgcccttctg      660
cagcgcatcg agaaggccgg gctacgggcg ctggactcca tggaccagac ggtgacgacg      720
```

-continued

```
ctgcgcgagg cggacggccg caagtggggc gagccgccgc ccacccggct ctacggcttg    780
gccgacctcc ccgagctcgt cggccgcttc tcctccatgg ccgccgccga ggtggcgctg    840
tccctggagg acgaggtcgc cggcaccctc tcgcggagg ccgaggacac cgcgtaccgg     900
gtggtacttg aatcgttgac caatgtccgt cggcatgcgc cgcaggccgg ccgggtccag    960
gtgttcgccg acggaccgcc cgaccgggcc gtggaggtct cggtcgccga caacgcaggg   1020
ccgggggcgt ccgccggcac ccggcagggc ggcggtacgg gcctggcggg cctcggcgaa   1080
cgcgtcagcg ccctgggcgg ctccctggag gcgggcccgt acgagaacgg gtggcgggtc   1140
aggtgcctgc tgccggcgcc cgccatccgc tga                                1173
```

<210> SEQ ID NO 51
<211> LENGTH: 390
<212> TYPE: PRT
<213> ORGANISM: Streptomyces hygroscopicus

<400> SEQUENCE: 51

```
Met Asp Tyr Asp Val Pro Pro Arg Gln Lys Arg Arg Arg Trp Cys Gly
1               5                  10                  15

Val Ala Ala Ala Met Met Leu Ala Pro Ala Val Ile Ala Pro Pro Ser
            20                  25                  30

Ala Tyr Leu Leu Ala Val Met Ala Ala Leu Thr Leu Ala Val Ser Ile
        35                  40                  45

Leu Ala Trp Pro Thr Gly Arg Ile Ser Leu Ala Gln Ala Ala Gly Gly
    50                  55                  60

Val Ala Leu Leu Ser Leu Ala Ala Asp Val Gly Tyr Phe Gly Gln Pro
65                  70                  75                  80

Gly Leu Val Ile Leu Trp Tyr Pro Phe Glu Thr Val Ala Leu Leu Val
                85                  90                  95

Leu Leu Glu Arg Val Val Arg His Val Pro Ser Pro Arg Val Gly Ile
            100                 105                 110

Val Ala Pro Leu Thr Gly Ala Ala Val Ile Leu Leu Pro Leu Arg Phe
        115                 120                 125

Thr Leu His Ala Pro Thr Ala Gly Leu Lys Glu Ser Val Phe Ala Ala
    130                 135                 140

Leu Leu Ala Leu Ile Pro Ala Ala Cys Ala Thr Gly Val Gly Leu Tyr
145                 150                 155                 160

Leu Arg Ser Leu Asp Asn Arg Arg Ala Tyr Ala Val Val Leu Ala Arg
                165                 170                 175

Arg Glu Gln Arg Leu Glu Val Ala Arg Asp Leu His Asp Phe Val Ala
            180                 185                 190

His Glu Val Thr Gly Ile Val Leu Glu Ala Gln Ala Gln Val Ser
        195                 200                 205

Glu Asp Ala Gly Pro Glu His Arg Ala Leu Gln Arg Ile Glu
    210                 215                 220

Lys Ala Gly Leu Arg Ala Leu Asp Ser Met Asp Gln Thr Val Thr Thr
225                 230                 235                 240

Leu Arg Glu Ala Asp Gly Arg Lys Trp Gly Glu Pro Pro Thr Arg
                245                 250                 255

Leu Tyr Gly Leu Ala Asp Leu Pro Glu Leu Val Gly Arg Phe Ser Ser
            260                 265                 270

Met Ala Ala Ala Glu Val Ala Leu Ser Leu Glu Asp Glu Val Ala Gly
        275                 280                 285
```

```
Thr Leu Ser Arg Glu Ala Glu Asp Thr Ala Tyr Arg Val Val Leu Glu
    290                 295                 300

Ser Leu Thr Asn Val Arg Arg His Ala Pro Gln Ala Gly Arg Val Gln
305                 310                 315                 320

Val Phe Ala Gly Arg Thr Ala Asp Arg Ala Val Glu Val Ser Val Ala
                325                 330                 335

Asp Asn Ala Gly Pro Gly Ala Ser Ala Gly Thr Arg Gln Gly Gly Gly
            340                 345                 350

Thr Gly Leu Ala Gly Leu Gly Glu Arg Val Ser Ala Leu Gly Gly Ser
        355                 360                 365

Leu Glu Ala Gly Pro Tyr Glu Asn Gly Trp Arg Val Arg Cys Leu Leu
    370                 375                 380

Pro Ala Pro Ala Ile Arg
385                 390

<210> SEQ ID NO 52
<211> LENGTH: 669
<212> TYPE: DNA
<213> ORGANISM: Streptomyces hygroscopicus

<400> SEQUENCE: 52
gtgactattc gcttgctgat cgccgacgac caggagatgg tccgccgcgg aatacgccgc     60
atcgtggaga gccagcccga catggaagtg gtcggcgagg cggcaaacgg cgtggacgcg    120
gtggagatgg ggcgcacgct caaacccgat gtggcgctgg tcgacatccg gatgccgcgg    180
atggacggcc tggaggtgac cgcctgctg gccgaccccg ccgcgccaa cccggtccgg     240 gtcgtcgtgg tgacgacctt cgacctggac gagtacgtgt accccgcgct gcgcttcggc    300
gcctcggggt tcctgctcaa cgctcgggg ccgacgctgc tggtcgaggc ggtccggcg     360 gcgatggccg gcgacagcct gatcagcccg tcgatcactg tccggctgct ccagcatgtc    420 accggccca cgaccggccg ccgccccgc cgccgtgact cggtgctgac cgagcgggag     480
gtggagatcg ccgggaaggt cgccgagggc aagaccaatt ccgatatcgc ccgcgagttg    540
ttcatctccg cgggcacggt caagacccat gtcgcgagca ttcagcgaaa gctacaggta    600
cgcaatcgcg tcggggtcgc ggtgcgggcc tgggagctcg gatatgccac cgggcagacc    660
ccggggtga                                                           669

<210> SEQ ID NO 53
<211> LENGTH: 222
<212> TYPE: PRT
<213> ORGANISM: Streptomyces hygroscopicus

<400> SEQUENCE: 53

Val Thr Ile Arg Leu Ile Ala Asp Asp Gln Glu Met Val Arg Arg
1               5                   10                  15

Gly Ile Arg Arg Ile Val Glu Ser Gln Pro Asp Met Glu Val Val Gly
                20                  25                  30

Glu Ala Ala Asn Gly Val Asp Ala Val Glu Met Gly Arg Thr Leu Lys
            35                  40                  45

Pro Asp Val Ala Leu Val Asp Ile Arg Met Pro Arg Met Asp Gly Leu
    50                  55                  60

Glu Val Thr Arg Leu Leu Ala Asp Pro Ala Ala Asn Pro Val Arg
65                  70                  75                  80

Val Val Val Val Thr Thr Phe Asp Leu Asp Glu Tyr Val Tyr Pro Ala
                85                  90                  95
```

```
Leu Arg Phe Gly Ala Ser Gly Phe Leu Leu Lys Arg Ser Gly Pro Thr
            100                 105                 110
Leu Leu Val Glu Ala Val Arg Ala Ala Met Ala Gly Asp Ser Leu Ile
        115                 120                 125
Ser Pro Ser Ile Thr Val Arg Leu Leu Gln His Val Thr Gly Pro Thr
    130                 135                 140
Thr Gly Arg Arg Pro Arg Arg Asp Ser Val Leu Thr Glu Arg Glu
145                 150                 155                 160
Val Glu Ile Ala Gly Lys Val Ala Glu Gly Lys Thr Asn Ser Asp Ile
                165                 170                 175
Ala Arg Glu Leu Phe Ile Ser Ala Gly Thr Val Lys Thr His Val Ala
            180                 185                 190
Ser Ile Gln Arg Lys Leu Gln Val Arg Asn Arg Val Gly Val Ala Val
        195                 200                 205
Arg Ala Trp Glu Leu Gly Tyr Ala Thr Gly Gln Thr Pro Gly
    210                 215                 220

<210> SEQ ID NO 54
<211> LENGTH: 990
<212> TYPE: DNA
<213> ORGANISM: Streptomyces hygroscopicus

<400> SEQUENCE: 54
gtgctgagga tccacttcac agttgaggac atagcaaata cgcgcatgct ggcgaccctc      60
gggccgctgg ccgagagcgc tttcgcgctc tatctgttcg ccgtaacggc gatgtcgcc     120
tttcacgagt ggcgtcgcag tgtccgcgcc gaactcggca aggacgcggc ccgcttcacg     180
gccttgtccc agcagttccg gaccctggag gaattacctg ccgccttcgc cgacgccttc     240
acgccggggg cggaccccga ccaggttccg tccggcgagg accggcgcgg cgccaggctg     300
ctggccgacc tgtgccgggt ggccgtgctg ccgcactgga gcctgatccg cagtcatctc     360
gacggtgcgc gcgagggctg gggcagggtg gccatctcgc acggtgtcga gcggctgctg     420
ggctccgtgc accccaaggt ccgctggcgg gcgccggtcc tcgaactgcg cacgggccc     480
aaccgcgaca tccatctgga cggtcgcggg ttgctgctgt gcccgtcgtt cttcctgtcg     540
gagcagtcct gttcgttcgt gacggcggtc ggcaaggacg ccatgcccgc ccttgtcttc     600
cccgtgaagg cctcgtccag ggtggacatc tggggtacct cggaacacga cgagcaggcg     660
ctggcgcac tggtcgggca caccaggggcg ccgccctgg aagcgctcgc cgagggctgc     720
tccacgggcg aactcgccga ccggctgggg atctcgctgg ccggtgccag caagcatgcc     780
gcggtgctgc gacgatccgg gctggtgacc acctcccgta accgcaacac gcgctgcac     840
gcgctcaccc ctctgggcac cgccctgctc cgcagcagcg accgcttcat ctcgccgcct     900
accgccccgg tatcgcgcgt gccggcgcaa cgcatgcggc ccttgcagct caacggcatc     960
ggccccggca ccaaccgggc ggcggtctga                                       990

<210> SEQ ID NO 55
<211> LENGTH: 329
<212> TYPE: PRT
<213> ORGANISM: Streptomyces hygroscopicus

<400> SEQUENCE: 55

Val Leu Arg Ile His Phe Thr Val Glu Asp Ile Ala Asn Thr Arg Met
1               5                   10                  15
Leu Ala Thr Leu Gly Pro Leu Ala Glu Ser Ala Phe Ala Leu Tyr Leu
            20                  25                  30
```

-continued

```
Phe Gly Arg Asn Gly Asp Val Ala Phe His Glu Trp Arg Arg Ser Val
            35                  40                  45
Arg Ala Glu Leu Gly Lys Asp Ala Ala Arg Phe Thr Ala Leu Ser Gln
 50                  55                  60
Gln Phe Arg Thr Leu Glu Glu Leu Pro Ala Ala Phe Ala Asp Ala Phe
 65                  70                  75                  80
Thr Pro Gly Ala Asp Pro Asp Gln Val Pro Ser Gly Glu Asp Arg Arg
                 85                  90                  95
Gly Ala Arg Leu Leu Ala Asp Leu Cys Arg Val Ala Val Leu Pro His
                100                 105                 110
Trp Ser Leu Ile Arg Ser His Leu Asp Gly Ala Arg Glu Gly Trp Gly
            115                 120                 125
Arg Val Ala Ile Ser His Gly Val Glu Arg Leu Leu Gly Ser Val His
130                 135                 140
Pro Lys Val Arg Trp Arg Ala Pro Val Leu Glu Leu Arg His Gly Pro
145                 150                 155                 160
Asn Arg Asp Ile His Leu Asp Gly Arg Gly Leu Leu Cys Pro Ser
                165                 170                 175
Phe Phe Leu Ser Glu Gln Ser Cys Ser Phe Val Thr Ala Val Gly Lys
            180                 185                 190
Asp Ala Met Pro Ala Leu Val Phe Pro Val Lys Ala Ser Ser Arg Val
            195                 200                 205
Asp Ile Trp Gly Thr Ser Glu His Asp Glu Gln Ala Leu Gly Ala Leu
210                 215                 220
Val Gly His Thr Arg Ala Ala Ala Leu Glu Ala Leu Ala Glu Gly Cys
225                 230                 235                 240
Ser Thr Gly Glu Leu Ala Asp Arg Leu Gly Ile Ser Leu Ala Gly Ala
                245                 250                 255
Ser Lys His Ala Ala Val Leu Arg Arg Ser Gly Leu Val Thr Thr Ser
            260                 265                 270
Arg Asn Arg Asn Thr Ala Leu His Ala Leu Thr Pro Leu Gly Thr Ala
            275                 280                 285
Leu Leu Arg Ser Ser Asp Arg Phe Ile Ser Pro Thr Ala Pro Val
290                 295                 300
Ser Arg Val Pro Ala Gln Arg Met Arg Pro Leu Gln Leu Asn Gly Ile
305                 310                 315                 320
Gly Pro Gly Thr Asn Arg Ala Ala Val
                325

<210> SEQ ID NO 56
<211> LENGTH: 411
<212> TYPE: DNA
<213> ORGANISM: Streptomyces hygroscopicus

<400> SEQUENCE: 56
gtgcgggccg tgtgcgaagt cctggccggc ctcgccgagc gcaccccca gccgccgccc      60 ccggcgtccg gccgcaccgc ccaggaagcc ctgggcgcgt cgcccgcgc atgggtcgcc     120 cggctcccgc tcgccaccga tgagcaccgg gcggccggga tcggcatggt cctgatgccg     180
gagatcctcg ccgacgcacg aacccgcctg ccgttcgccc aactgatgaa gctcaacgcg     240
atcctgctcg gactcgcccc ggagcgtctg caccggcccg aagcctccgc ccccgcctg     300 gtacgcgtcg cggaagccac ctcaccaccc tgcacggcgc gagccaactg gccgacgccg     360 caccggctt caccgaaccc ttcgacatcg tcagcgcctg cgagcggctg a              411
```

<210> SEQ ID NO 57
<211> LENGTH: 136
<212> TYPE: PRT
<213> ORGANISM: Streptomyces hygroscopicus

<400> SEQUENCE: 57

```
Val Arg Ala Val Cys Glu Val Leu Ala Gly Leu Ala Glu Arg Thr Pro
1               5                   10                  15

Gln Pro Pro Pro Ala Ser Gly Arg Thr Ala Gln Glu Ala Leu Gly
            20                  25                  30

Ala Phe Ala Arg Ala Trp Val Ala Arg Leu Pro Leu Ala Thr Asp Glu
            35                  40                  45

His Arg Ala Ala Gly Ile Gly Met Val Leu Met Pro Glu Ile Leu Ala
        50                  55                  60

Asp Ala Arg Thr Arg Leu Pro Phe Ala Gln Leu Met Lys Leu Asn Ala
65                  70                  75                  80

Ile Leu Leu Gly Leu Ala Pro Glu Arg Leu His Arg Pro Glu Ala Ser
                85                  90                  95

Ala Pro Arg Leu Val Arg Val Ala Glu Ala Thr Ser Pro Pro Cys Thr
            100                 105                 110

Ala Arg Ala Asn Trp Pro Thr Pro His Pro Ala Ser Pro Asn Pro Ser
            115                 120                 125

Thr Ser Ser Ala Pro Ala Ser Gly
        130                 135
```

NON-RIBOSOMAL PEPTIDE SYNTHETASES AND ASSOCIATED BIOSYNTHETIC GENES

This application is a Continuation-In-Part of U.S. patent application Ser. No. 10/402,842, filed on Mar. 28, 2003, which claims the benefit of Provisional Patent Application Ser. No. 60/368,713, filed on Mar. 29, 2002, the disclosures of which are herein incorporated by reference in their entirety.

FIELD OF THE INVENTION

The present invention relates to non-ribosomal peptide synthetases and associated biosynthetic genes. The present invention further relates to methods for generating novel compounds, such as antibiotics, with these synthetases and associated genes.

BACKGROUND OF THE INVENTION

Bioactive molecules that are isolated from plants, bacteria, and fungi are often referred to as natural products. These molecules are synthesized by primary or secondary pathways within the organism or may even be degradation products of another molecule. Many of these molecules have shown a variety of therapeutic uses in humans and other animal species. One of the best known examples is taxol, which was originally isolated from the bark of the Pacific Yew tree. Taxol has been shown to have anti-cancer properties and is currently used in the treatment of breast cancer. Actinomycetes are prolific producers of bioactive small molecules. These molecules may be used chemically as immunosuppressants, antibiotics, and cancer therapeutics. Actinomycetes are Gram-positive bacteria that form long, thread-like branched filaments. The term actinomycetes is used to indicate organisms belonging to Actinomycetales, an Order of the domain Bacteria. The Actinomycetales are divided into 34 Families including Streptomyceteae, to which belongs the Genus *Streptomyces* (Bergey's Manual of Systematic Bacteriology, Second Edition, 2001; George M. Garrity, Editor-in-Chief, Springer Verlag, New York).

Natural products derived from microbial sources primarily belong to three metabolic families: peptides, polyketides, and terpenes. Peptide natural products can be further classified based on their mode of synthesis: ribosomal and non-ribosomal. Non-ribosomal peptides are synthesized on enzymatic thiotemplates termed non-ribosomal peptide synthetases (NRPS). The non-ribosomal peptides encompass a wide range of compounds having diverse activities including, but not limited to, immunosupressive (such as cyclosporin), surfactant (such as surfactin), siderophores (such as enterobactin), virulence factors (such as yersinabactin), antibacterial (such as penicillin and vancomycin), and anti-cancer (such as actinomycin and bleomycin) activities (Weber et al., Current Genomics 1994; 26:120–25; Ehmann et al., Proc. Nat. Acad. Sci. 2000; 97:2509–14; Gehring et al., Biochemistry 1998; 37:11637; Kallow et al., Biochemistry 1998; 37:5947–52; Trauger et al., Proc. Nat. Acad. Sci. 2000; 97:3112–17; Schauweker et al., J. Bacteriology 1999; 27:2468–74; and Shen et al., Bioorganic Chem 1999; 27:155–71). Non-ribosomal peptides typically range in size from 1–11 amino acids and are produced by a variety of microbes including cyanobacteria, actinomycetes and fungi.

In many cases the non-ribosomal peptides contain non-proteogenic amino acids such as norleucine, β-alanine, ornithine, etc., for which biogenesis pathways, which are secondary to primary metabolism, are required and are post-synthetically modified (e.g., hydroxylated or methylated) by tailoring enzymes. As used herein, the term "proteogenic" indicates that the amino acid can be incorporated into a protein in a cell through well-known metabolic pathways. The choice of including a (D)- or (L)-amino acid into a peptide of the present invention depends, in part, on the desired characteristics of the peptide. For example, the incorporation of one or more (D)-amino acids can confer increasing stability on the peptide in vitro or in vivo. As used herein, the term "amino acid equivalent" refers to compounds which depart from the structure of the naturally occurring amino acids, but which have substantially the structure of an amino acid, such that they can be substituted within a peptide that retains biological activity. Thus, for example, amino acid equivalents can include amino acids having side chain modifications and/or substitutions, and also include related organic acids, amides or the like. The term "amino acid" is intended to include amino acid equivalents. The term "residues" refers both to amino acids and amino acid equivalents.

The genes required to make a NRPS and the necessary tailoring enzymes have been shown in all cases to be localized to the chromosome of the producing microbe. NRPSs are modular in nature, where a module may be defined as a segment of the NRPS necessary to catalyze the activation of a specific amino acid and result in the incorporation of that amino acid into a non-ribosomal peptide. A minimal module contains three domains: (1) adenylation domains (about 60 kDa), responsible for selecting and activating an amino acid and transferring the aminoacyl adenylate to a peptidyl carrying center; (2) thiolation domains, also referred to as peptidyl carrier proteins (8–10 kDa), containing a serine residue which is post-translationally modified with a 4-phosphopantetheine group (Ppant) which acts as an acceptor for the aminoacyl adenylate; and (3) condensation domains (50–60 kDa) which catalyze peptide bond-forming chain-translocating steps between an upstream peptidyl-s-Ppant and the downstream aminoacyl-Ppant of the adjacent module (Doekel, S. and Maraheil, M. A. 2000; Chem. Biol. 7:373–384). This minimal module for chain extension is typically repeated within a synthetase and a co-linear relationship exists between the number of modules present and the number of amino acids in the final product with the order of the modules in the synthetase determining the order of the amino acids in the peptide.

There is a continuing need in the art to determine the genes encoding NRPS complexes.

SUMMARY OF THE INVENTION

The present invention provides the nucleic acid and amino acid sequences of a non-ribosomal peptide synthetase (NRPS) complex from *Streptomyces hygroscopicus*. The NRPS described herein is comprised of two components, designated MppA (SEQ ID NO:2) and MppB (SEQ ID NO:4), and contains the sequences required for the biosynthesis of the peptide core of lipoglycopeptide antibiotic AC98.

The present invention also provides characterization of MppA (SEQ ID NO:2) and MppB (SEQ ID NO:4), including the number of modules in each component and the functional domains contained within each module. In particular, MppA (SEQ ID NO:2) is comprised of three modules, each containing an adenylation, thiolation, and condensation domain, and MppB (SEQ ID NO:4) is comprised of two modules, two epimerization domains, and a partial module comprised only of a condensation domain and thiolation domain.

Further provided by the present invention are expression vectors comprising the genes encoding MppA (SEQ ID NO:2) and MppB (SEQ ID NO:4), and host cells transfected with such MppA (SEQ ID NO:2) and/or MppB (SEQ ID NO:4)-encoding vectors.

The present invention also provides nucleic acid and amino acid sequences for several open reading frames (ORFs) encoding associated gene products that modify the amino acids of the core peptide post-biosynthesis, as well as host cells comprising the ORFs.

In yet a further embodiment, the present invention provides a method for producing the NRPS described herein, which method comprises culturing an NPRS-transformed host cell under conditions that provide for expression of MppA (SEQ ID NO:2) and MppB (SEQ ID NO:4).

The present invention further provides a method of producing a cyclic peptide synthesized by of the NRPS comprised of MppA (SEQ ID NO:2) and MppB (SEQ ID NO:4), which peptide is an antibiotic. In a preferred embodiment, the antibiotic is AC98.

Also provided by the present invention are methods of modifying the adenylation domains of NRPS in order to produce an antibiotic having a modified peptide core, and a method for evaluating the structural regions of the modified peptide.

BRIEF DESCRIPTION OF DRAWINGS

FIG. 4A shows the serine-specific binding pocket of the adenylation domain of module 1 within MppA (SEQ ID NO:2). FIG. 4B shows the glycine-specific binding pocket of the adenylation domain of module 2 within MppA (SEQ ID NO:2). FIG. 4C shows the phenylalanine-specific binding pocket of the adenylation domain of module 3 within MppA (SEQ ID NO:2). FIG. 4D shows the tyrosine-specific binding pocket of the adenylation domain of module 1 within MppB (SEQ ID NO:4). FIG. 4E shows the cyclo-arginine-specific binding pocket of the adenylation domain of module 2 within MppB (SEQ ID NO:4).

DETAILED DESCRIPTION OF THE INVENTION

The following definitions are The following definitions are provided for the full understanding of terms and abbreviations used in this specification.

The abbreviations in the specification correspond to units of measure, techniques, properties or compounds as follows: "min" means minutes, "h" means hour(s), "µL" means microliter(s), "mL" means milliliter(s), "mM" means millimolar, "M" means molar, "mmole" means millimole(s), "kb" means kilobase, "bp" means base pair(s), and "IU" means International Units. "Polymerase chain reaction" is abbreviated PCR; "Reverse transcriptase polymerase chain reaction" is abbreviated RT-PCR; "Estrogen receptor" is abbreviated ER; "DNA binding domain" is abbreviated DBD; "Ligand binding domain" is abbreviated LBD; "Untranslated region" is abbreviated UTR; "Sodium dodecyl sulfate" is abbreviated SDS; and "High Pressure Liquid Chromatography" is abbreviated HPLC.

Figure 1A:
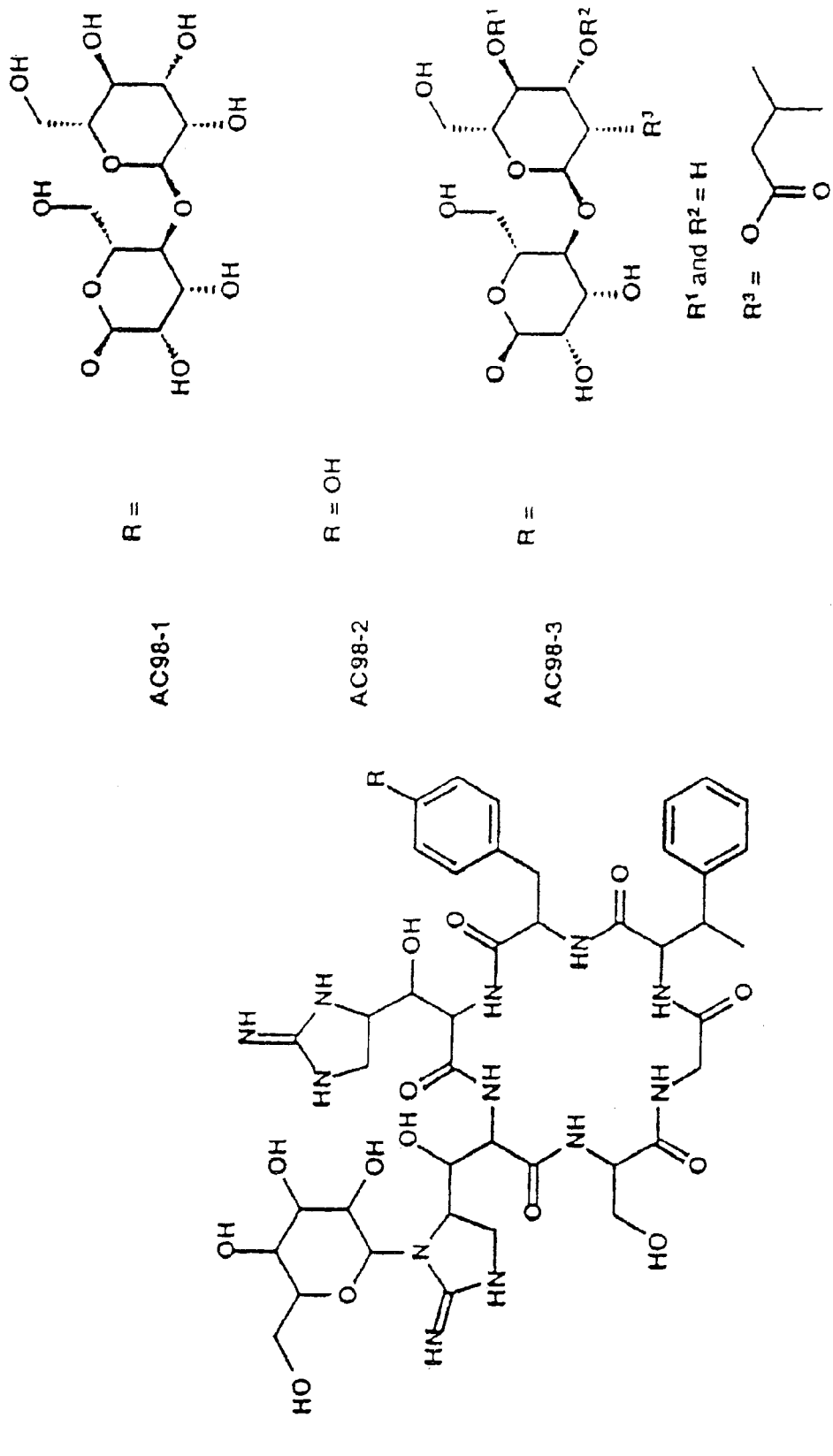
FIGS. 1A–B depict the chemical structures of the lipoglycopeptide antibiotic AC98.
Figure 1B:
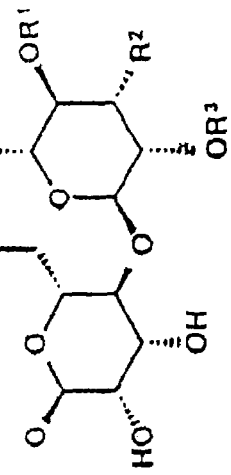
Figure 1B:
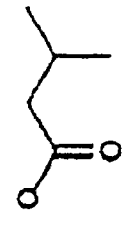
Figure 1B:
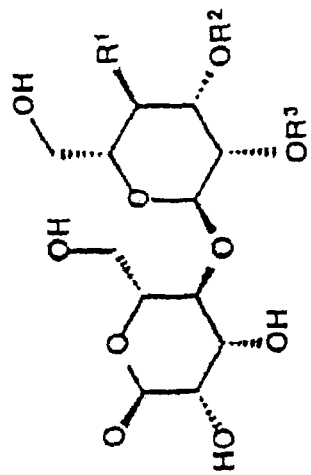
Figure 1B:
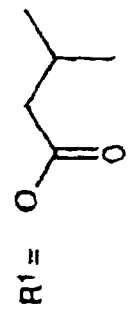
Figure 2:
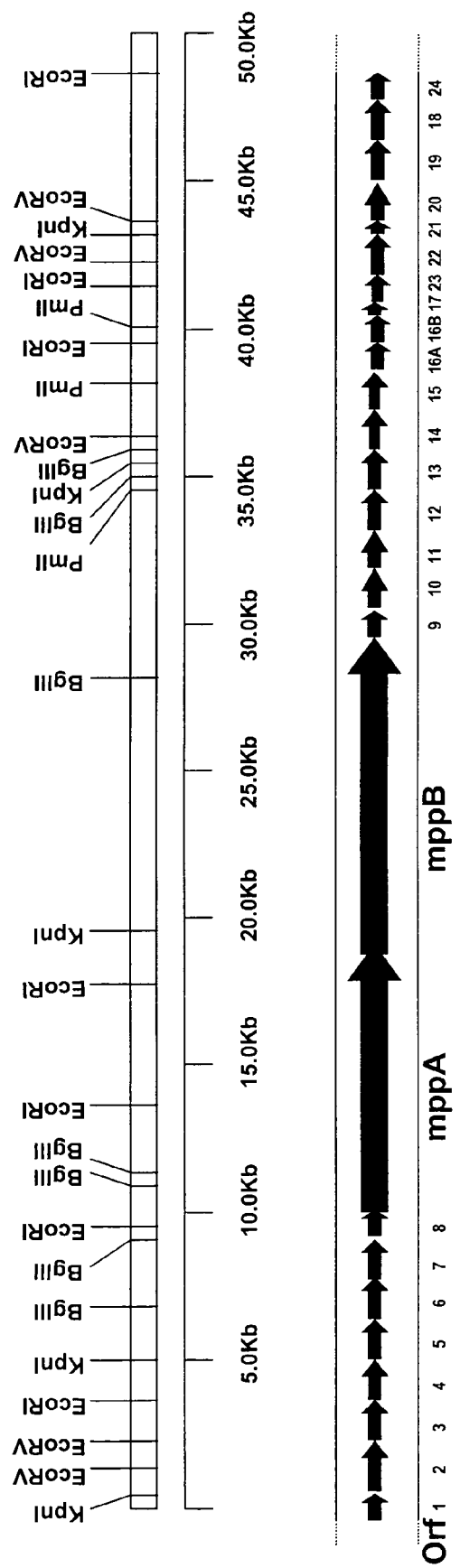
FIG. 2 shows a representation of the NRPS complex from this *Streptomyces hygroscopicus* strain NS17 that is demonstrated to be the minimal biosynthetic machinery responsible for the biosynthesis of the peptide core of AC98.

*Streptomyces hygroscopicus* NS17 is a terrestrial actinomycete which produces a novel lipoglycopeptide antibiotic complex (AC98; See FIG. 1). This strain has been deposited with the Agricultural Research Service Culture Collection, 1815 North University St., Peoria, Ill. 61604, Deposit No. NRRL 30439. This antibiotic has been shown to be active against Gram-positive pathogens including, but not limited to, vancomycin resistant enterococci (VRE), methicillin resistant *Staphlococcus aureus* (MRSA) and *Streptococcus pneumoniae*. The present invention is based on the isolation of the genes encoding a novel NRPS complex from this *Streptomyces* strain that is demonstrated to be the minimal biosynthetic machinery responsible for the biosynthesis of the peptide core of AC98 (see FIG. 2).

Figure 3:
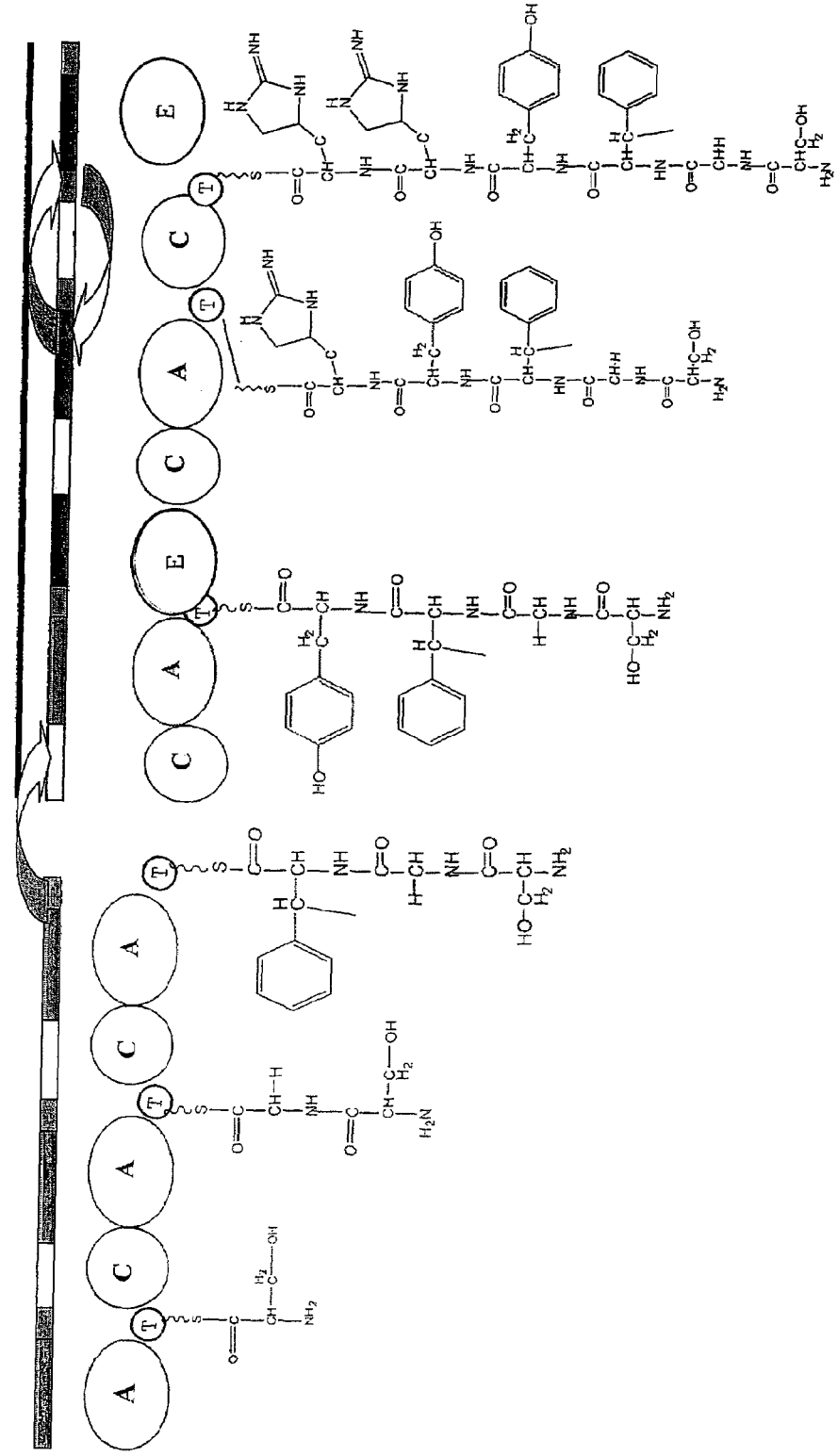
FIG. 3 is a pictorial representation of the biosynthesis of the AC98 peptide core by the novel NRPS described herein.
Figure 4A:
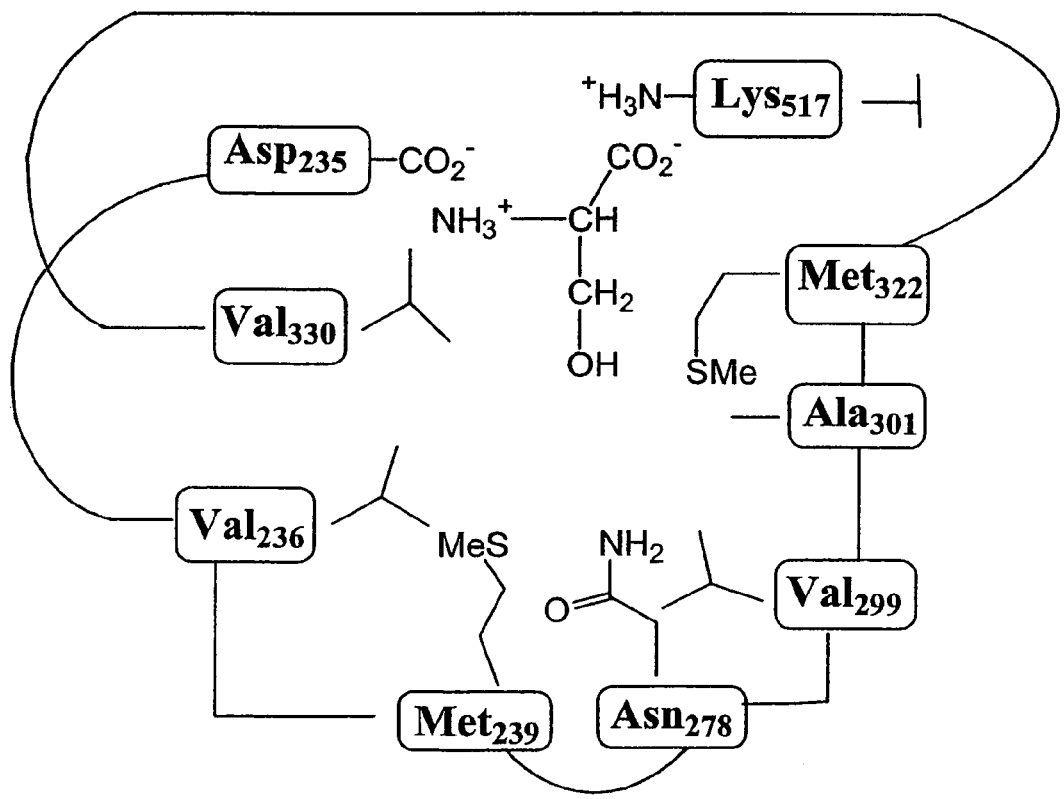
FIGS. 4A–E depicts the two-dimensional representation of the binding pockets of adenylation domains within modules of the NRPS of the invention. Amino acid residues 235, 236, 239, 278, 299 & 301, are those that determine the specificity of the binding pocket.
Figure 4B:
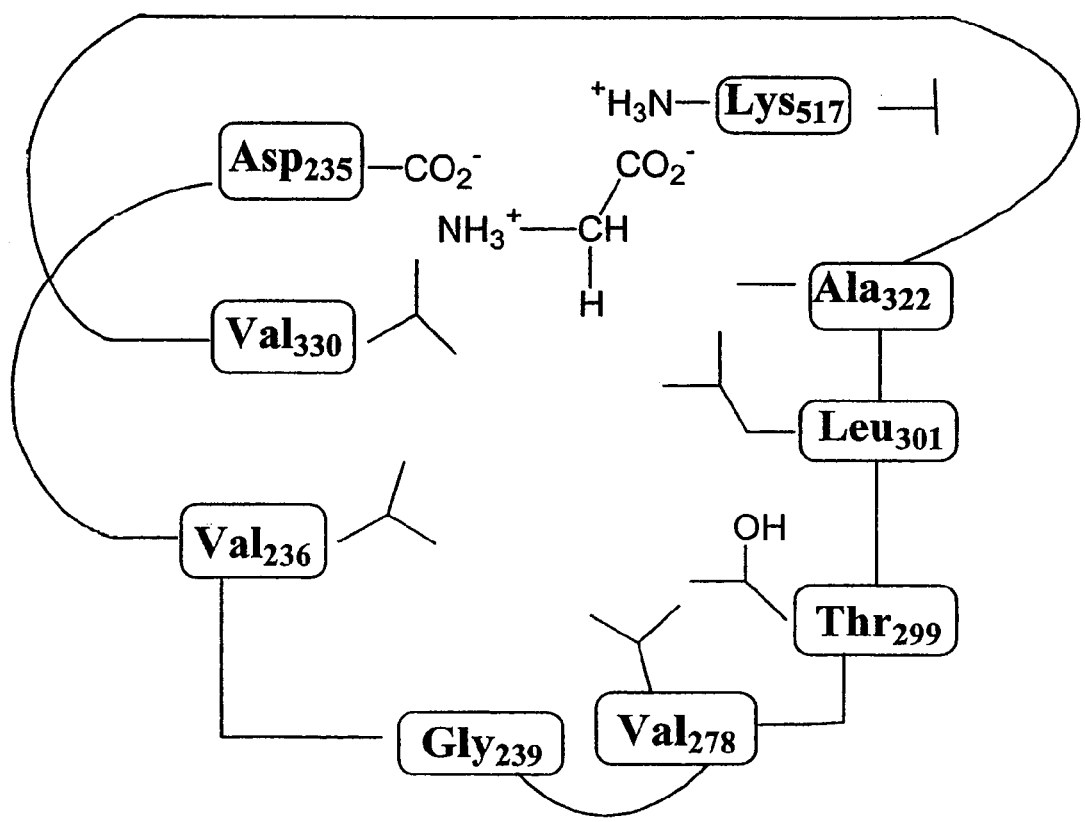
Figure 4C:
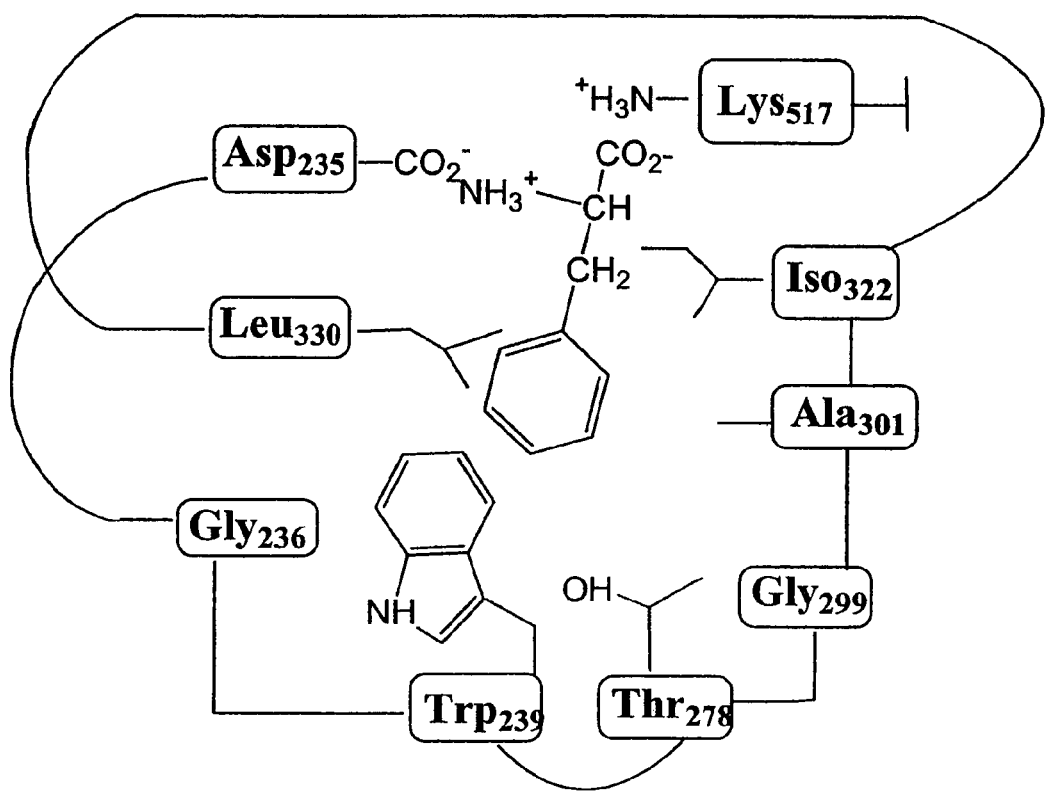
Figure 4D:
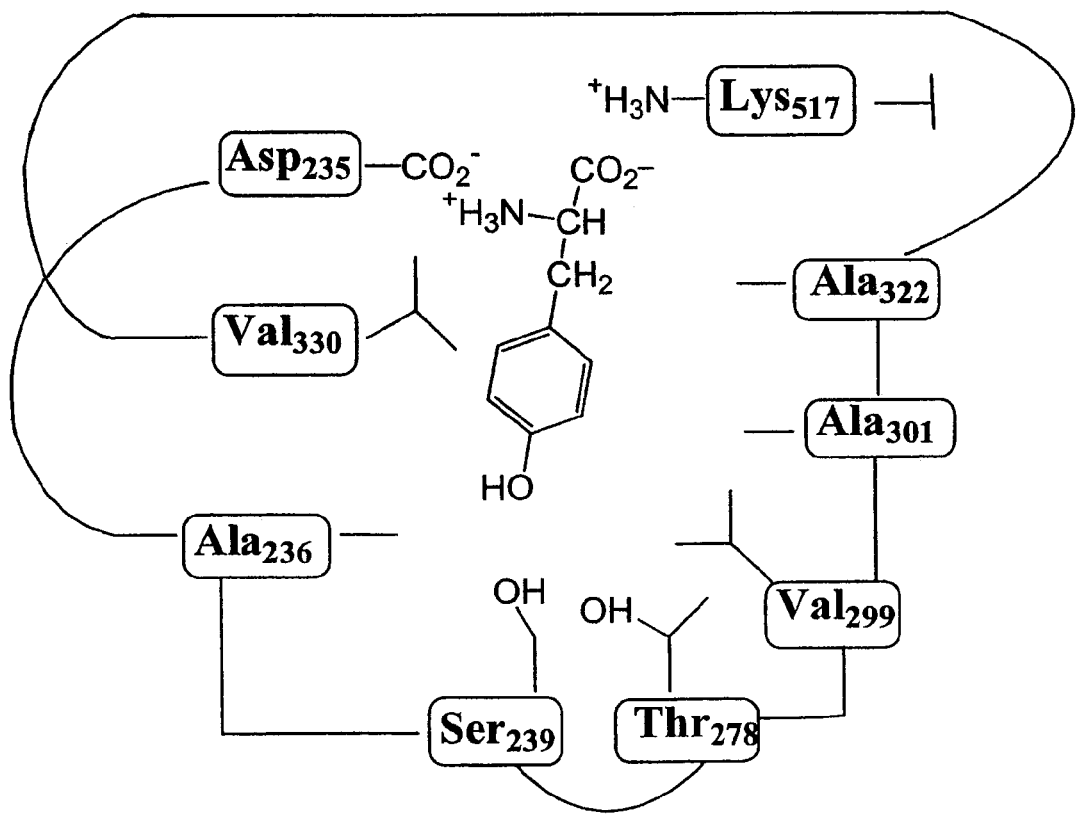
Figure 4E:
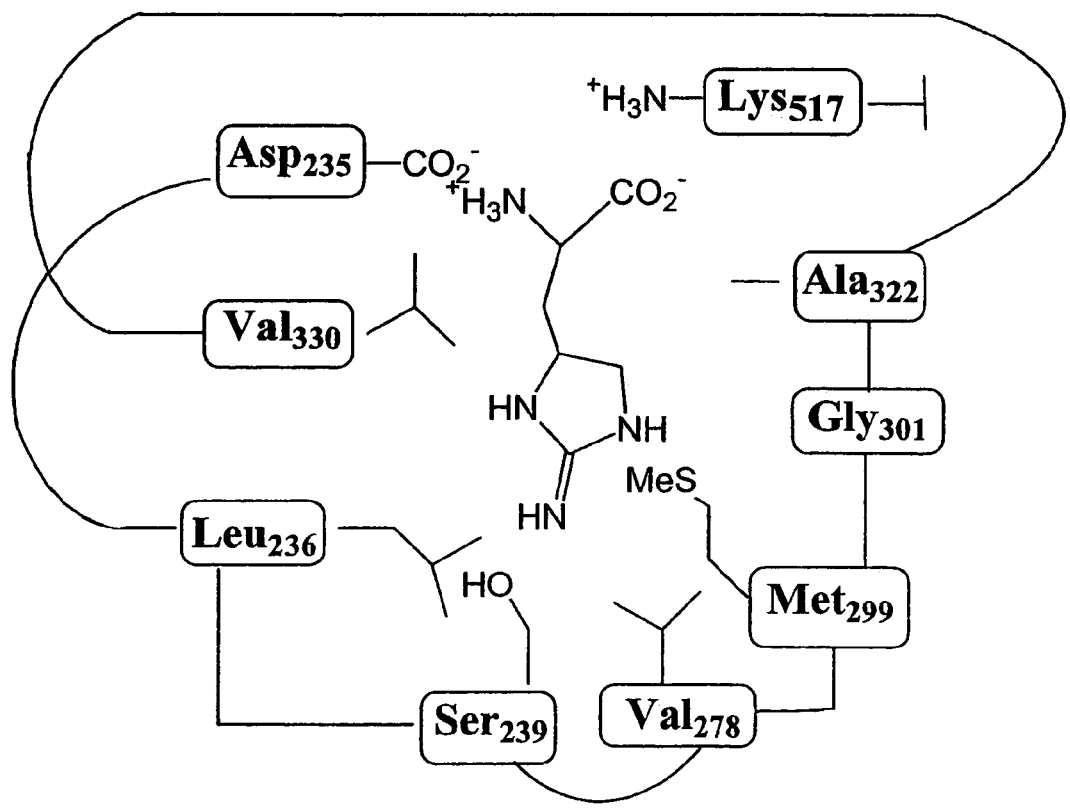

A number of open reading frames (ORFs), that are predicted to play a role in the biosynthesis of AC98, have been isolated and characterized by sequence analysis. Sequence comparisons of specific ORFs indicate that the proteins that are encoded by the ORFs are tailoring enzymes that are involved in such modifications of the peptide core as glycosylation, methylation and acylation. Other ORFs putatively encode enzymes that may be involved in resistance. A detailed description of the NRPS and its function in biosynthesis of the AC98 peptide core is presented in FIG. 3. The genes required to make the NRPS and the necessary tailoring enzymes are localized to the chromosome of the producing microbe.

NRPS

The NRPS enzymes are generally composed of modules where a minimal module contains three domains, an adenylation domain, a thiolation domain, and a condensation domain.

The adenylation domain is typically about 60 kDa. The main function of this domain is to select and activate a specific amino acid as an aminoacyl adenylate. Based on its function, the adenylation domain regulates the sequence of the peptide being produced. Once charged (as an amino acyl adenylate moiety), the amino acid is transferred to a thiolation domain (peptidyl carrying center).

The second domain is the thiolation domain, also referred to as a peptidyl carrier protein. This domain is typically 8–10 kDa and contains a serine residue that is post-translationally modified with a 4-phosphopantetheine group. This group acts as an acceptor for the aminoacyl adenylate moiety on the amino acid. A nucleophilic reaction leads to the release of the aminoacyl adenylate and conjugation of the amino acid to thiolation domain via a thioester bond.

The third domain is the condensation domain. This domain is typically about 50–60 kDa in size. The main function of this domain is to catalyze the formation of a peptide bond between two amino acids. In this reaction an upstream tethered peptidyl group is translocated to the downstream aminoacyl-s-Ppant and linked to the amino acid by peptide bond formation.

This minimal module for chain extension is typically repeated within a synthetase. Additionally, and typically, a co-linear relationship exists between the number of modules present and the number of amino acids in the final product with the order of the modules in the synthetase determining the order of the amino acids in the peptide. This 1:1 relationship, with every amino acid in the product having one module within the enzyme, is referred to as the co-linearity rule. Examples have been found that violate this rule, and in such cases, the NRPS contains more modules than one would expect based on the number of amino acids incorporated in the peptide product (Challis et al., Chem. Biol. 2000; 7:211–24). In some cases the minimal module also is supplemented with additional domains (epimerization, N- or C-methylation, or cyclization domain), with their position in the synthetase determining the substrate upon which they can act. In addition, it has been observed that NRPSs contain inter-domain spacers or linker regions. It has been proposed that these spacers may play a critical role in communication between domains, modules, and even entire synthetases.

There are highly conserved motifs in the catalytic domains of peptide synthetases including: 10 conserved motifs in the adenylation domain; 1 conserved motif in the thiolation domain; 7 conserved motifs in the condensation domain; 1 conserved motif in the thioesterase domain; 7 conserved motifs in the epimerization domains; and 3 conserved motifs in the N-methylation domains. These are detailed in Marahiel et al., Chemical Rev. 1997; 97:2651–73. In addition to modifications such as epimerization, methylation and cyclization during peptide synthesis, post-translational modifications including methylation, hydroxylation, oxidative cross-linking and glycosylation can occur (Walsh et al., Curr. Opin. Chem. Biol. 2001; 5:525–34).

In the present invention, a biosynthetic pathway containing the genes for a NRPS from *Streptomyces hygroscopicus* NS17 has been isolated and characterized (SEQ ID NO:1). The NRPS exists as two separate components that have been termed MppA (SEQ ID NO:2) and MppB (SEQ ID NO:4). These components both are involved in the synthesis of the core of AC98.

MppA (SEQ ID NO:2) is composed of three minimal modules, where each module is comprised of an adenylation, thiolation, and condensation domain. MppA (SEQ ID NO:2) conjugates a serine amino acid to a glycine amino acid to produce a peptide. This peptide is then conjugated (through the glycine) to a phenylalanine amino acid. Each amino acid is incorporated into the peptide chain by a unique module. In one embodiment, MppA (SEQ ID NO:2) is about 295 kDa. In another embodiment, MppA (SEQ ID NO:2) is about 2747 amino acids in length. In one embodiment, MppA has an amino acid sequence as depicted in SEQ ID NO:2. In another embodiment, the MppA protein (SEQ ID NO:2) is encoded by a nucleic acid sequence as depicted in SEQ ID NO:3. After addition of the phenylalanine, the peptide chain is then transferred to the MppB (SEQ ID NO:4) component.

The specificity of each AC98 adenylation domain in the NRPS of the present invention was predicted based on the method described in Challis et al., Chem. Biol. 2000; 7:211–24. Amino acid residues 235, 236, 239, 278, 299 & 301 lining the binding pocket of each adenylation domain were found to define domain specificity (the adenylation domains of MppA (SEQ ID NO:2) and MppB (SEQ ID NO:4) modules are depicted in FIG. 4) and, in turn, the order of amino acid incorporation into the growing AC98 peptide chain (See FIG. 3).

MppB (SEQ ID NO:4) is composed of 2½ modules and two epimerization domains. In other words, MppB (SEQ ID NO:4) is comprised of 2 complete minimal modules (as described above for MppA (SEQ ID NO:2)) and an additional condensation and thiolation domain (which constitutes the ½ module). The peptide chain synthesized by MppA (SEQ ID NO:2) is transferred to MppB (SEQ ID NO:4) where a tyrosine amino acid is added to the chain. Prior to the condensation domain, an epimerization enzyme alters the chirality of the tyrosine residue from an L-amino acid to a D-amino acid. The peptide chain is then transferred to a module where a first cycloarginine moiety is added to the peptide. The module which incorporates the first cycloarginine moiety into the peptide is then reused to incorporate a second cycloarginine moiety. A second epimerization domain then alters the chirality of the second cycloarginine from an L-amino acid to a D-amino acid. The terminal module of MppB (SEQ ID NO:4) is unique in that there is only one adenylation domain used for the addition of two cycloarginine residues to the peptide core.

In one embodiment, MppB (SEQ ID NO:4) is about 394 kDa. In another embodiment, MppB (SEQ ID NO:4) is about 3668 amino acids in length. In one embodiment, mppB has an amino acid sequence as depicted in SEQ ID NO:4. In another embodiment, the MppB (SEQ ID NO:4) protein is encoded by a nucleic acid sequence as depicted in SEQ ID NO: 5. After epimerization, the peptide sequence is then modified by tailoring enzymes including, but not limited to, glycosylation enzymes, methylation enzymes and acylation enzymes.

Tailoring Enzymes

After production of the core of the peptide, the sequence may then be modified by additional enzymes which are herein termed "tailoring enzymes". These enzymes alter the amino acids in the compound without altering the number or the specific amino acids present within the compound. Such tailoring enzymes may include, but are not limited to, arginine cyclase, an O-mannosyltransferase, a phenylalanine C-methyltransferase, a first isovaleryl transferase, and a second isovaleryl transferase.

In the present invention, these tailoring enzymes have been determined to be ORFs present on the AC98 biosynthetic gene cluster and have been termed ORF1–ORF24 (with SEQ ID NOs as described in Table 1). Sequence comparison of these ORFs with homologs provide preliminary information about the function of the enzymes. Table 1 below provides a correlation between the ORF, its location within SEQ ID NO: 1, and its proposed function.

The present invention permits specific changes to be made to the ORFs that encode the tailoring enzymes, either by site directed mutagenesis or replacement, to genetically modify the peptide core. The modifications may be made in a rational manner to improve the biological activity of the antibiotic produced by the bacterial strain or to direct synthesis of compounds that are structurally related to AC98. The invention also allows for the ORFs encoding tailoring enzymes to be isolated and used for biotransformation experiments to produce enzymes to modify and possibly improve other useful compounds.

The determination of the entire biosynthetic pathway of AC98 also enables one of ordinary skill in the art to clone and express the pathway into a heterologous organism. Any organism may be used; preferably a bacterial strain is used. The choice of organism is dependent upon the needs of the skilled artisan. For example, a strain that is amenable to genetic manipulation may be used in order to facilitate modification and production of AC98.

The present invention advantageously permits specific changes to be made to individual modules of NRPS, either by site directed mutagenesis or replacement, to genetically modify the peptide core. Additionally, the NRPS modules can be used to modify other NRPSs that direct the synthesis of other useful peptides through module swapping. For example, the module in NRPS that incorporates tyrosine into the peptide core of the antibiotic may be modified so as to incorporate a serine in its place.

TABLE 1

ORF Correlation

| Orf | Position (bp) | No. Amino Acids | Sequence Homolog Accession No.* | Percent Identity | Proposed Function |
|---|---|---|---|---|---|
| orf1 (SEQ ID NO:6) | 77–1048 | 323 (SEQ ID NO:21) | BAB69251 Pfam PF00583 | 68% | Acetyltransferase |
| orf2 (SEQ ID NO:7) | 1045–2460 | 471 (SEQ ID NO:22) | BAB69250 Pfam PF01574 | 61% | ABC transporter |
| orf3 (SEQ ID NO 8) | 2495–3406 | 303 (SEQ ID NO:23) | BAB69249 Pfam PF00528 | 70% | ABC transporter |
| orf4 (SEQ ID NO 9) | 3403–4293 | 296 (SEQ ID NO:24) | BAB69248 Pfam PF00528 | 67% | ABC transporter |
| orf5 (SEQ ID NO:10) | 4359–5635 | 425 (SEQ ID NO:25) | G75191 Pfam PF00535 | 34% | Dolichol-phosphate mannosyltransferase |
| orf6 (SEQ ID NO:11) | 5822–7234 | 470 (SEQ ID NO:26) | AE007470 | 20% | Dolichol-phosphate mannose protein mannosyltransferase |
| orf7 (SEQ ID NO:12) | 7293–8822 | 509 (SEQ ID NO:27) | X91736 | 29% | Unknown |
| orf8 (SEQ ID NO:13) | 9012–10025 | 337 (SEQ ID NO:28) | X79146 Pfam PF00891 | 27% | methyltransferase |
| orf9 (SEQ ID NO:14) | 29319–30638 | 439 (SEQ ID NO:29) | Z13972 | 32% | D-aminoacyl hydrolase superfamily |
| orf10 (SEQ ID NO:15) | 30658–32010 | 450 (SEQ ID NO:30) | BAB69335 | 29% | efflux protein |
| orf11 (SEQ ID NO:16) | 32181–33407 | 408 (SEQ ID NO:31) | AF263245 Pfam PF01757 | 38% | isovaleryl transferase |
| orf12 (SEQ ID NO:17) | 33422–34792 | 456 (SEQ ID NO:32) | AF263245 Pfam PF01757 | 31% | isovaleryl transferase |
| orf13 (SEQ ID NO:18) | 34905–35930 | 341 (SEQ ID NO:33) | AF210249 | 45% | enduricydidine synthase |
| orf14 (SEQ ID NO:34) | 36383–37264 | 293 (SEQ ID NO:35) | AF110468 | 31% | Transaminase |
| orf15 (SEQ ID NO:36) | 37264–38514 | 415 (SEQ ID NO:37) | AE001954 | 30% | Transaminase |
| orf16A (SEQ ID NO:38) | 38466–39374 | 302 (SEQ ID NO:39) | ZP_00095168 | 38% | hypothetical protein |
| orf16B (SEQ ID NO:54) | 39389–40375 | 329 (SEQ ID NO:55) | NP_629045 | 34% | putative regulatory protein |
| orf17 (SEQ ID NO:40) | 40440–40655 | 71 SEQ ID NO:41) | AL035654 | 69% | cda-orfX homolog |
| orf18 (SEQ ID NO:42) | 46384–47649 | 421 (SEQ ID NO:43) | NP 823141.1 | 53% | putative secreted protein |
| orf19 (SEQ ID NO:44) | 44182–45813 | 543 (SEQ ID NO:45) | ZP 00058556.1 | 29% | hypothetical protein |
| orf20 (SEQ ID NO:46) | 43248–44168 | 306 (SEQ ID NO:47) | NP 422360.1 | 42% | ABC transporter |

TABLE 1-continued

ORF Correlation

| Orf | Position (bp) | No. Amino Acids | Sequence Homolog Accession No.* | Percent Identity | Proposed Function |
|---|---|---|---|---|---|
| orf21 (SEQ ID NO:48) | 42817—43245 | 142 (SEQ ID NO:49) | NP 826991.1 | 38% | putative lipoprotein |
| orf22 (SEQ ID NO:50) | 41586—42758 | 390 (SEQ ID NO:51) | AAP03102.1 | 34% | two component sensor kinase |
| orf23 (SEQ ID NO:52) | 40773—41441 | 222 (SEQ ID NO:53) | AAP03103.1 | 58% | two component response regulator |
| orf24 (SEQ ID NO:56) | 47770—48180 | 136 (SEQ ID NO:57) | CAD18970.1 | 60% | putative lactone-dependent transcriptional regulator |
| mppA (SEQ ID NO:3) | 10069—18309 | 2747 (SEQ ID NO:2) | AL035640 | | NRPS |
| mppB (SEQ ID NO:5) | 18309—29312 | 3668 (SEQ ID NO:4) | AL035640 | | NRPS |

*SeqWeb ™, which uses Wisconsin [GCG] Package version 10

Methods of Modifying Bacterial Proteins

The role of the proteins encoded by mppA (SEQ ID NO:3), mppB (SEQ ID NO:5), or ORF1–ORF24 (as described in Table 1) may be evaluated using any method known in the art. For example, specific modifications to a protein sequence may be produced to alter the final product. Other non-limiting examples of studies that may be conducted with these proteins include (i) evaluation of the biological activity of a protein and (ii) manipulation of a synthetic pathway to alter the final product from bacteria. More detailed discussion of these proposed uses follows.

Genetic manipulations and expression of the proteins discussed herein may be conducted by any method known in the art. For example, the effect of point mutations may be evaluated. The mutations may be produced by any method known in the art. In one specific method the manipulations and protein expression may be conducted using a vector that comprises at least one Gram-negative and at least one Gram-positive origin of replication. The origins of replication allow for replication of the nucleic acid encoded by the vector, in either a Gram-negative or a Gram-positive cell line. In one embodiment, the vector comprises one Gram-negative and one Gram-positive origin of replication. Additionally, the vector comprises a multiple cloning site that allows for the insertion of a heterologous nucleic acid that may be replicated and transcribed by a host cell.

The most evolved mechanism of transfer of nucleic acids is conjugation. As used herein, the term "conjugation" refers to the direct transfer of nucleic acid from one prokaryotic cell to another via direct contact of cells. The origin of transfer is determined by a vector, so that both donor and recipient cells obtain copies of the vector. Transmissibility by conjugation is controlled by a set of genes in the tra region, which also has the ability to mobilize the transfer of chromosomes when the origin of transfer is integrated into them (Pansegrau et al., *J. Mol. Biol.*, 239:623–663, 1994; Fong and Stanisich, *J. Bact.*, 175:448–456, 1993).

Evaluation of the Biological Activity of a Protein

Evaluation of the mechanism of a protein and role the protein plays in the synthesis of a compound has traditionally been determined using sequence homology techniques. However, such techniques may not be accurate and better methods of evaluating novel proteins need to be developed. The vector described previously may be used to assess the biological activity of an unknown protein. The vector may be used to disrupt a protein, either by partial or complete removal of the gene encoding the protein, or by disruption of that gene. Evaluation of the products produced when the altered protein is present is useful in determining the function of the protein.

Manipulation of a Synthetic Pathway to Alter the Final Product

As discussed above, many compounds obtained from organisms have complex stereochemistries. These compounds are not amenable to production or manipulation by conventional synthetic methods. Therefore, new methods are needed to produce altered products.

Specific proteins within the biochemical pathway of the product may be modified to assess the activity of the compounds produced by these altered proteins and to determine which sections of the product are important for activity and function.

The present invention contemplates any method of altering any of the proteins of the present invention. More specifically, the invention contemplates any method that would insert amino acids, delete amino acids or replace amino acids in the proteins of the invention. Additionally, a whole domain in a module in MppA (SEQ ID NO:2) or MppB (SEQ ID NO:4) may be replaced. Therefore, for example, the acylation domain that incorporates tyrosine into the final product may be replaced with a domain that incorporates serine. The modifications may be performed at the nucleic acid level. These modifications are performed by standard techniques and are well known within the art.

Upon production of the nucleic acid encoding the modified protein, the protein can be expressed in a host cell. Then the host cell can be cultured under conditions that permit production of a product of the altered pathway.

Once the product is isolated, the activity of the product may be assessed using any method known in the art. The activity can be compared to the product of the non-modified biosynthetic pathway and to products produced by other modifications. Correlations may be drawn between specific alterations and activity. For example, it may be determined that an active residue at a specific position may increase activity. These types of correlations will allow one of ordinary skill to determine the most preferred product structure for specified activity.

The present invention also contemplates a method for using an intergeneric vector, described infra in the examples, to manipulate, modify, or isolate a protein involved in the synthesis of a specific product. For example, the vector of the present invention may be used to alter an enzyme which is involved in incorporation of an alanine residue into a peptide, so that a tyrosine residue is incorporated instead. The effect of this modification on peptide function may be then evaluated for biological efficacy. In the above example, modifications to the enzyme may include, but are not limited to, removal of amino acids and/or sequences that specifically recognize alanine and/or incorporation of amino acids and/or sequences that specifically recognize tyrosine.

Therefore, in general terms, the vector of the present invention may be used to alter a gene sequence by insertion of nucleic acid sequences, deletion of nucleic acid sequences, or alteration of specific bases within a nucleic acid sequence to alter the sequence of a protein of interest; thereby producing a modified protein of interest. Preferably, the protein of interest is involved in the synthesis of a compound of interest. The method of modifying a protein comprises (i) transfecting a first bacterial cell with the vector of the present invention, (ii) culturing the first bacterial cell under conditions that allow for replication of the vector, (iii) conjugating the first bacterial cell with a second bacterial cell under conditions that allow for the direct transfer of the vector from the first bacterial cell to the second bacterial cell, and (iv) isolating the second bacterial cell transformed with the vector. In a preferred embodiment, the first cell is a Gram-negative bacterial cell and the second cell is a Gram-positive cell.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994).

"Amplification" of DNA as used herein denotes the use of polymerase chain reaction (PCR) to increase the concentration of a particular DNA sequence within a mixture of DNA sequences. For a description of PCR see Saiki et al., Science 1988, 239:487.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA—DNA, DNA-RNA and RNA—RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "promoter" or "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" expression control sequences in a cell when RNA polymerase transcribes the coding sequence into RNA, particularly mRNA, which is then trans-RNA spliced (if it contains introns) and translated into the protein encoded by the coding sequence.

The term "expression control sequence" refers to a promoter and any enhancer or suppression elements that combine to regulate the transcription of a coding sequence. In a preferred embodiment, the element is an origin of replication.

The terms "vector", "cloning vector" and "expression vector" refer to the vehicle by which DNA can be introduced into a host cell, resulting in expression of the introduced sequence. In one embodiment, vectors comprise a promoter and one or more control elements (e.g., enhancer elements) that are heterologous to the introduced DNA but are recognized and used by the host cell. In another embodiment, the sequence that is introduced into the vector retains its natural promoter that may be recognized and expressed by the host cell (Bormann et al., J. Bacteriol 1996; 178:1216–1218).

An "intergeneric vector" is a vector that permits intergeneric conjugation, i.e., utilizes a system of passing DNA from *E. coli* to actinomycetes directly (Keiser, T. et al., Practical *Streptomyces* Genetics (2000) John Innes Foundation, John Innes Centre (England)). Intergeneric conjugation has fewer manipulations than transformation.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct". A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes. Vector constructs may be produced using conventional molecular biology and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); F. M. Ausubel et al. (eds.), Current Protocols in Molecular Biology, John Wiley & Sons, Inc. (1994).

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cells genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The term "host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal). For the present invention, host cells include but are not limited to *Streptomyces* species and *E. Coli*.

The term "expression system" means a host cell and compatible vector under suitable conditions, e.g. for the expression of a protein coded for by foreign DNA carried by the vector and introduced to the host cell. In a specific embodiment, the host cell of the present invention is a Gram-negative or Gram-positive bacteria. These bacteria include, but are not limited to, *E. coli* and *Streptomyces* species. An example of a *Streptomyces* species that may be used includes, but is not limited to, *Streptomyces hygroscopicus*.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. For example, the present invention includes chimeric DNA molecules that comprise a DNA sequence and a heterologous DNA sequence which is not part of the DNA sequence. In this context, the heterologous DNA sequence refers to an DNA sequence that is not naturally located within the NRPS sequence. Alternatively, the heterologous DNA sequence may be naturally located within the NRPS sequence, but is found at a location in the NRPS sequence where it does not naturally occur. A heterologous expression regulatory element is such an element is operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence.

The term "variant" may also be used to indicate a modified or altered gene, DNA sequence, enzyme, cell, etc., i.e., any kind of mutant. Two specific types of variants are "sequence-conservative variants", a polynucleotide sequence where a change of one or more nucleotides in a given codon position results in no alteration in the amino acid encoded at that position, and "function-conservative variants", where a given amino acid residue in a protein or enzyme has been changed without altering the overall conformation and function of the polypeptide. Amino acids with similar properties are well known in the art. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Clustal Method, wherein similarity is based on the algorithms available in MEGALIGN. A "function-conservative variant" also includes a polypeptide or enzyme which has at least 60% amino acid identity as determined by BLAST or FASTA alignments, preferably at least 75%, more preferably at least 85%, and most preferably at least 90%, and which has the same or substantially similar properties or functions as the native or parent protein or enzyme to which it is compared.

As used herein, the terms "homologous" and "homology" refer to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Accordingly, the term "sequence similarity" refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90% or 95% of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar. Preferably, the amino acids are functionally identical. Preferably, the similar or homologous sequences are identified by alignment using, for example, the GCG (Genetics Computer Group, Program Manual for the GCG Package, Version 10, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligoncucleotide molecules used. Exemplary temperatures may be 37° C. (for 14-base oligonucleotides), 48° C. (for 17-base oligonucleotides), 55° C. (for 20-base oligonucleotides) and 60° C. (for 23-base oligonucleotides). Exemplary suitable hybridization conditions for oligonucleotides include washing in 6×SSC/ 0.05% sodium pyrophosphate, or other conditions that afford equivalent levels of hybridization.

EXAMPLES

The present invention will be better understood by reference to the following Examples, which are provided as exemplary of the invention, and not by way of limitation.

Example 1

Identification and Cloning of the Non-Ribosomal Peptide Synthetase Complex Responsible for Antibiotic Production (AC98) in *S. hygroscopicus*

Methods

Isolation of genomic DNA from *S. hygroscopicus*. *Streptomyces hygroscopicus* strain designated NS17 was cultured by inoculation of 25 ml of sterile tryptone soya broth (TSB) (Oxoid, Ogdensberg, N.Y.) prepared by combining 30 g of TSB in 1 L of distilled water) with 100 µl of a frozen glycerol stock of NS17. Cultures were grown at 28° C. while shaking at 200 rpm for 2 days. Cells were harvested by centrifugation at 3000×g for 10 min, followed by resuspension of the pelleted cells in 2 ml lysis buffer (2% Triton X-200, 1% SDS, 100 mM NaCl, 10 mM Tris, pH 8.0, 1 mm EDTA) and vortexing. After vortexing, 2 ml of phenol/ chloroform/isoamyl alcohol (25/24/1 v/v) was added and the suspension was vortexed again for about 1 min to ensure lysis. The sample was then centrifuged for 5 min at 3000×g and the aqueous phase was added to 2 volumes of 95% ethanol to precipitate the genomic DNA. The precipitate was collected by centrifugation or by spooling, washed once with 70% ethanol, and air dried. DNA was resuspended in 100 µl of TE buffer (10 mM Tris, 1 mM EDTA, pH 8.0).

Isolation of a peptide synthetase probe and Southern hybridization. Degenerate PCR primers were designed based on the highly conserved core motifs of peptide synthetase adenylation domains A3 and A8 (Marahiel et al., 1997).

```
forward   5'-ACG/CTCG/CGGCT/ACGCACCGGCCIGCCG/CAAG-3'           (SEQ ID NO: 19)
primer
reverse   5' AGCTCG/CAT/CG/CCGG/CTAGCCG/CCGG/CAT/CCTTG/CACCTG-3'  (SEQ ID NO: 20)
primer
G/C or T/A or T/C denote either base at that position
```

NS17 genomic DNA was used as a template to synthesize a fragment of about 800 bp in length by PCR using a Perkin Elmer DNA Thermal Cycler 480 (Boston, Mass.-30 cycles: 95° C.-1 min, 55° C.-1 min, 72° C.-1 min). This fragment was subjected to end sequencing using an Applied Biosystems, Inc. ABI3700 sequencer (Foster City, Calif.) to determine that it corresponded to a portion of peptide synthetase adenylation domain, and used to as a probe in Southern hybridization of NS17 genomic DNA under standard conditions (Sambrook et al., 1989).

Identification of a functional NS17 peptide synthetase module. A 3 kb fragment containing a putative peptide synthetase module identified from the Southern hybridization was sequenced as described above for confirmation, and used in a biosynthetic assay to determine whether the putative peptide synthetase module was part of the AC98 biosynthetic cluster. Specifically, the method described under Example 2, below, was used to insertionally inactivate the putative peptide synthetase, which was then used to replace the endogenous peptide synthetase in S. hygroscopicus NS17, by homologous recombination. If the 3 kb fragment was part of the AC98 biosynthetic gene cluster, replacement of the endogenous gene with the insertionally inactivated 3 kb fragment would inhibit antibiotic production if the peptide synthetase encoded by 3 kb fragment is part of the AC98 biosynthetic cluster.

To evaluate antibiotic production, samples were removed from 50 ml cultures NS17 carrying the disrupted gene. Cultures were grown at 28° C. in PharmaMedia (Chrysalis PharmaMedia, NJ:10 g/L PharmaMedia, 5 g/L CaCO$_3$, 40 g/L glucose) and were analyzed by HPLC. 20 µl aliquots were loaded onto a Waters 4 mm×50 mm YMC ods-a-columm (Milford, Mass.) and eluted with a gradient of 10% acetonitrile/90% TFA (20%) in water to 34% acetonitrile/66% TFA in water over 15 minutes. AC98 related compounds were detected by UV-DAD at 226 nm. Chromatograms were compared to chromatograms of samples taken from a similarly treated culture of the parental strain.

Preparation and Screening of an NS17 Cosmid Library. Genomic DNA isolated from NS17 as described above was used for the construction of a cosmid library. Optimal conditions for partial digestion of the DNA by restriction enzymes, to produce DNA fragments of about 35 kb, was determined using published techniques (Sambrook et al, 1989). The digested DNA fragments were dephosphorylated with calf intestinal alkaline phosphatase (New England Biolabs, Beverly, Mass.) according to the protocol provided by the manufacturer, and ligated into the commercial vector, pWE 15 (Stratagene, La Jolla, Calif.) according to the manufacturer's instructions. Packaging of the ligated mixture was accomplished using Gigapack III XL packaging extract (Stratagene), and the resulting library was titered and amplified according to the manufacturer's instructions.

The cosmid library was screened using the 3 kb peptide synthetase fragment, identified as described above, according to standard colony hybridization protocols (Sambrook et al., 1989). One cosmid, designated pNWA117, was selected for further study.

Cosmid analysis and identification of ORFs 1–13 (SEQ ID NOs:6–18). Cosmid pNWA117 was digested with EcoRI, subjected to agarose gel electrophoresis and used in a Southern hybridization with the 3 kb fragment, identified as described above, as a probe. Following confirmation that the pNWA117 contained the 3 kb fragment, the cosmid was sequenced (MWG Biotech, Highpoint, N.C.).

Nucleotide BLAST analysis (SeqWeb™, which uses Wisconsin [GCG]Package version 10) was performed to identify individual ORFs and their putative function, according to their homology with known sequences. Results are presented in Table 1.

Cosmid analysis and identification of ORFs 14–24. Genomic DNA downstream of pNWA117 was isolated from a cosmid library by using a fragment of DNA from ORF12 of the analyzed sequence to select cosmids containing stretches of genomic DNA encoding that region of AC98 biosynthetic pathway. This process is commonly referred to as chromosomal walking. One such cosmid, pNWA105, was selected after restriction analysis indicated that it contained approximately 12 Kb of DNA downstream of ORF13. Nucleotide BLAST analysis of sequence data obtained was performed to identify twelve complete ORFs (ORF14 (SEQ ID NO:34), ORF15 (SEQ ID NO:36), ORF16A (SEQ ID NO:38) and ORF16B (SEQ ID NO:54), ORF17 (SEQ ID NO:40), ORF18 (SEQ ID NO:42), ORF19 (SEQ ID NO:44), ORF20 (SEQ ID NO:46), ORF21 (SEQ ID NO:48), ORF22 (SEQ ID NO:50), ORF23 (SEQ ID NO:52), and ORF24 (SEQ ID NO:56)), and their putative function in AC98 biosynthesis, according to their homology with known sequences. Results are presented in Table 1.

Results

Isolation of an NRPS in NC17 responsible for the production of AC98. Results from the experiments described above demonstrate that cosmid pNWA117 contains the genes encoding a NRPS required for the synthesis of the peptide core of the novel antibiotic complex AC98, which is produced by the terrestrial actinomycete Streptomyces hygroscopicus. pNWA117 also contains additional ORFs proposed to be involved in the synthesis of the AC98 complex. PNWA105 contains at least 4 additional ORFs that are proposed to be involved in AC98 biosynthesis. The NRPS complex exists as two separate components, MppA (SEQ ID NO:2) and MppB (SEQ ID NO:4). MppA (SEQ ID NO:2) is encoded within bp 10069 and 18309 of the sequence listed in SEQ ID. NO: 1, and is comprised of about 2747 amino acids (SEQ ID NO: 2). MppB (SEQ ID NO:4) is encoded within bp 18309 and 29312 of the sequence listed in SEQ ID NO: 1, and is comprised of about 3668 amino acids (SEQ ID NO: 3). Additional description and characterization of MppA (SEQ ID NO:2) and MppB (SEQ ID NO:4) is described infra, under the heading DETAILED DESCRIPTION.

Table 1 lists the 24 ORFs and corresponding SEQ ID NO's that were identified and determined to be tailoring enzymes involved in the production of the protein core of AC98 (column 1). Column 2 lists the bp position of each ORF according to the sequence contained within cosmid pNWA117 (SEQ ID NO: 1), along with the number of the amino acids encoded by each ORF (column 3). Column 4 identifies the public sequence with which each ORF is most homologous, according to BLAST analysis, and column 5 lists the proposed function of each polypeptide encoded by the individual ORFs based on the sequence homology.

Example 2

Preparation of an Intergeneric Vector

Materials

DNA restriction and modification enzymes and T4 DNA ligase were obtained from New England Biolabs. Plasmid DNA was isolated using commercial kits (Qiagen) and DNA fragments were purified using commercial kits (Tetra Link International). Competent E. coli cells were obtained from Stratagene. All were used according to manufacturer's specifications and with buffers and reagents supplied by the manufacturer. Streptomyces chromosomal DNA was prepared according to published protocols (Keisser et al. Practical Streptomyces Genetics, John Innes Centre, Norwich, England, 2000). Antibiotics were purchased from Sigma.

Methods pNWA200 vector preparation. A purified PstI fragment containing oriT from the R plasmid, RP4, was ligated to pFD666 (Denis & Brzezinski, *Gene*, 111:115, 1992), which was then linearized by digestion with PstI and dephosphorylated with calf intestinal phosphatase. This ligation mixture was transformed into competent XL-10 *E. coli* cells (Stratagene) following manufacturer's directions. The transformed cells were then plated onto nutrient agar plates containing 50 µg/ml kanamycin and incubated at 37° C. for 1 day. The incubation resulted in about 150 colonies. The colonies were replica plated onto a second kanamycin containing agar plate covered by a positively charged nylon filter, and after 6 hours incubation, the nylon filter containing the embedded colonies was treated with 0.5M NaOH (in 1M NaCl) to lyse the bacteria and denature their DNA according to standard Southern blotting procedures (Southern et al., *J Mol. Biol.*, 98:503, 1975). The nylon filter was probed with a radioactively labeled 0.76 kb PstI fragment and one colony was selected on the basis of its hybridizing signal. The recombinant plasmid was then extracted from a fresh culture of the original hybridizing colony. Digestion of the plasmid with PstI produced two DNA fragments which electrophoresed to positions of 5.25 kb and 0.76 kb, corresponding to linear pFD666 (5.25 kb) and the 0.76 kb oriT containing Pst1 fragment. This recombinant vector replicated stably in *E coli* strains and did not show genetic rearrangement upon repeated subculturing and further isolation.

Example 3

Methods for the Modification of the NRPS AC98 Peptide Core

Based on the sequence data of MppA (SEQ ID NO:2) and MppB (SEQ ID NO:4) described above, and available data defining the critical binding pocket features, i.e., amino acid residues in the adenylation domain that determine the specificity of the amino acid that is accepted by the domain, those skilled in the art will be able to modify any of the adenylation domains of the NRPS and change the primary amino acid sequence in the peptide core of AC98, thus, modifying the properties of the molecule. This Example provides two methods for modifying the peptide core.

Preparation of an engineered bacterial strain that produces AC98. Preparation of an AC98-producing host strain for use for the production of modified AC98 described by the methods below, is done according to the following steps:

1. Clone a fragment of the adenylation domain from and NRPS of choice (e.g., using *E. coli*).

2. Insert an antibiotic resistance determinant, such as apramycin, within the cloned fragment from step 1, above. This insertion inactivates adenylation domain after it is inserted into a host genome.

3. Clone the construct in an intergeneric conjugation vector, such as pNWA200, which contains a second antibiotic resistance determinant, such as kanamycin.

4. Introduce the vector containing the cloned construct into an AC98-producing strain.

5. Select for a strain that has the construct integrated into the homologous region of the host's genomic DNA by screening for conjugates that are apramycin-resistant and kanamycin-sensitive.

6. Confirm integration of the apramycin resistance determinant at the desired location by southern hybridization and fermentation.

Once the proper host strain is selected, the insertionally inactivated module in the host genome can be replaced by either the same module that has been modified by site-directed mutagenesis, or by a module that has an adenylation domain that specifies acceptance of a different amino acid.

Method 1

Modification of the adenylation domain for the production of modified AC98. The cloned module of choice, e.g., the adenylation domain, is modified by introducing nucleotide changes that will alter the codons that specify the incorporation of the amino acids critical to the biding pocket. The nucleotide changes can be introduced using any method known in the art, such as site-directed mutagenesis. For example, changing the triplet codon for Ser239 in the tyrosine binding pocket of MppB (SEQ ID NO:4) from TCC to TGG, and changing the triplet codon for Valine299 from GTC to ATC, would change the amino acids at those sites to tryptophan and isoleucine, respectively. According to published data, one would expect that these changes would alter the specificity of the module from tyrosine to phenylalanine (Stachelhaus et al., Chemistry and Biol. 1999; 6:493–505).

The mutated module is then introduced, by conjugation, into a host strain that has been modified, as outlined above, to be resistant to an antibiotic, such as apramycin. Selection for the presence of a recombinant strain is two-fold. First, exconjugates are selected that are able to grown in the presence of kanamycin and apramycin. These strains represent those that have taken up the vector construct. Second, clones are selected that have lost resistance to both kanamycin and apramycin. This indicates that the susceptible clones have lost the apramycin resistance due to homologous recombination between the insertionally inactivated host tyrosine domain and the site-directed mutant version of the tyrosine domain. This loss of resistance further indicates that the vector is no longer in the host strain, and the mutated version of the tyrosine domain (i.e., the one specific for phenylalanine) replaced the insertionally inactivated tyrosine domain of the host (engineered as described above). Southern hybridization is then performed to confirm the insertion of the correct construct. Fermentation of the strain will result in the production of modified AC98 products where the cyclic peptide core contains phenylalanine in place of tyrosine.

Method 2

Module replacement or swapping for the production of modified AC98. For this method, two regions of approximately 1 kb flanking the module selected for replacement are cloned by PCR (the "arms"). The two arms are engineered so that the ends closest to the module (i.e., the 3' end on one arm and the 5' arm on the other) have appropriate restriction sites for subsequent insertion of the module in the correct orientation between the flanking arms. Next, the module of choice for insertion from another peptide synthetase (e.g., the threonine module from the CDA NRPS of *S. coelicolor*) is amplified by PCR. This PCR product is also engineered to contain the appropriate restriction sites compatible with those present in the cloned arms, in order for insertion between the two arms. After ligation of the arms and the module, the construct is transferred to the intergeneric conjugation vector, and introduced into a antibiotic-resistant host strain (e.g., the apramycin-resistant strain as described above). Selection of the conjugates is then performed as described above for the mutated module method. Those strains expressing the threonine module from the CDA NRPS instead of the tyrosine module of the AC98 NRPS are identified as being the result of homologous recombination between the arms of the vector and the homologous regions on the host NRPS that flank the insertionally inactivated tyrosine module. Production of the modified AC98, where the cyclic peptide core contains threonine, is achieved by fermentation.

Appropriate steps should be taken to ensure maintenance of the integrity of the ORFs during the processes described above. For example, sequencing of all PCR products is preferred to confirm that no inadvertent mutations are introduced into the sequences that will be used for cloning.

In addition or as an alternative to the peptide synthetase module of the NRPS, tailoring enzymes, such as those indicated in Table 1, may also be modified according to these methods in order to produce antibiotic molecules having a modified peptide core. As one example, inactivation of a methyltransferase enzyme will result in an antibiotic lacking specific methyl groups, which then may be evaluated for improved antibiotic activity.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

Patents, patent applications, publications, procedures, and the like are cited throughout this application, the disclosures of which are incorporated herein by reference in their entireties.

The invention claimed is:

1. An isolated nucleic acid having a nucleotide sequence selected from the group consisting of:
    (a) a nucleotide sequence that encodes a polypeptide having the amino acid sequence of SEQ ID NO: 4;
    (b) a nucleic acid sequence that hybridizes to a nucleotide sequence encoding a polypeptide having the nucleotide sequence of SEQ ID NO: 5, said hybridization being performed under the following stringent conditions: 68° C. in 0.2×SSC; or 42° C. in 50% formamide; wherein the nucleotide sequence encodes an MppB protein capable of forming an NRPS complex with the MppA protein of SEQ ID NO:2; and
    (c) an isolated nucleic acid fragment having a nucleotide sequence complementary to the full length of nucleotide sequence of (a), or (b).

2. An isolated nucleic acid of claim 1, wherein the nucleic acid has a nucleotide sequence of SEQ ID NO: 5.

3. An isolated nucleic acid according to claim 1, wherein the nucleic acid has a nucleotide sequence that is complementary to the sequence of SEQ ID NO: 5.

4. An isolated host cell genetically modified to express the nucleic acid of claim 1.

5. An isolated nucleic acid of SEQ ID NO: 5, or the full-length complement thereof.

6. A chimeric nucleic acid construct comprising a nucleic acid of any one of claims 1, 2, 3, or 5, wherein said nucleic acid is operatively associated with an expression control sequence.

7. An expression vector comprising the nucleic acid of any one of claims 1, 2, 3, or 5, wherein the nucleic acid is operatively associated with an expression control sequence.

8. An isolated host cell genetically modified to express the nucleic acid of any one of claims 1, 2, 3, or 5.

9. An isolated host cell comprising the expression vector of claim 7.

10. An expression vector comprising a nucleic acid sequence having a nucleotide sequence encoding a polypeptide having an amino acid sequence as set forth in SEQ ID NO: 4, wherein the nucleic acid sequence is operatively associated with an expression control sequence.

11. An expression vector comprising a nucleic acid sequence having a nucleotide sequence encoding a polypeptide having an amino acid sequence as set forth in SEQ ID NO: 4, wherein the nucleic acid sequence is operatively associated with an expression control sequence, and further comprising a second nucleic acid sequence having a nucleotide sequence encoding a polypeptide having an amino acid sequence as set forth in SEQ ID NO: 2, wherein said second nucleic acid sequence is operatively associated with an expression control sequence.

12. The expression vector of claim 11, further comprising a nucleic acid sequence having a nucleotide sequence encoding a polypeptide having an amino acid sequence as set forth in any one of SEQ ID NOs: 21–33, 35, 37, 39, 41, 43, 45, 46, 49, 51, 53, 55, or 57, wherein said nucleic acid sequence is operatively associated with an expression control sequence.

13. An isolated host cell comprising the expression vector of claim 11.

14. The host cell of claim 13, further comprising nucleic acid sequences having nucleotide sequences encoding polypeptides having amino acid sequences as set forth in SEQ ID NOs: 21–33, 35, 37, 39, 41, 43, 45, 47, 49, 51, 53, 55, and 57.

15. The host cell of claim 14, wherein the nucleic acids have nucleotide sequences depicted in SEQ ID NOs: 6–18, 34, 36, 38, 40, 42, 44, 46, 48, 50, 52, 54, and 56.

16. A method for producing NRPS, which method comprises isolating NRPS produced by the host cell of claim 14, wherein NRPS is comprised of MppA of SEQ ID NO:2 and MppB of SEQ ID NO:4, and wherein the host cell has been cultured under conditions that provide for expression of MppA of SEQ ID NO:2 and MppB of SEQ ID NO:4.

17. An isolated host cell genetically modified to express the nucleic acid having nucleotide sequence as depicted in SEQ ID NO. 1.

* * * * *